US008626452B2

(12) United States Patent
Urry et al.

(10) Patent No.: US 8,626,452 B2
(45) Date of Patent: Jan. 7, 2014

(54) COMPOSITIONS AND METHODS FOR OPTIMIZING DRUG HYDROPHOBICITY AND DRUG DELIVERY TO CELLS

(76) Inventors: Dan W. Urry, Vestavia Hills, AL (US); Kelley D. Urry, Vestavia Hills, AL (US)

(*) Notice: Subject to any disclaimer, the term of this patent is extended or adjusted under 35 U.S.C. 154(b) by 550 days.

(21) Appl. No.: 12/797,465

(22) Filed: Jun. 9, 2010

(65) Prior Publication Data
US 2010/0330606 A1 Dec. 30, 2010

Related U.S. Application Data

(60) Provisional application No. 61/185,405, filed on Jun. 9, 2009, provisional application No. 61/316,173, filed on Mar. 22, 2010.

(51) Int. Cl.
G06F 19/00 (2011.01)
G01N 31/00 (2006.01)
C12Q 1/02 (2006.01)

(52) U.S. Cl.
USPC .................... 702/30; 702/22; 702/27; 435/29

(58) Field of Classification Search
None
See application file for complete search history.

(56) References Cited

U.S. PATENT DOCUMENTS

| 2003/0044845 A1 | 3/2003 | Jenkins et al. |
| 2007/0161605 A1 | 7/2007 | Cheng et al. |

OTHER PUBLICATIONS

Velazquez-Campoy et al. The application of thermodynamic methods in drug design. Thermochimica Acta. 2001. vol. 380, pp. 217-227.*
Cortez-Selva et al., "SAR Studies of Dihydro-beta-agarofuran Sesquiterpenes as Inhibitors of the Mltidrug-Resistance Phenotype in a Leishmania tropica Line Overexpressing a P-Glyycoprotein-Like Transporter", J.Med.Chem. 2004, 47(3), pp. 579-587.
Dawson et al., "Stucture of a bacterial multidrug ABC transporter", Nature vol. 443, Sep. 14, 2006, pp. 180-185.
Table 5.3 of Urry DW. "What sustains life? Consilient mechanisms for protein-based machines and materials." Springer (Birkhauser), LLC, New York, ISBN: 08176 4346 X. 2006.
Table 5.2 of Urry DW. "What sustains life? Consilient mechanisms for protein-based machines and materials." Springer (Birkhauser), LLC, New York, ISBN: 08176 4346 X. 2006.
Urry Dan, "The change in Gibbs free energy for hydrophobic association: Derivation and evaluation by means of inverse temperature transitions", Chemical Physics Letters, May 11, 2004; vol. 399, pp. 177-183.
Urry et al. "Function of the F1-motor (F1-ATPase) of ATP synthase by apolar-polar repulsion through internal interfacial water", Cell Biology International 30 (2006) 44-45, accepted Sep. 30, 2005.
Dawson et al., "Structure of the multidrug ABC transporter Sav1866 from Staphylococcus aureus in complex with AMP-PNP" Institute of Molecular Biology and Biophysics, ETH Zurich HPK D14.3, 8093 Zurich, Switzerland, FEBS Letters 581 (2007) 935-938, revised Jan. 26, 2007; accepted Jan. 26, 2007.
Protein Data Bank, Accession Code 2ONJ (As of Jun. 3, 2011).
Dawson et al., "Structure of a bacterial multidrug ABC transporter", Nature Publishing Group, Sep. 14, 2006; vol. 443, pp. 180-185.
Protein Data Bank, Accession Code 2HYD (As of May 16, 2011).
Menz et al., "Structure of Bovine Mitochondrial F1-ATPase with Nucleotide Bound to All Three Catalytic Sites: Implications for the Mechanism of Rotary Catalysis", 1Medical Research Council Laboratory of Molecular Biology, Cell, vol. 106, 331-341, Aug. 10, 2001.
Protein Data Bank, Accession Code 1H8E (As of Jun. 3, 2011).
Abrahams et al., "Structure at 2.8 A resolution of F1-ATPase from bovine heart mitochondria", Nature Publishing Group, (London) Aug. 25, 1994; vol. 370; pp. 621-628.
Protein Data Bank, Accession Code 1BMF (As of May 11, 2011).
Xu et al., "The Crystal Structure of the Asymmetric GroEL-GroES-(ADP)7 chaperonin complex", Nature 1997; Aug. 21; 388: pp. 741-750.
Protein Data Bank, Accession Code 1OAN (As of May 10, 2011).
Urry Dan W., "What sustains life? Consilient mechanisms for protein-based machines and materials". Springer (Birkhauser), LLC, New York, ISBN: 08176 4346 X. 2006, Chapters 7&8.
Urry, "Polymer Data Handbook Second Edition", Edited by James. E. Mark, Table 2F of Urry DW. Luan C-H. Elastic, Plastic, and Hydrogel Protein-based Polymers, Oxford University Press, New York, NY 2009, pp. 121-137.
Protein Data Bank, Accession Code 3G5U (As of Jun. 3, 2011).
Urry et al., "Development of Elastic Protein-based Polymers as Materials for Acoustic Absorption." Mat. Res. Soc. Symp. Proc.: Materials Inspired by Biology, 774, 81-92, 2003.

(Continued)

Primary Examiner — Anne Gussow
Assistant Examiner — Channing S Mahatan
(74) Attorney, Agent, or Firm — Wilson, Sonsini, Goodrich & Rosati

(57) ABSTRACT

Methods to determine drug hydrophobicity and to quantify changes in drug hydrophobicity that optimize drug function by means of differential scanning calorimetry of an endothermic phase transition of a base protein-based polymer, specifically of an elastic-contractile model protein, to which is attached the drug to be evaluated for its hydrophobicity in terms of the change in Gibbs free energy for hydrophobic association, $\Delta G_{HA}$ have been developed. Also described herein is the preparation of nanoparticles comprised of protein-based polymers, specifically of elastic-contractile model proteins, designed for the binding and desired release rate of a specific drug or class of drugs. Further described herein is a means of targeting the drug-laden nanoparticle to a cell by means of decorating the nanoparticle surface with a molecular entity that selectively binds to the diseased cell or disease causing organism, e.g., by decorating the drug-laden nanoparticle surface with synthetic antigen-binding fragment to an up-regulated receptor characteristic of the diseased cell.

13 Claims, 28 Drawing Sheets

(56) References Cited

OTHER PUBLICATIONS

Urry, et al. "Characterization of Waters of Hydrophobic Hydration by Microwave Dielectric Relaxation," J. Amer. Chem. Soc. vol. 119, pp. 1161-1162, 1997.

Urry et al., "Function and Frustration of Multi-Drug ABC Exporter Protein and Design of Model Proteins for Drug Delivery Using Protein Hydration Thermodynamics", *Current Pharmaceutical Design*, 2009, 15, 2833-2867, 2009 Bentham Science Publishers Ltd.

Ward et al., "Flexibility in the ABC transporter MsbA: Alternating access with a twist", PNAS, vol. 104, pp. 19005-19010(2007), www.pnas.org/cgi/doi/10.1073/pnas.0709388104.

Protein Data Bank, Accession Code 3B60 (As of Jun. 3, 2011).

Protein Data Bank, Accession Code 3B5W (As of May 11, 2011).

Aller et al., "Structure of P-Glycoprotein Reveals a Molecular Basis for Poly-Specific Drug Binding", Science, vol. 323, pp. 1718-1722, Mar. 27, 2009.

Urry et al., "Elastic Protein-Based Biomaterials: Elements of Basic Science, Controlled Release and Biocompatibility," Biomaterials Handbook—Advanced Applications of Basic Sciences and Bioengineering; D L. Wise Coord. Ed, Marcel Dekker, Inc., New York, pp. 31-54, 2004.

Uysal et al. "Crystal structure of full-length KcsA in its closed conformation", PNAS, vol. 106., No. 16, pp. 6644-6649(Apr. 21, 2009).

Luan et al., "Solvent Deuteration Enhancement of Hydrophobicity: DSC Studay of the Inverse Temperature Transition of Elastin-Based Polypeptides", The Journal of Physical Chemistry, vol. 95; No. 20, pp. 7896-7900, 1991.

Rodriguez-Cabello et al., "Endothermic and exothermic components of an inverse temperature transition for hydrophobic association by TMDSC", Chemical Physics Letters; vol. 388; pp. 127-131, 2004.

Privalov, Peter L., "Cold Denaturation of Proteins", Biochemistry and Molecular Biology, Rightslink, vol. 25, Issue 4, pp. 281-306, 1990.

Butler J.A.V., "The Energy and enthropy of hydration of organic compounds", Trans Faraday Soc vol. 33; pp. 229-238, 1937.

Urry et al., "Properties, Preparations and Applications of Bioelastic Materials." In Encyclopedic Handbook of Biomaterials and Bioengineering—Part A—Materials, vol. 2, Marcel Dekker, Inc, New York, pp. 1619-1673, 1995.

F. Sciortino et al., "Nucleation and Accretion of Bioelastomeric Fibers at Biological Temperatures and Low Concentrations," Biochemical and Biophysical Research Communications, vol. 157, No. 3, pp. 1061-1066, Dec. 30, 1988.

Urry et al., "Transductional Elastic and Plastic Protein-based Polymers as Potential Medical Devices," in Handbook of Biodegradable Polymers, ed. by Domb, Kost, and Wiseman, Harwood Academic Publishers, Chur, Switzerland, pp. 367-386, 1997.

McCarty et al., "Use of a Monoclonal Anti-Estrogen Receptor Antibody in the Immunohistochemical Evaluation of Human Tumors", *Cancer Res* 1986;46:4244s-4248s. Published online Aug. 1, 1986.

Kinsel et al. "Immunocytochemical Analysis of Estrogen Receptors as a Predictor of Prognosis in Breast Cancer Patients: Comparison with Quantitative Biochemical Methods", Cancer Research 49, 1052-1056, Feb. 15, 1989.

Urry, Dan W , "Free Energy Transduction in Polypeptides and Proteins Based on Inverse Temperature Transitions," Prog. Biophys. Molec. Biol. vol. 57, pp. 23-57, 1992.

\* cited by examiner

Clear solution → heat above 25°C → Cloudy solution → let stand for a few hours at 37°C → Glue-like phase separates out $(GVGVP)_{251}$ in 40 mg/ml of $H_2O$ $T_t = 26.7°C$ Temperature Interval $T_b$ Composition Dependence of $T_t$
for poly[$f_V$(GVGVP),$f_X$(GXGVP)] where $f_X$ = 0.2.

Temperature of Inverse Temperature Transition, $T_t$
Plot of $f_X$ versus $T_t$ for poly[$f_V$(GVGVP),$f_X$(GXGVP)].

$\Delta G_{HA} = \Delta H_t$(GVGVP) $- \Delta H_t$(GXGVP) (kcal/mol)

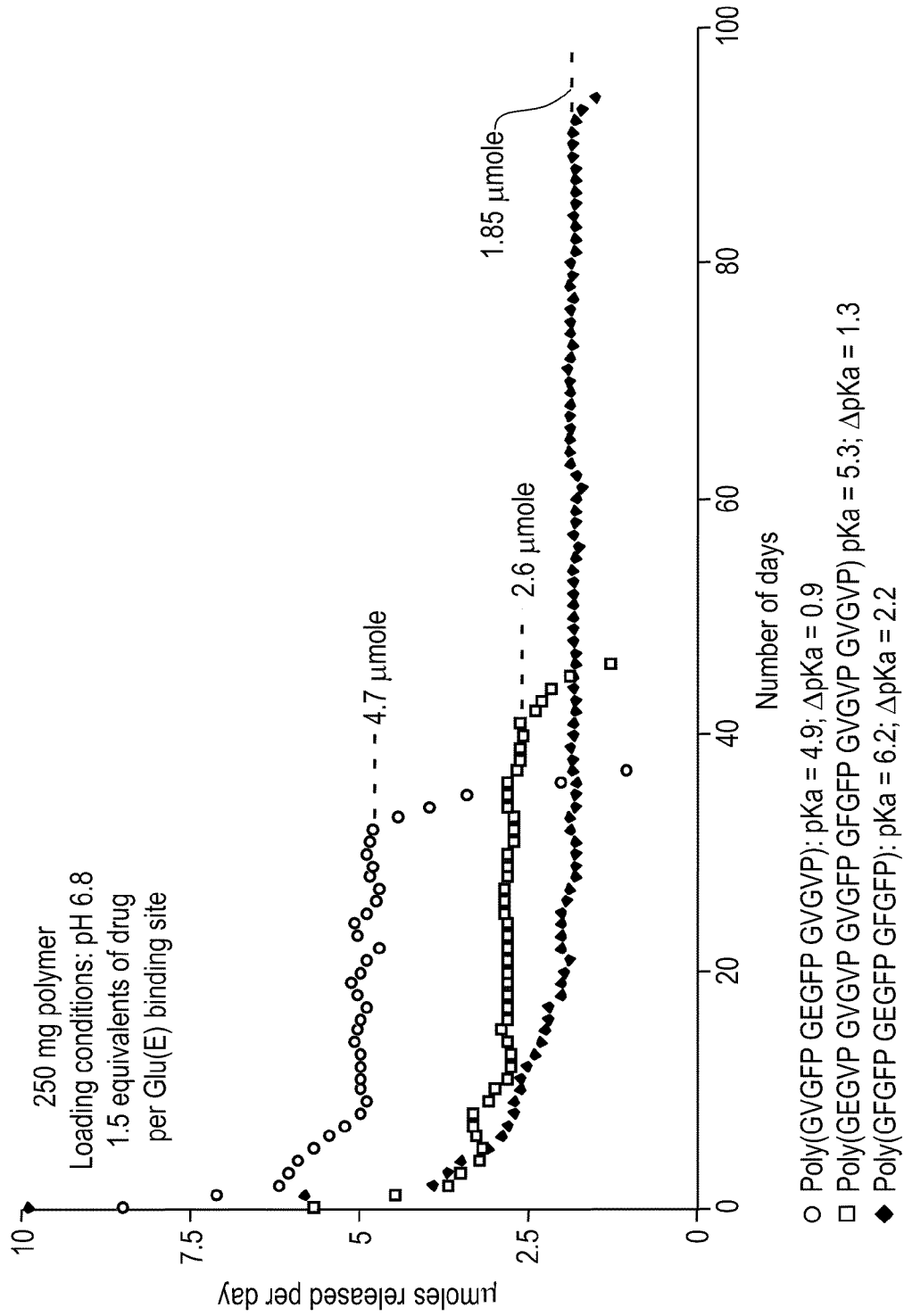

Depicting Apolar-polar Repulsion in Structure 1H8E

1- D315
2- R337
3- E341
4- K382
5- D386
6- I390
7- L391
8- V312
9- A314
10- Y311

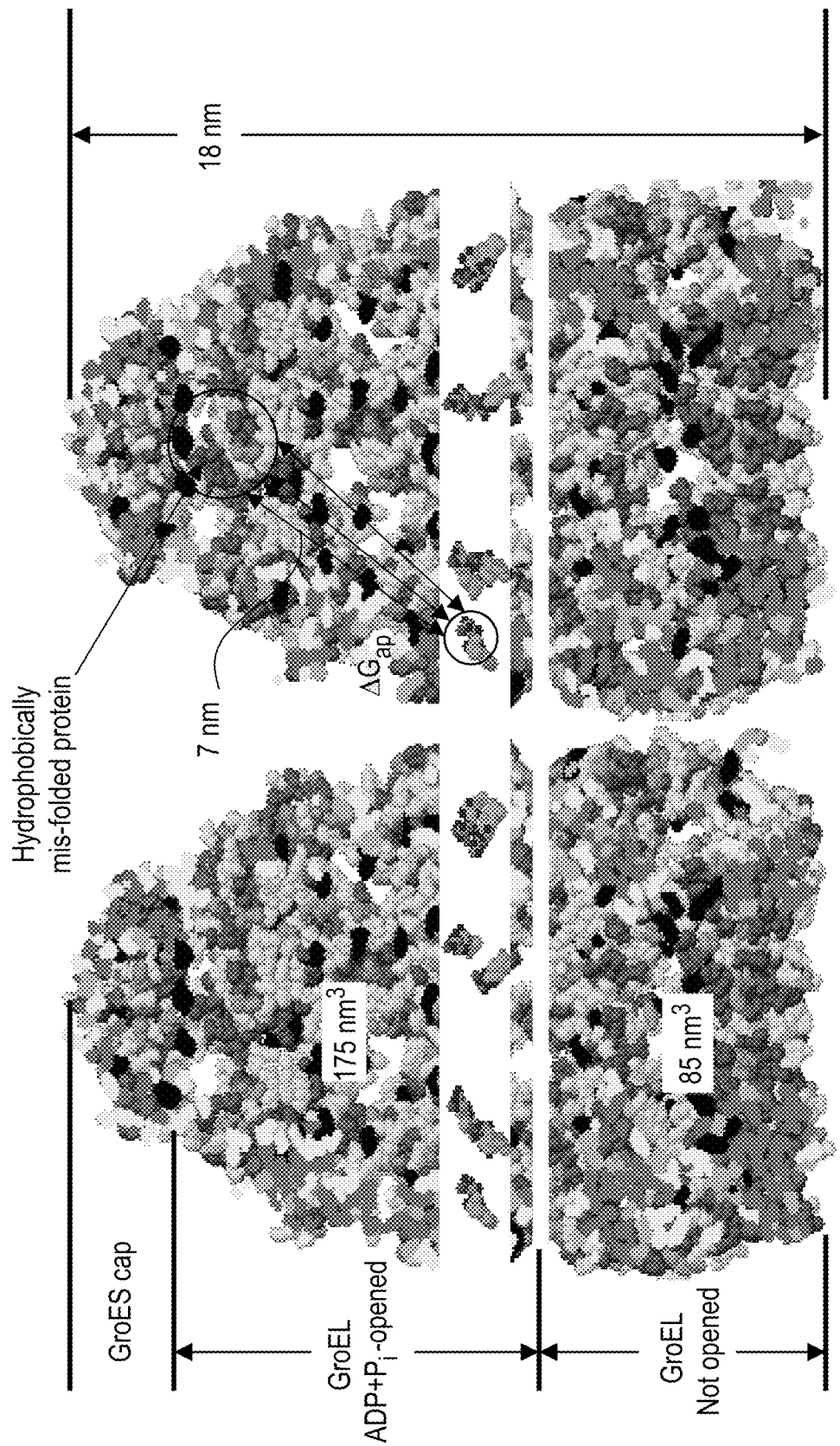

Point of closed throat

E129^A
L196^B
I125^A
I121^A
Q200^B
H204^B
Q130^A
N126^A
N126^B
L196^A
Q200^A
H204^A
I125^B
I121^B
E129^B
Q130^B

Structure 3B5W (opened ~70°)

Structure 3B5X (opened ~30°)

3EFF-Fab1Fab2-proximal end at nanoparticle-st/sf/gr.tif

3EFF-Fab1Fab2-distal end is at antigen binding site-st/sf/gr.tif

COMPOSITIONS AND METHODS FOR OPTIMIZING DRUG HYDROPHOBICITY AND DRUG DELIVERY TO CELLS

RELATED APPLICATIONS

This application claims priority to U.S. Provisional Application 61/185,405 filed on Jun. 9, 2009, and U.S. Provisional Application 61/316,173 filed on Mar. 22, 2010, which are incorporated herein by reference in its entirety.

FIELD OF THE INVENTION

The invention relates generally to the fields of molecular biophysics, chemistry and immunology. More particularly, the invention relates to compositions and methods for optimizing drug efficacy, drug delivery by means of nanoparticles, and targeting drug-laden nanoparticles to diseased (e.g., carcinogenic) or pathogenic cells in a subject.

BACKGROUND

Multidrug resistance is a significant problem in the pharmaceutical industry, and may be achieved by the activation of cellular membrane transporters. Drugs and certain proteins are transported across the membranes of Gram-negative bacteria, for example, by energy-activated pumps. The outer membrane component of these pumps is a channel that opens from a sealed resting state during the transport process. ABCB1 exporter proteins confer drug resistance by pumping the drug out of the cell before the drug can function or exert its intended effect (e.g., kill a cancer cell). Classical inhibitors of the ABC exporter proteins are bulky hydrophobic molecules that overload the capacity of the hydrolysis of two ATP molecules to expel the drug by disruption of the hydrophobic associations, but these inhibitors lack specificity and are associated with significant side effects, disrupting important functions of ABC function in tissues throughout the body.

Methods for designing drugs and other therapeutic agents that are able to frustrate the activity of cellular exporter proteins and prevent expulsion of the drug or other therapeutic agent from a cell are greatly needed.

SUMMARY

Described herein is a method to determine drug hydrophobicity and to quantify changes in drug hydrophobicity that optimize drug function by means of differential scanning calorimetry of an endothermic phase transition of a base protein-based polymer, specifically of an elastic-contractile model protein, to which is attached the drug to be evaluated for its hydrophobicity in terms of the change in Gibbs free energy for hydrophobic association, $\Delta G_{HA}$. Also described herein is the preparation of nanoparticles comprised of protein-based polymers, specifically of elastic-contractile model proteins, designed for the binding and desired release rate of a specific drug or class of drugs. Further described herein is a means of targeting the drug-laden nanoparticle to a cell by means of decorating the nanoparticle surface with a molecular entity that selectively binds to the diseased cell or disease causing organism, e.g., by decorating the drug-laden nanoparticle surface with synthetic antigen-binding fragment to an up-regulated receptor characteristic of the diseased cell.

ABC exporter proteins contain two subunits related by a two-fold symmetry axis and comprised of three parts: the globular nucleotide binding domain (NBD) also called the catalytic head, a neck region at the upper reaches of which is a hydrophobic gate, and a transmembrane domain comprised of twelve α-helices, six helices from each subunit. The catalytic head contains two ATP molecules contributing to the association of the two components of the globular head and enclosing an aqueous/polar chamber overlying the hydrophobic gate. The γ-phosphate of the triphosphate, which arches over at the top of the aqueous/polar chamber and resides about 30 Å above the hydrophobic gate. The substrate binding site resides approximately centered within the transmembrane helices some 70 Å below the γ-phosphate and some 40 Å below the hydrophobic gate. The hydrolysis of a single molecule of ATP results in no transport; the simultaneous hydrolysis of both molecules of ATP is required to achieve transport of a single molecule of substrate. In our view the some 15 kcal/mol of energy released on hydrolysis two ATP molecules arises from the increased hydration of the more polar 2ADP plus 2P$_i$ (inorganic phosphate). The required hydration comes on opening (dissociation) of the hydrophobic gate some 30 Å below the 2 adenosine diphosphates and 2 inorganic phosphates. The specific molecular details of the opening involve the nature of hydrophobic hydration and entails knowledge of the thermodynamics of protein hydration, specifically the hydration of charged and hydrophobic moieties of the protein.

$\Delta G_{HA}$, the change in free energy of hydrophobic hydration derives from differential scanning calorimetry (DSC) data and gives rise in Table 1 to a Hydrophobicity Scale for amino acid side chains in both charged and uncharged states, and in Table 2 for prosthetic groups, for example, the redox couples for oxidized and reduced states of NAD (nicotinamide adenine dinucleotide), of FAD (flavin adenine dinucleotide), and so on, and for drugs that may be considered for frustrating the export capacity of ABC exporter proteins. Determination of $\Delta G_{HA}$ is described herein.

TABLE 1

Hydrophobicity Scale for amino acid residues in terms of $\Delta G°_{HA}$, the change is Gibbs free energy of hydrophobic association.

| Residue χ | $T_t$ ° C. | $\Delta G°_{HA}$(GχGVP) (SEQ ID NO: 2) kcal/mol-pentamer |
|---|---|---|
| W: Trp | −105 | −7.00 |
| F: Phe | −45 | −6.15 |
| Y: Tyr | −75 | −5.85 |
| H°: His° | −10 ($T_t$) | −4.80 (from graph) |
| L: Leu | 5 | −4.05 |
| I: Ile | 10 | −3.65 |
| V: Val | 26 | −2.50 |
| M: Met | 15 | −1.50 |
| H+: His+ | 30 ($T_t$) | −1.90 (from graph) |
| C: Cys | 30 ($T_t$) | −1.90 (from graph) |
| E°: Glu(COOH) | 20 (2) | −1.30 (−1.50) |
| P: Pro | 40 | −1.10 |
| A: Ala | 50 | −0.75 |
| T: Thr | 60 | −0.60 |
| D°: Asp(COOH) | 40 | −0.40 |

TABLE 1-continued

Hydrophobicity Scale for amino acid residues in terms of $\Delta G°_{HA}$, the change is Gibbs free energy of hydrophobic association.

| Residue $\chi$ | $T_t$ ° C. | $\Delta G°_{HA}$(G$\chi$GVP)<br>(SEQ ID NO: 2)<br>kcal/mol-pentamer |
|---|---|---|
| K°: Lys(NH$_2$) | 40 (38) | −0.05 (−0.60) |
| N: Asn | 50 | −0.05 |
| G: Gly | 55 | −0.00 |
| S: Ser | 60 | +0.55 |
| R: Arg | 60 ($T_t$) | +0.80 (from graph) |
| Q: Gln | 70 | +0.75 |
| Y−: Tyr($\phi$-O−) | 140 | +1.95 |
| D−: Asp(COO−) | 170 ($T_t$) | ≈ +3.4 (from graph) |
| K+: Lys(NH$_3$+) | (104) | (+2.94) |
| E−: Glu(COO−) | (218) | (+3.72) |
| Ser (PO$_4^{-2}$) | 860 ($T_t$) | ≈ +8.0 (from graph) |

Data within parentheses utilized microbial preparations of poly (30 mers), e.g., (GVGVP GVGVP G$\chi$GVP GVGVP GVGVP GVGVP)n (SEQ ID NO: 1), with n ≈ 40. The notation (from graph) indicates that the value of $T_t$ was used to obtain $\Delta G°_{HA}$(G$\chi$GVP) (SEQ ID NO: 2) from the experimental sigmoid curve of $T_t$ versus $\Delta G°_{HA}$. Adapted from Table 5.3 of Urry DW. What sustains life? Consilient mechanisms for protein-based machines and materials. Springer (Birkhauser), LLC, New York, ISBN: 08176 4346 X. 2006.

TABLE 2

Hydrophobicity Scale (preliminary $T_t$ and $\Delta G°_{HA}$ values) for Chemical Modifications and Prosthetic Groups of Proteins$^a$
$T_t$ = Temperature of Inverse Temperature Transition for poly[f$_v$(VPGVG), f$_x$(VPGXG)] (SEQ ID NO: 15)

| Residue X | $\Delta G°_{HA}$<br>from FIG. 13<br>(kcal/mol)$^g$ | $T_t$ linearly<br>extrapolated to<br>$f_x$ = 1 |
|---|---|---|
| Lys (dihydro NMeN)$^{b,d}$ | −7.0 | −130° C. |
| Glu(NADH)$^c$ | −5.5 | −30° C. |
| Lys (6-OH tetrahydro NMeN)$^{b,d}$ | −3.5 | 15° C. |
| Glu(FADH$_2$) | −2.5 | 25° C. |
| Glu(AMP) | +1.0 | 70° C. |
| Ser(-O-SO$_3$H) | +1.5 | 80° C. |
| Thr(-O-SO$_3$H) | +2.0 | 100° C. |
| Glu(NAD)$^c$ | +2.5 | 120° C. |
| Lys(NMeN, oxidized)$^{b,d}$ | +2.5 | 120° C. |
| Glu(FAD) | +2.5 | 120° C. |
| Tyr(-O-SO$_3$H)$^e$ | +3.0 | 140° C. |
| Tyr(-O-NO$_2^-$)$^f$ | +3.5 | 220° C. |
| Ser(PO$_4^-$) | +8.0 | 860° C. |

$^a$The usual conditions are for 40 mg/ml polymer, 0.15N NaCl and 0.01M phosphate at pH 7.4.
$^b$NMeN is for N-methyl nicotinamide pendant on a lysyl side chain, i.e., N-methyl-nicotinate attached by amide linkage to the ε-NH$_2$ of Lys and the most hydrophobic reduced state is N-methyl-1,6-dihydronicotinamide (dihydro NMeN), and the second reduced state is N-methyl-6-OH 1,4,5,6-tetrahydronicotinamide or (6-OH tetrahydro NMeN).
$^c$For the oxidized and reduced nicotinamide adenine dinucleotides, the conditions were 2.5 mg/ml polymer, 0.2M sodium bicarbonate buffer at pH 9.2.
$^d$For the oxidized and reduced N-methyl nicotinamide, the conditions were 5.0 mg/ml polymer, 0.1M potassium bicarbonate buffer at pH 9.5, 0.1M potassium chloride.
$^e$The pK$_a$ of polymer bound -O-SO$_3$H is 8.2.
$^f$The pK$_a$ of Tyr(-O-NO$_2$) is 7.2.
$^g$Gross estimates (e.g., ± 0.5 kcal/mol) of $\Delta G°_{HA}$ using the $T_t$-values in the right column in combination with the $T_{b(t)}$ versus $\Delta G°_{HA}$ values from FIG. 13. Adapted from Table 5.2 of reference Urry DW. What sustains life? Consilient mechanisms for protein-based machines and materials. Springer (Birkhauser), LLC, New York, ISBN: 08176 4346 X. 2006.

$\Delta G_{ap}$, the apolar-polar repulsive free energy for hydration that arises from the counterintuitive competition for hydration between apolar (hydrophobic) and polar (e.g., charged) species. The understanding of $\Delta G_{ap}$ arises from characterization by acid/base and redox titrimetry of the free energy conversions of which designed elastic-contractile model proteins (ECMPs) are capable, for example, visual demonstration of chemical energy producing mechanical work, i.e., chemo-mechanical transduction, and demonstrations of electrical energy producing mechanical work, i.e., electro-mechanical transduction, that is the "pumping of iron," the lifting and lowering of weights.

The initial insight into competition for hydration between apolar and polar groups comes from the 1937 study of Butler of the water solubility of a series of linear alcohols from methanol to n-pentanol. The Gibbs free energy for solubility is stated, $\Delta G(\text{dissolution}) = \Delta H - T\Delta S$, where $\Delta H/CH_2 = -1.5$ kcal/mol and $[-T\Delta S]/CH_2 = +1.7$ kcal/mol. This means that hydration of oil-like hydrophobic groups is exothermic, i.e., hydration of oil-like groups is a favorable reaction. Why then is n-octanol with seven $CH_2$ groups, instead of the four $CH_2$ groups of n-pentanol, insoluble in water. It is because the $[-T\Delta S]$ term grows positive faster than the $\Delta H$ term grows negative with each addition of a $CH_2$ group, such that by n-octanol the $[-T\Delta S]$ term is more positive than the $\Delta H$ term is negative. The result is a positive $\Delta G(\text{dissolution})$, which results in insolubility.

The design and determination of the hydrophobicity of drugs with which to frustrate ABC exporter proteins in their capacity to confer multi-drug resistance is described herein. In the methods, the hydrophobicity of drugs, such as the Oxaliplatin, Cisplatin, and Carboplatin series, is increased in a step-wise manner to determine the exact hydrophobicity of the hydrophobically modified drug by placing the series in a Hydrophobicity Scale for the drugs, and the series is tested for their effectiveness in decreasing the rate of export by an appropriate assay system of the appropriate ABC exporter protein. The methods identify a drug hydrophobicity that is sufficient to frustrate export, while not significantly interfering with the drug efficacy.

The hydrophobicity scale described herein provides an exact measure of the maximal hydrophobicity of the drug. The methodology determines the hydrophobicity by attachment to a suitable ECMP and determines the DSC of the phase transition. The heat of the transition ($\Delta H_t$) at the transition equals $T_t \Delta S_t$. The value obtained is a maximal value because at a temperature below the transition all groups are fully hydrated, the structure is a largely disordered coiled coil, and on phase separation essentially all of the hydrophobic hydration is lost as the hydrophobic groups associate.

Table 1 provides values of $\Delta G°_{HA}$, the change in Gibbs free energy for hydrophobic association, TABLE 3-continued Comparison of increases in Hydrophobicity on pKa and Reduction Potential Shifts and on Positive Cooperativity for different Functional Groups in the Basis Set:

Model protein iii: [GVGVP GVGVP GΦGVP GVGVP GVGFP GFGFP]n(GVGVP);
(SEQ ID NO: 18)
Φ/3F Model protein iv: [GVGVP GVGFP GΦGFP GVGVP GVGFP GVGFP]n(GVGVP);
(SEQ ID NO: 19)
Φ/4F Model protein v: [GVGVP GVGFP GΦGFP GVGVP GVGFP GFGFP]n(GVGVP);
(SEQ ID NO: 20)
Φ/5F

| Φ(function) | E(glutamic acid, —COOH) | | K(lysine amino, —NH$_2$) | | K{NMeN}- (redox) | |
|---|---|---|---|---|---|---|
| Energy term kcal/mol | $\Delta G_{ap}$§ (pKa shift) | $(\partial \Delta G/\partial \alpha)$ slope; (n) | $\Delta G_{ap}$ (pKa shift) | $(\partial \Delta G/\partial \alpha)$ slope; (n)† | zFΔE redox shift | $(\partial \Delta G/\partial \alpha')$ slope; (n)* |
| Φ/0F | 0.7 | 1.1 (1.5) | 0 | 0 (0.9) | 0 | 0 (1.0) |
| Φ/2F | 1.0 | 1.3 (1.6) | 0.3 | 0.3 (1.1) | 0.8 | 0.5 (1.2) |
| Φ/3F | 1.6 | 1.7 (1.9) | 0.6 | 0.7 (1.2) | 1.7 | 1.1 (1.5) |
| Φ/4F | 2.2 | 2.2 (2.7) | 1.4 | 1.2 (2.1) | 2.5 | 2.7 (4.8) |
| Φ/5F | 3.1 | 3.0 (8.0) | 2.0 | 2.1 (2.7) | — | — |

The numbers in parentheses in the table are the Hill coefficients, n, and Hill plots of $\log[\alpha/(1-\alpha)]$ versus pH for acid base titrations and $\log[\alpha'/(1-\alpha')]$ versus ΔE for the redox titrations are used, respectively, to calculate $(\partial \Delta G/\partial \alpha)$ and $(\partial \Delta G/\partial \alpha')$. $\partial \alpha$ and $\partial \alpha'$ are determined by graphical means using the y-axis intercept values of $\log[\alpha/(1-\alpha)] = 1$ ($\alpha = 0.91$) and $-1$ ($\alpha = 0.9$), giving the graphically derived values of the divisors of 0.82 (= 0.91 − 0.09) for both $\Delta\alpha$ and $\Delta\alpha'$. The corresponding x-axis reference values are a ΔpH of 2 with ΔG = −2.3 RTΔpH for the acid-base titrations and a ΔE of 59 mV with ΔG = −zFΔE for the redox titrations. As defined in FIG. 15, the expressions for acid base titrations become $(\partial \Delta G/\partial \alpha) = -2.3RT(\Delta pH^{exptl} - \Delta pH^{ref})/0.82$ with $\Delta pH^{ref} = 2$ and $\Delta pH^{exptl}$ being the run corresponding to the $\Delta\alpha = 0.82$ rise for a readily defined interval of the Hill plot (See section 4.4.5). Analogously for redox titrations, $(\partial \Delta G/\partial \alpha') = -zF(\Delta E^{exptl} - \Delta E^{ref})/0.82$ with $\Delta E^{ref} = 59$ mV and $\Delta E^{exptl}$ being the run corresponding to the rise of $\Delta\alpha' = 0.82$ for the specified interval. As $\Delta pH^{exptl}$ approaches 2 and as $\Delta E^{exptl}$ approaches 59, the slope approaches one and the terms $(\partial \Delta G/\partial \alpha)$ and $(\partial \Delta G/\partial \alpha')$ approach zero, which is n = 1. The sign on the free energies is written as the repulsive free energy, $\Delta G_{ap}$, in which an increase in hydrophobicity increases the free energy on going from the less polar to the more polar state, i.e., to the charged or the oxidized state. This results from an increase in ΔG due to the increase in apolar-polar repulsion.
§The pKa for the unperturbed glutamic acid is taken as 4.0.
†The Hill coefficient, n, for K/0F was experimentally found to be 0.9, possibly due to the effect of Cl⁻—NH$_3$⁺ ion pair formation during the titration. Since the interest is the change due to addition of more hydrophobic Phe (F) residues, K/0F is taken as the reference state [16
*The Hill coefficient, n, for the reference state composition, K{NMeN}/0F, i.e., N-methyl nicotinamide (NMeN) attached by amide linkage to lysine (K) of Model protein i, is taken as 1.0 after including the term, 1/z of 2.3RT/zF, for the number of electrons (2) transferred in the overall reaction (See Eqn. 18). Adapted from Table 2F of Urry DW. Luan C-H. Elastic, Plastic, and Hydrogel Protein-based Polymers. Polymer Data Handbook Second Edition, (Edited by James. E. Mark), Oxford University Press, New York, NY 2009, pages 121-137.

Accordingly, described herein is a method of producing a therapeutic drug for treating or preventing a disease or condition that is capable of down-regulating exporter protein activity in a cell. The method includes the steps of: providing a drug that is used for treating or preventing the disease or condition or that is a candidate drug for treating or preventing the disease or condition; modifying the drug to increase hydrophobicity of the drug, resulting in at least a first modified drug having a hydrophobicity higher than that of the drug; modifying the drug or the at least first modified drug to increase hydrophobicity of the drug or the at least first modified drug, resulting in at least a second modified drug having a hydrophobicity higher than that of the drug and that of the at least first modified drug; use a change in Gibbs free energy for hydrophobic association-based hydrophobicity scale to determine the hydrophobicities of the drug, the at least first modified drug, and the at least second modified drug; testing the drug, the at least first modified drug and at least second modified drug for efficacy of treating or preventing the disease or condition, and assigning a value for efficacy for each of the drug, at least first modified drug and at least second modified drug; testing the drug, the at least first modified drug and at least second modified drug for a capacity to decrease a rate of export of the drug, the at least first modified drug and at least second modified drug from a cell, and assigning a value for the decreased rate of export for each of the drug, at least first modified drug and at least second modified drug; and for each of the drug, the at least first modified drug and at least second modified drug, determining a ratio of the value for efficacy to the value for the decreased rate of export, wherein one of selected from the group consisting of: the drug, the at least one modified drug, and the at least second modified drug having the highest ratio of value for efficacy to the value for the decreased rate of export is identified as a therapeutic drug for treatment or prevention of the disease or condition.

In the method, the step of determining a ratio of the value for efficacy to the value for the decreased rate of export, wherein one of selected from the group consisting of: the drug, the at least one modified drug, and the at least second modified drug having the highest ratio of value for efficacy to the value for the decreased rate of export is identified as a therapeutic drug for treatment or prevention of the disease or condition can include identifying an optimal hydrophobicity for down-regulating exporter protein activity in the cell. In some embodiments, at least a third modified drug (e.g., at least a third and at least a fourth) is produced by and tested according to the steps of the method. Typically, the therapeutic drug when administered to a cell decreases or prevents disruption of hydrophobic associations required for opening of at least one transmembrane channel within at least one exporter protein in the cell, the at least one exporter protein activity conferring drug resistance to the cell. The therapeutic drug can have a hydrophobicity in the range of about −2 kcal/mole to about −20 kcal/mole. In one embodiment, the cell is a *Staphylococcus aureus* cell, and the at least one exporter protein is Sav1866. In another embodiment, the cell is a *Salmonella typhimurium* cell and the at least one exporter protein is MsbA. In yet another embodiment, the cell is a mammalian cell and the at least one exporter protein is a P-glycoprotein.

In the method, down-regulating exporter protein activity includes reducing or preventing disruption of a hydrophobic association by simultaneous hydrolysis of two ATP molecules required for exporter protein activity in the cell. The disease or condition can be cancer or infection by a pathogen, as examples. Increasing hydrophobicity can include at least one of: adding one or more aliphatic groups, adding one or more aromatic groups, adding one or more heteroaromatic groups, and adding one or more of a combination thereof. For example, increasing hydrophobicity includes at least one of: adding one or more methyl groups, adding one or more ethyl groups, adding one or more ethylene groups, adding one or more propyl groups, adding one or more propylene groups, adding one or more isopropyl groups, adding one or more isobutyl groups, adding one or more t-butyl groups, adding one or more cyclobutyl groups, adding one or more cyclopentyl groups, adding one or more cyclohexyl groups, adding one or more phenyl groups, adding one or more purine or pyrimidine group(s), adding one or more nicotinamide, and adding one or more flavinoid groups.

Also described herein is a a composition including a therapeutic drug produced by the method of providing a drug that is used for treating or preventing the disease or condition or that is a candidate drug for treating or preventing the disease or condition; modifying the drug to increase hydrophobicity of the drug, resulting in at least a first modified drug having a hydrophobicity higher than that of the drug; modifying the drug or the at least first modified drug to increase hydrophobicity of the drug or the at least first modified drug, resulting in at least a second modified drug having a hydrophobicity higher than that of the drug and that of the at least first modified drug; use a change in Gibbs free energy for hydrophobic association-based hydrophobicity scale to determine the hydrophobicities of the drug, the at least first modified drug, and the at least second modified drug; testing the drug, the at least first modified drug and at least second modified drug for efficacy of treating or preventing the disease or condition, and assigning a value for efficacy for each of the drug, at least first modified drug and at least second modified drug; testing the drug, the at least first modified drug and at least second modified drug for a capacity to decrease a rate of export of the drug, the at least first modified drug and at least second modified drug from a cell, and assigning a value for the decreased rate of export for each of the drug, at least first modified drug and at least second modified drug; and for each of the drug, the at least first modified drug and at least second modified drug, determining a ratio of the value for efficacy to the value for the decreased rate of export, wherein one of selected from the group consisting of: the drug, the at least one modified drug, and the at least second modified drug having the highest ratio of value for efficacy to the value for the decreased rate of export is identified as a therapeutic drug for treatment or prevention of the disease or condition.

The therapeutic drug typically has a hydrophobicity of about −2 kcal/mole to about −20 kcal/mole, the drug being capable of reducing or preventing export of the drug from a cell by exporter proteins. The therapeutic drug is present at a concentration sufficient for decreasing or preventing disruption of hydrophobic associations required for opening of at least one transmembrane channel within at least one exporter protein in the cell. In one embodiment, the cell is a *Staphylococcus aureus* cell, and the at least one exporter protein is Sav1866. In another embodiment, the cell is a *Salmonella typhimurium* cell and the at least one exporter protein is MsbA. In a further embodiment, the cell is a mammalian cell and the at least one exporter protein is a P-glycoprotein. The therapeutic drug can be used to treat or prevent cancer or infection by a pathogen, as examples.

By the term "conjugated" is meant when one molecule or agent is physically or chemically coupled or adhered to another molecule or agent. Examples of conjugation include covalent linkage and electrostatic complexation. The terms "complexed," "complexed with," and "conjugated" are used interchangeably herein.

As used herein, the term "nanoparticle" means a microscopic particle whose size is measured in nanometers and that is composed of protein-based polymers, or more specifically ECMP comprised of repeating pentapeptides. For example, an electron micrograph of a particular ECMP nanoparticle is shown in FIG. 24 below and its composition is given in the associated figure legend.

As used herein, the terms "displayed" or "surface exposed or decorated" are considered to be synonyms, and refer to antigens, epitopes, antigen-binding fragments, or other molecules that are present at the external surface of a structure such as a nanoparticle.

By the term "multivalent" is meant that more than one copy or type of antigen or molecule is displayed on a nanoparticle.

By the phrases "therapeutically effective amount" and "effective dosage" is meant an amount sufficient to produce a therapeutically (e.g., clinically) desirable result; the exact nature of the result will vary depending on the nature of the disorder being treated. For example, where the disorder to be treated is cancer, the result can be elimination of cancerous cells including cancerous tumors. The compositions described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient," "subject" and "individual" are used interchangeably herein, and mean a mammalian subject to be treated, with human patients being preferred. In some cases, the methods of the invention find use in experimental animals, in veterinary applications, and in the development of animal models for disease, including, but not limited to, rodents including mice, rats, and hamsters, as well as non-human primates.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 part 2 shows a means for developing the $T_t$-based and $\Delta G_{HA}$-based Hydrophobicity Scales for amino acid residues. D. Dependence of $T_t$ on Amino Acid Composition for poly[f$_V$(GVGVP),f$_X$(GXGVP)] (SEQ ID NO:5) where f$_X$=0.2. E. Using the composition of the First EMCP Basis Set poly[f$_V$(GVGVP),f$_X$(GXGVP)], (SEQ ID NO:5), the value of $T_t$ or of $\Delta G_{HA}$=$\Delta H_t$(GVGVP) (SEQ ID NO:4)-$\Delta H_t$(GXGVP) (SEQ ID NO:2) in kcal/mol is plotted versus f$_X$, the mole fraction of pentamers containing the residue X. Extrapolation to f$_X$=1 gives the value of the temperature of inverse temperature transition, $T_t$, for poly(GXGVP) (SEQ ID NO:2) or of $\Delta G_{HA}$=$\Delta H_t$(GVGVP) (SEQ ID NO:4)-$\Delta H_t$(GXGVP) (SEQ ID NO:2) (kcal/mol).

FIG. 3 is a plot showing controlled release of positively charged Leu-enkephalin amide (H+-Tyr-Gly-Gly-Phe-Leu-NH$_2$, (SEQ ID NO:6), LEA+) using chemically-synthesized, negatively-charged polymers with designed increases in hydrophobicity giving ΔpKa values of 0.9, 1.3, and 2.2 and ΔGap values of 1.2, 1.8, and 3.0 kcal/mol-E, respectively. After burst release due to 50% excess drug over polymer sites, a constant surface area maintains zero order release levels per day continuing at 4.7 μmole for 25 days, 2.7 μmole for 30 days, and 1.9 μmole for 70 days, respectively. The amino acid sequences from top to bottom are: SEQ ID NO:12, SEQ ID NO:13 and SEQ ID NO:14.

Figure 1A:
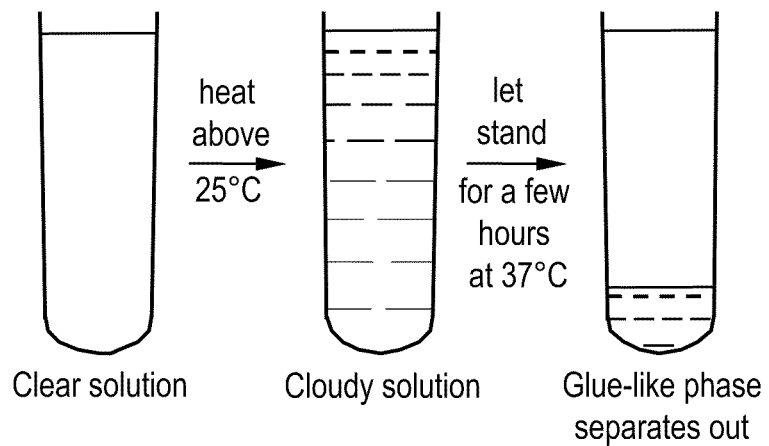
FIG. 1 part 1 is a schematic illustration and a pair of graphs showing characterization of an inverse temperature transition (ITT), which is a phase separation from aqueous solution due to hydrophobic association to form a more ordered viscoelastic phase. Tubes showing the phase separation as a function of temperature and time. (glycine-valine-glycine-valine-proline)$_{251}$ (SEQ ID NO:3) (or $\{GVGVP\}_{251}$) (SEQ ID NO:3) is completely water soluble below 25° C. As the temperature of the solution is raised above 25° C., the solution becomes cloudy with the temperature profile for turbidity formation shown in part B. On standing at 37° C. the cloudy solution phase separates to form a phase separated state of 63% water and 37% (GVGVP)$_n$ (SEQ ID NO:4) by weight. B. Determination of $T_t$, which indicates onset of aggregation. C. Differential scanning calorimetry showing the heat absorbing, endothermic, transition from which the heat of the transition, $\Delta H_t$, is determined. In part B, the amino acid sequence above the graph is SEQ ID NO:3.
Figure 1B:
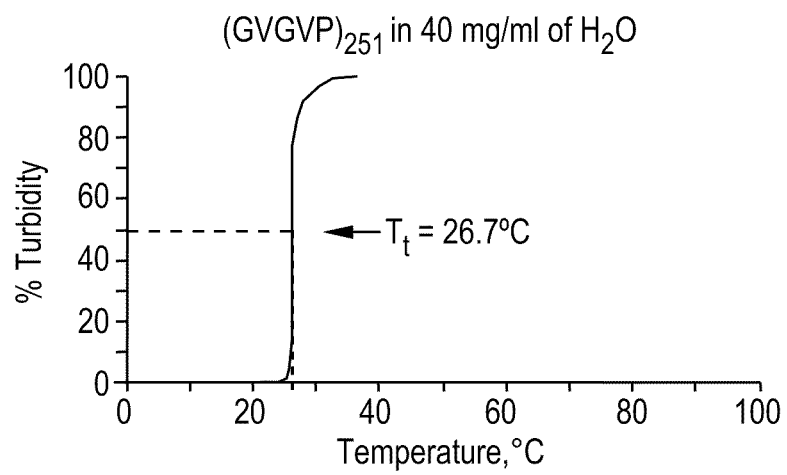
Figure 1C:
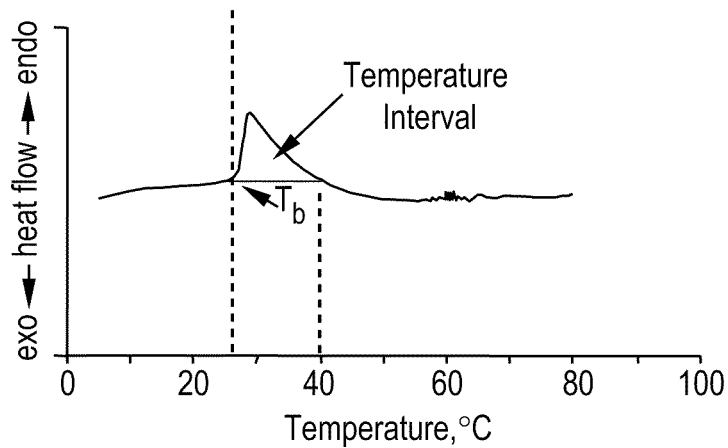
Figure 1D:
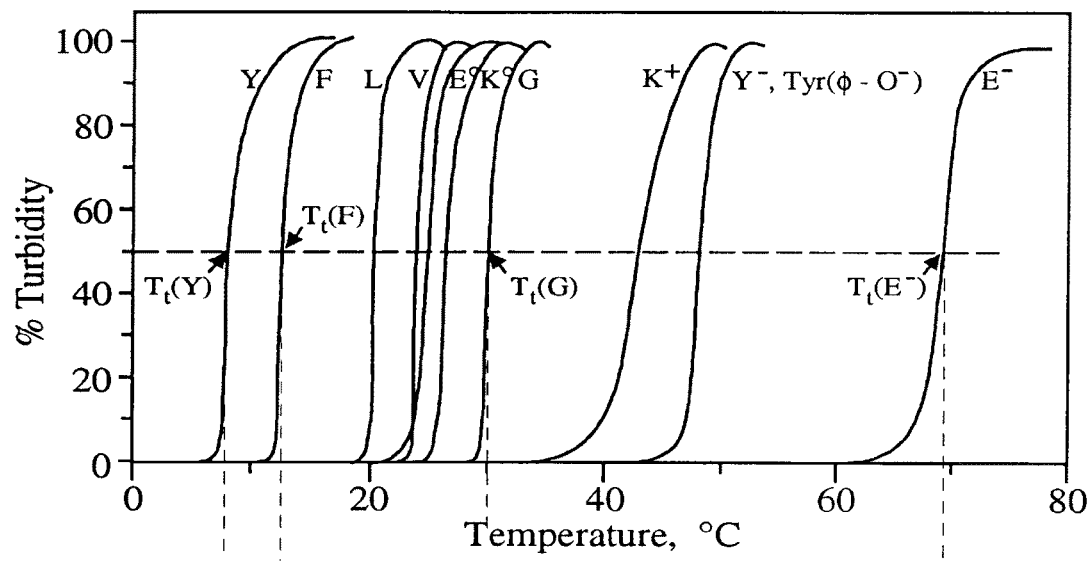

Fab1(chain A) and Fab2(chain B) in space-filling in gray code B. Fab1(chain A-graylight) and Fab2(chain B-dark) in space filling representation. Developed from the crystal structure of S. Uysal, V. Vásquez, V. Tereshko, K. Esaki, F. A. Fellouse, S. S. Sidhu, S. Koide, E. Peroz and A. Kossiakoff *Proc. Natl. Acad. Sci. USA,* 2009, 106, 6644-6649, obtained from the Protein Data Bank accession code 3EFF.Accession code Protein Data Bank 3EFF due to S. Uysal et al. (*Proc. Natl. Acad. Sci. USA,* 2009, 106, 6644-6649. Protein Data Bank accession code 3EFF).

DETAILED DESCRIPTION

Described herein is the development and use of a hydrophobicity scale based on the change in Gibbs free energy of hydrophobic association, methods of producing a therapeutic drug for treating or preventing a disease or condition that is capable of down-regulating exporter protein activity (responsible for drug resistance) in a cell based on the hydrophobicity scale, therapeutic drugs produced according to these methods, compositions including same, and nanoparticles for delivering a therapeutic drug as described herein. In these methods, the hydrophobicity of a drug or candidate drug is optimized, resulting in a drug that is able to decrease or prevent exporter protein activity in a cell and thus decrease or prevent export of the drug from the cell.

A nanoparticle as described herein is conjugated or bound to at least one molecule for targeting a particular cell type. The at least one molecule may be a protein or peptide of bacterial, fungal, protozoan, or viral origin, or a fragment derived from these antigens, a carbohydrate, or a carbohydrate mimetic peptide. A nanoparticle can be conjugated to two or more different molecules for targeting a particular cell type (e.g., two or more different cell-specific targeting molecules) The at least one molecule (i.e., surface exposed molecules) can be conjugated to or bound to a nanoparticle by any suitable means known in the art. For example, peptide or polypeptide antigens can be chemically linked to the nanoparticles or made contiguous with the model protein by recombinant DNA methodology. Conjugation methods include chemical complexation, which may be either ionic or non-ionic in nature, electrostatic binding, or covalent binding.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

Development of A change In Gibbs Free Energy For Hydrophobic Association-Based Hydrophobicity Scale Described herein is a hydrophobicity scale based on the change in Gibbs free energy of hydrophobic association. Increase in entropy of water drives endothermic phase transition of hydrophobic association. For a narrow phase transition the chemical potential, $\mu$, of the molecules in the phase separated, hydrophobically associated state, $\mu_{HA}$, and the solution, hydrophobically dissociated state, $\mu_{HD}$, are equal. Therefore, at constant temperature and pressure, i.e., at equilibrium, the change in Gibbs free energy for the phase transition is zero, $(\Delta G_t)_{TP}=0$ and $\Delta H_t=T_t\Delta S_t$. For the breadth of the transition of elastic-contractile model proteins [ECMP], it is written:

$$\Delta H_t \approx T_t \Delta S_t, \quad (1)$$

i.e., the heat of the transition, $\Delta H_t$ in kcal/mol, is approximated by the product of the temperature of the transition, $T_t$ in °K, times the entropy change attending the transition, $\Delta S_t$ in kcal/° K-mol.

As the phase transition for $(GVGVP)_n$ (SEQ ID NO:4) is endothermic, $\Delta H_t$ is positive, and therefore by Eqn. (1), $\Delta S_t$ is positive. Since the endothermic phase transition that occurs on raising the temperature is of a two-component system (water plus model protein), $$\Delta S_t(\text{total system})=[\Delta S_t(\text{model protein})+\Delta S_t(\text{water})]>0. \quad (2)$$

Eqn. (2) is a statement of the 2nd law of thermodynamics that the entropy of the total system must increase with temperature, that is, $\Delta S_t$(total system) is positive. But since the model protein goes to a more dense, lower entropy state and even a structured state, $\Delta S_t$(model protein) is negative. Yet $$\Delta S_t(\text{water})=[\Delta S_t(\text{total system})-\Delta S_t(\text{model protein})]>0, \quad (3)$$

and $$\Delta S_t(\text{water})>\Delta S_t(\text{total system}) \quad (4)$$

Since the model protein component increases in order (rather than decreases) on raising the temperature, this phase transition has been called an inverse temperature transition, and the total increase in entropy of water is greater yet than the magnitude obtained from the endothermic transition measured by differential scanning calorimetry. The increase in entropy of the water, as it goes from ordered hydrophobic hydration to bulk water, drives the entire inverse temperature transition exhibited by $(GVGVP)_n$ (SEQ ID NO:4) and, importantly, overwhelms the oppositely signed exothermic component, e.g., van der Waals interactions, and the decrease in entropy on self-assembly of the protein component. The endothermic inverse temperature transition is driven entirely by the increase in entropy of water, as structured hydrophobic hydration becomes less-ordered bulk water.

The van der Walls interaction is exothermic for the hydrophobic association attending the ITT, yet the ITT is endothermic. Thus, the van der Walls interaction does not provide the driving force for hydrophobic association. The derivation of the change in Gibbs free energy for hydrophobic association, $\Delta G_{HA}$, and evaluation by inverse temperature transition of hydrophobic association has been reported previously (D. W. Urry, The Change in Gibbs Free Energy for Hydrophobic Association: Derivation and Evaluation by means of Inverse Temperature Transitions. Chem. Phys. Letters 399 (2004) 177-183.), and is given more simply below. For sufficiently narrow phase transitions the enabling statement of Eqn (1) may be written for each of two different pentamer compositions, e.g., $$\Delta H_t(GVGVP) \text{ (SEQ ID NO: 4)} \approx T_t(GVGVP) \text{ (SEQ ID NO: 4)}$$
$$\Delta S_t(GVGVP) \text{ (SEQ ID NO: 4)} \quad (5)$$
and
$$\Delta H_t(G\chi GVP) \text{ (SEQ ID NO: 2)} \approx T_t(G\chi GVP) \text{ (SEQ ID NO: 2)}$$
$$\Delta S_t(G\chi GVP) \text{ (SEQ ID NO: 2)}$$

where χ represents the guest residue that has caused the change in $\Delta H_t$ and the GVGVP (SEQ ID NO:4) pentamer is the experimental reference state when going through the entire set of naturally occurring amino acid residues of a protein. Subtracting Eqn. (6) from Eqn. (5) gives $\Delta H_t$(GVGVP) (SEQ ID NO: 4) - $\Delta H_t$(GχGVP)

(SEQ ID NO: 2) ≈ $T_t$(GVGVP) (SEQ ID NO: 4)

$\Delta S_t$(GVGVP) (SEQ ID NO: 4) - $T_t$(GχGVP)

(SEQ ID NO: 2)$\Delta S_t$(GχGVP) (SEQ ID NO: 2) (7).

Given the above approximation, but also recognizing that $\Delta S_t$ is a calculated result from the differential scanning calorimetric measurement of $\Delta H_t$, we define the change in Gibbs free energy for hydrophobic association, $\Delta G_{HA}$, as, (8)   $\Delta G_{HA} \equiv \Delta H_t$(GVGVP) (SEQ ID NO: 4) - $\Delta H_t$(GχGVP),   (SEQ ID NO: 2)

recognizing that $\Delta H_t$ must be the heat of a transition where the approximation of Eqn. (1) obtains.

The differential scanning calorimetry (DSC) data of $\Delta H_t$ (GVGVP) (SEQ ID NO:4) and $\Delta H_t$(GVGIP) (SEQ ID NO:8) in FIG. 1 of Luan and Urry, J Phys Chem 95:7896-7900, 1991 provide a specific example of the difference that defines $\Delta G_{HA}$. In FIG. 1 the areas of the curves represent the endothermic heats and the difference in areas for the inverse temperature transition gives the change in Gibbs free energy for hydrophobic association, $\Delta G_{HA}$, a value of −1.5 kcal/mol-pentamer due to the addition of a single $CH_2$ to give (GVGIP) (SEQ ID NO:8). This is the same value of 1.5 kcal/mol-$CH_2$ for the addition of a single $CH_2$ as determined by Butler for the alcohol series.

Accordingly, $\Delta G_{HA}$ as defined is dominated by the endothermic transition of the conversion of hydrophobic hydration to bulk water, but it also includes a smaller exothermic component (Rodriguez-Cabello et al., Chem Phys Letters 388: 127-31, 2004), considered to be the release of heat due to van der Waals' interactions resulting from hydrophobic association. Thus, the favorable exothermic heat due to van der Waals' interaction, often considered to be the basis for the hydrophobic effect, in fact, is of the opposite sign to that of an endothermic inverse temperature transition that drives hydrophobic association. Importantly, $\Delta G_{HA}$ contains the contribution of van der Waals contacts and any other exothermic interactions that may accompany hydrophobic association, but, of course, $\Delta G_{HA}$ is dominated by the differences in the endothermic conversion of hydrophobic hydration to bulk water between the reference state (GVGVP) (SEQ ID NO:4) and (GVGIP) (SEQ ID NO:8) test state.

Cold denaturation of proteins, where lowering the temperature results in hydrophobic dissociation and formation of exothermic hydrophobic hydration, is the reverse process from raising the temperature to elicit an endothermic inverse temperature transition of hydrophobic association. Obviously, cold denaturation of proteins is driven by the exothermic formation of hydrophobic hydration and occurs with the endothermic loss, of the lesser energy consideration, of van der Waals contacts. Simply stated, the report of P. L. Privalov (Crit. Revs Biochem Mol Biol 25:281-305, 1990) shows the inverse temperature transition to be central to the protein subunit assembly of a long list of biology's proteins, as has been extensively shown by means of systematically designed elastic-contractile model proteins. Therefore, an understanding of $\Delta G_{HA}$ and $\Delta G_{ap}$, described below, become central to the design of protein-based polymers (and of amphiphilic polymers, in general) as biomaterials for use in the aqueous milieu of biology and of the function of the proteins of biology.

The following describes development of the $\Delta G_{HA}$-based Hydrophobicity Scale. Because the temperature of the inverse temperature transition for $(G_\chi GVP)_{n\sim200}$ (SEQ ID NO:9) may be outside of the experimentally accessible temperature range, either below 0° C. or above 80° C., and in order to utilize results for sparse, non-self-interacting substitutions, the statement of experimentally used pentamer composition may effectively be considered as poly[$f_\chi(G_\chi GVP)$, $f_V$(GVGVP)] (SEQ ID NO:10) where $f_\chi$ and $f_V$ are the mole fractions of pentamers in the polymer with $f_\chi+f_V=1$. As exemplified in FIG. 1E. The linear set of data points, for say $f_\chi=01$, 0.2, and 0.3 versus $\Delta H_t$, are linearly extrapolated to $f_\chi=1$. This allows proper comparison of the data for $f_\chi=1$ with $f_V=1$, which is the experimental reference value for $(GVGVP)_n$. (SEQ ID NO:4). The boldfaced $\Delta G_{HA}$, $\Delta H_t(G_\chi GVP)$, (SEQ ID NO:2), $\Delta H_t$(GVGVP), (SEQ ID NO:4), $T_t(G_\chi GVP)$ (SEQ ID NO:2) and $T_t$(GVGVP), (SEQ ID NO:4), signify that the values are for $f_\chi=1$ and $f_V=1$ whether obtained from homopolypentapeptides directly, or as necessary, on extrapolation to $f_\chi=1$ to obtain $\Delta H_t(G_\chi GVP)_{n\sim200}$ (SEQ ID NO:9) or $T_t(G_\chi GVP)$ (SEQ ID NO:2). For experimental values obtained on polymers with $f_\chi<1$, i.e., poly[$f_\chi(G_\chi GVP),f_V$ (GVGVP) (SEQ ID NO:10) representing the first ECMP basis set, $\Delta H_t$ would not be boldfaced and might be explicitly written for an ECMP composition of $f_\chi=0.2$ as $\Delta H_t$[0.2 $(G_\chi GVP)$ (SEQ ID NO:2),0.8(GVGVP) (SEQ ID NO:4)].

Figure 1E:
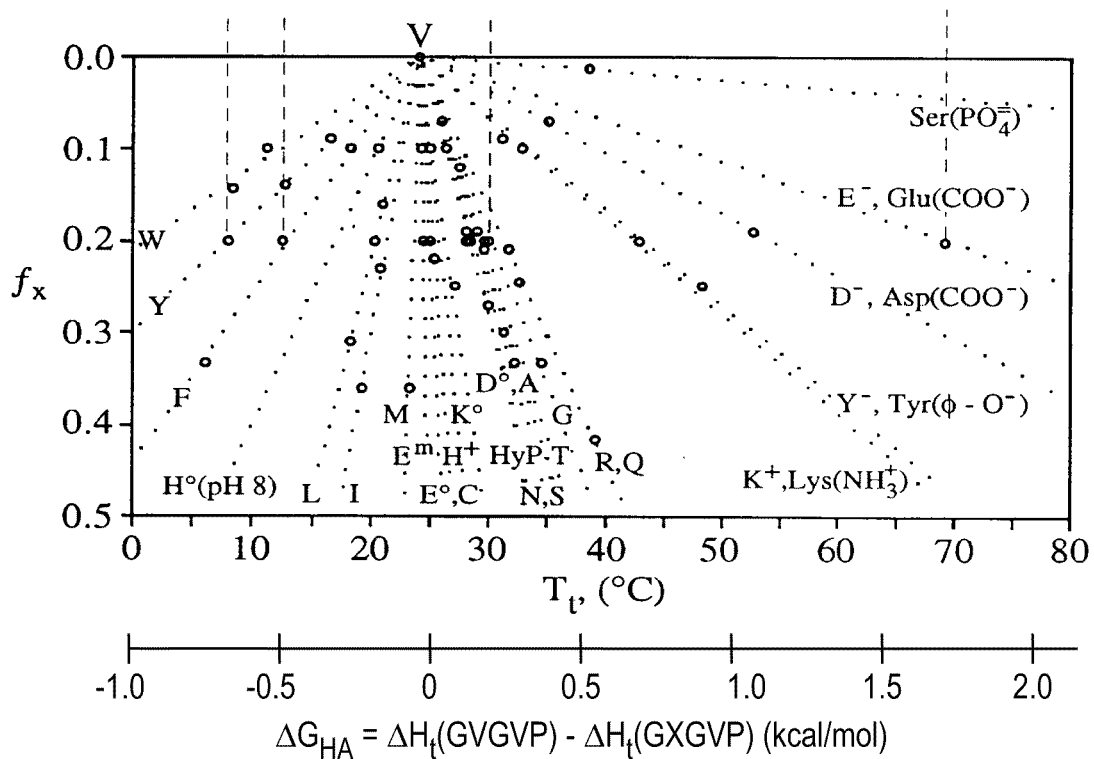
Figure 13:
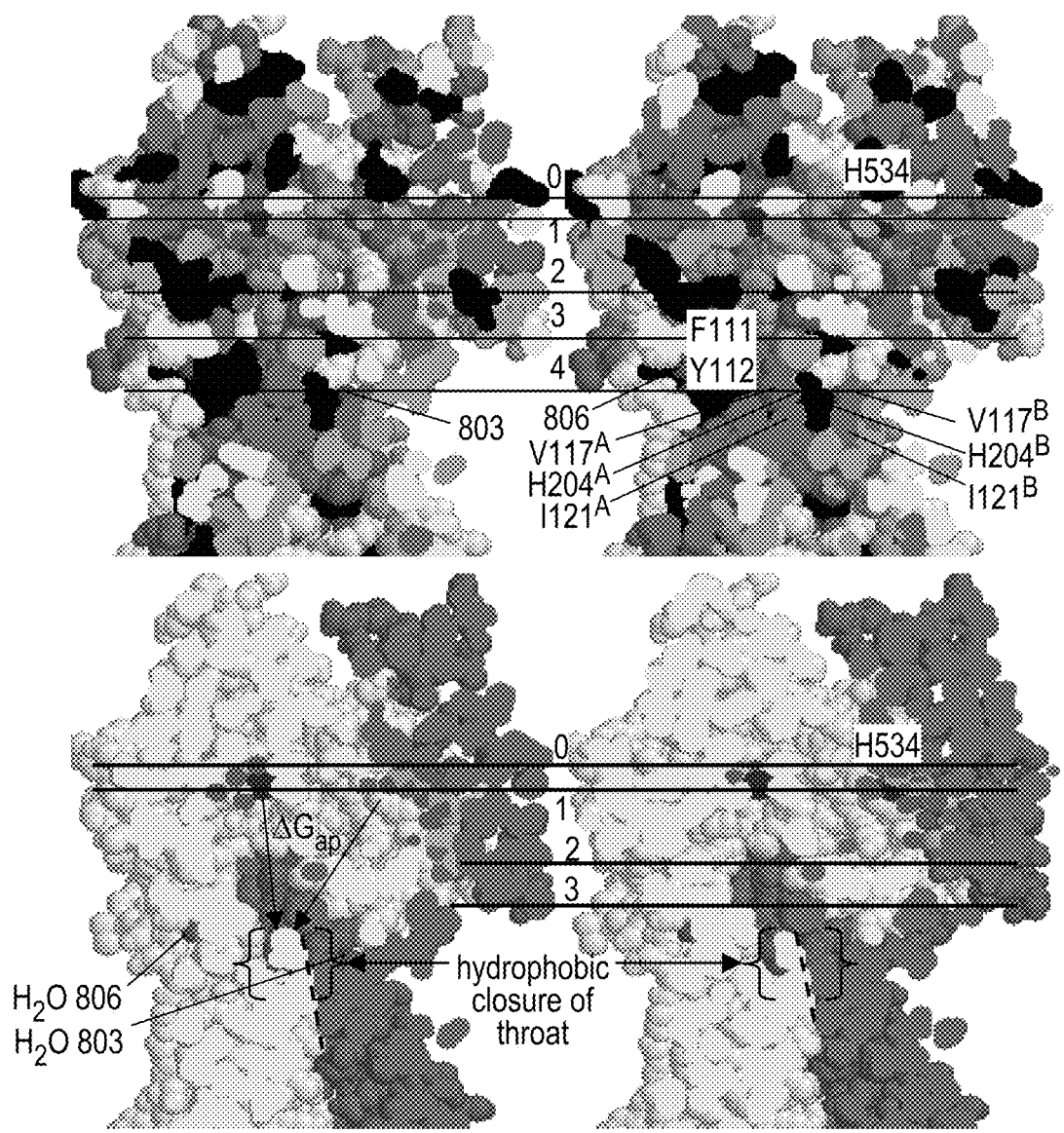
FIG. 13A is a cross-eye stereo view of vertical slab cut of Sav1866 near both NaPγ taken through the internal aqueous/polar chamber with horizontal lines for cross-sections that span the internal aqueous-polar chamber (from top at line 0, as in FIG. 13, to its base at upper side of line 4), which chamber is closed by hydrophobic association of residues Y112, V207, V117, H204 just below waters 806 and 816. When looking up from line 3 in FIG. 13 the two Na at the top of the chamber can yet be seen.
FIG. 13B. Same section as in A., but with the A chain white and the B chain gray. It is used to delineate the hydrophobic closure and approximate orientation of the $\Delta$Gap vectors on hydrolysis of the two ATP. Protein Data Bank accession code 2ONJ due to Dawson and Locher (Dawson R J P, Locher K P. FEBS Ltrs 2007; 581: 935-8. Protein Data Bank, Accession Code 2ONJ).
Figure 14:
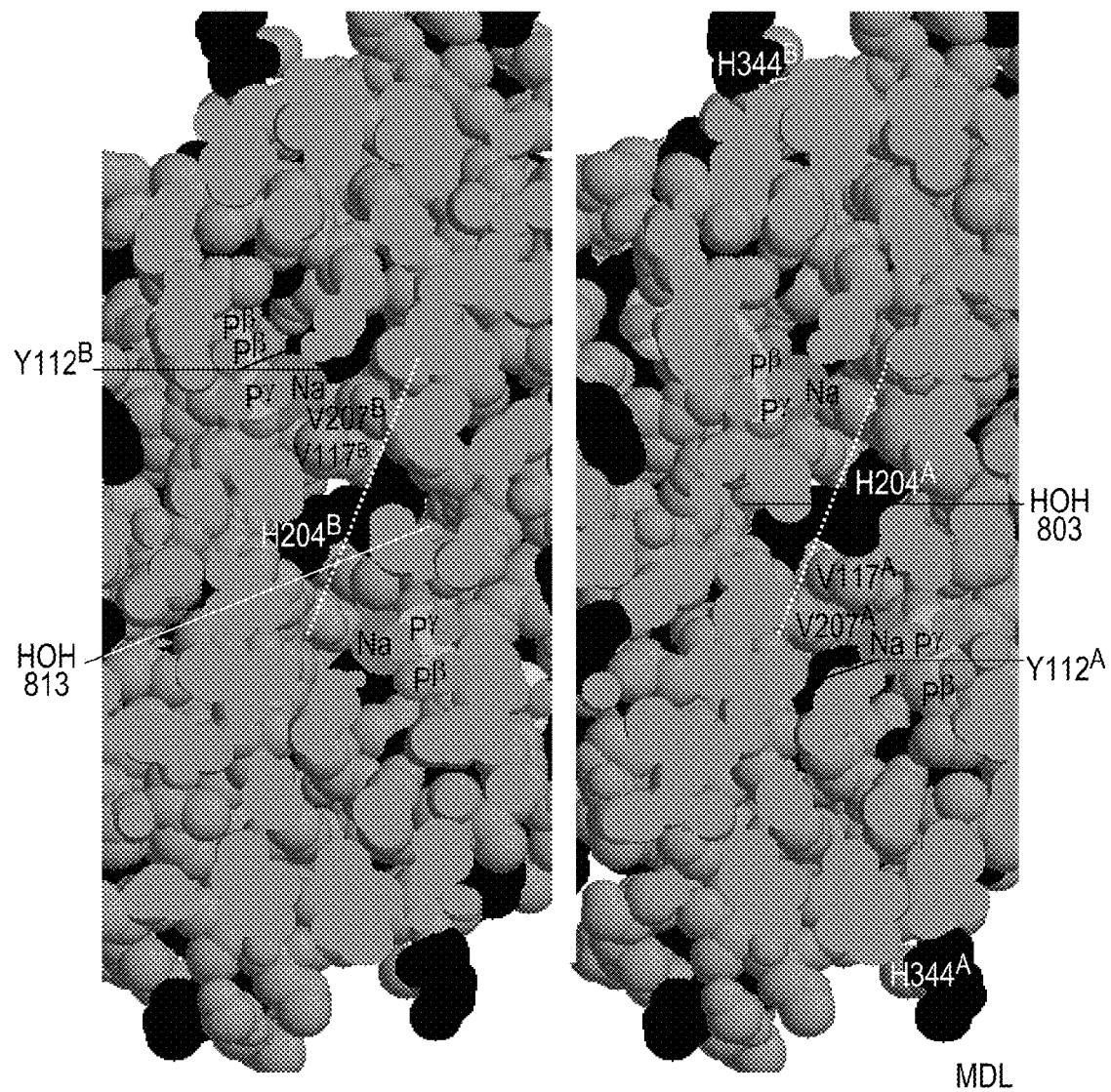
FIG. 14 is a cross-eye stereo view of dimeric ABC exporter, Sav1866, showing neutral aliphatic (gray) and aromatic (black) residues but with polar residues absent and shown in cross-section at a level just below H534 and above Pγ (line 0 FIG. 13) at the top of, and looking down into, the internal aqueous-polar chamber to its base made up by residues Y112$^{A\&B}$, V207$^{A\&B}$, V117$^{A\&B}$, and H204$^{A\&B}$, which are at the level of the hydrophobic closure of the channel that opens by apolar-polar repulsion on hydrolysis of 2ATP to 2ADP plus 2Pi. Dashed line approximates boundary between A and B chains. Protein Data Bank accession code 2ONJ due to Dawson and Locher (Dawson R J P, Locher K P. FEBS Ltrs 2007; 581: 935-8. Protein Data Bank, Accession Code 2ONJ).
Figure 15:
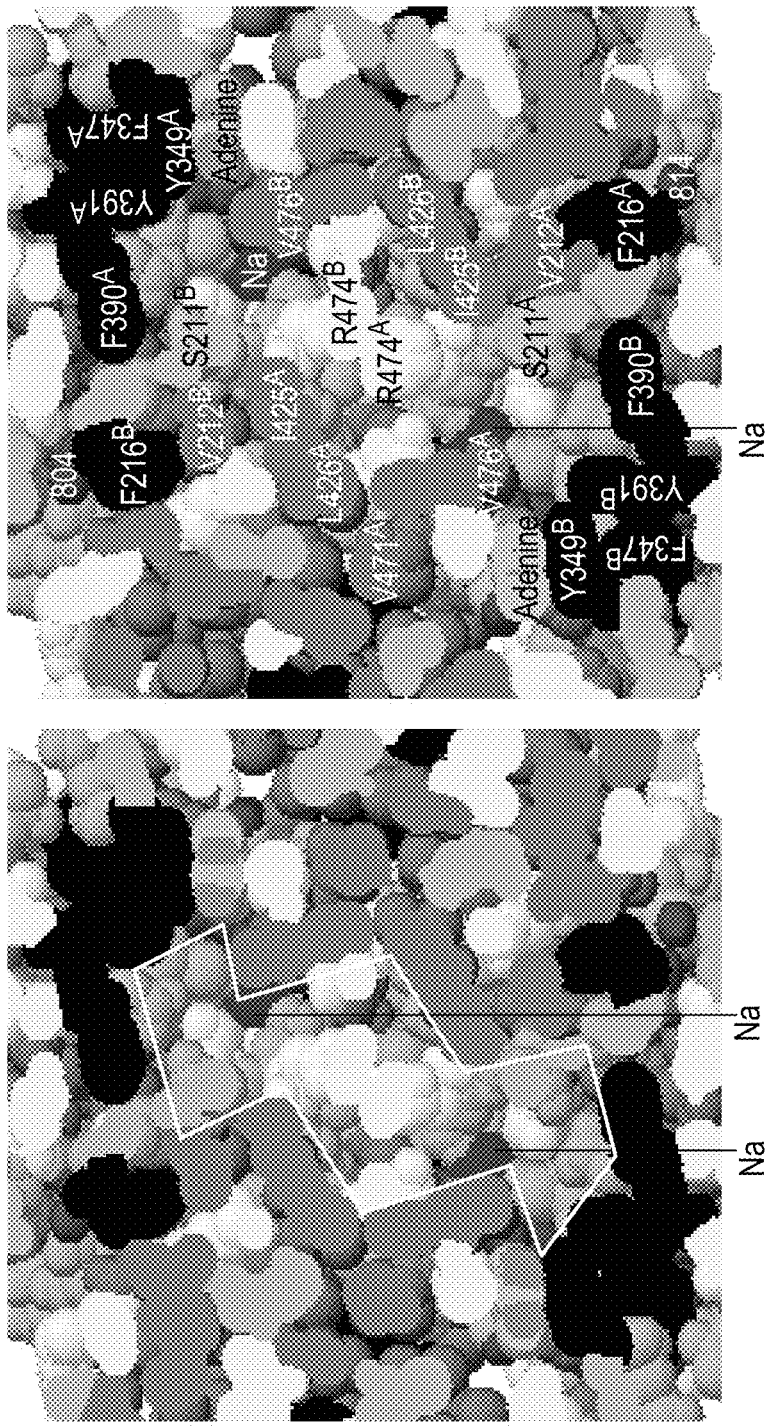
FIG. 15 is a horizontal cross-section of ABC exporter (Sav1866) at level 2 in FIG. 13 of cross-eye stereo view looking to top of internal aqueous chamber from base of nucleotide. Space filling representation with hydrophobic (gray), aromatic (black), neutral (light gray) charged (white) residues and water molecules and blue Na atoms bound to P$^\beta$ and P$^\gamma$ of ATP. On left is an outline of the aqueous chamber when looking up from level 2 in FIG. 13. Protein Data Bank accession code 2ONJ due to Dawson and Locher (Dawson R J P, Locher K P. FEBS Ltrs 2007; 581: 935-8. Protein Data Bank, Accession Code 2ONJ).
Figure 16:
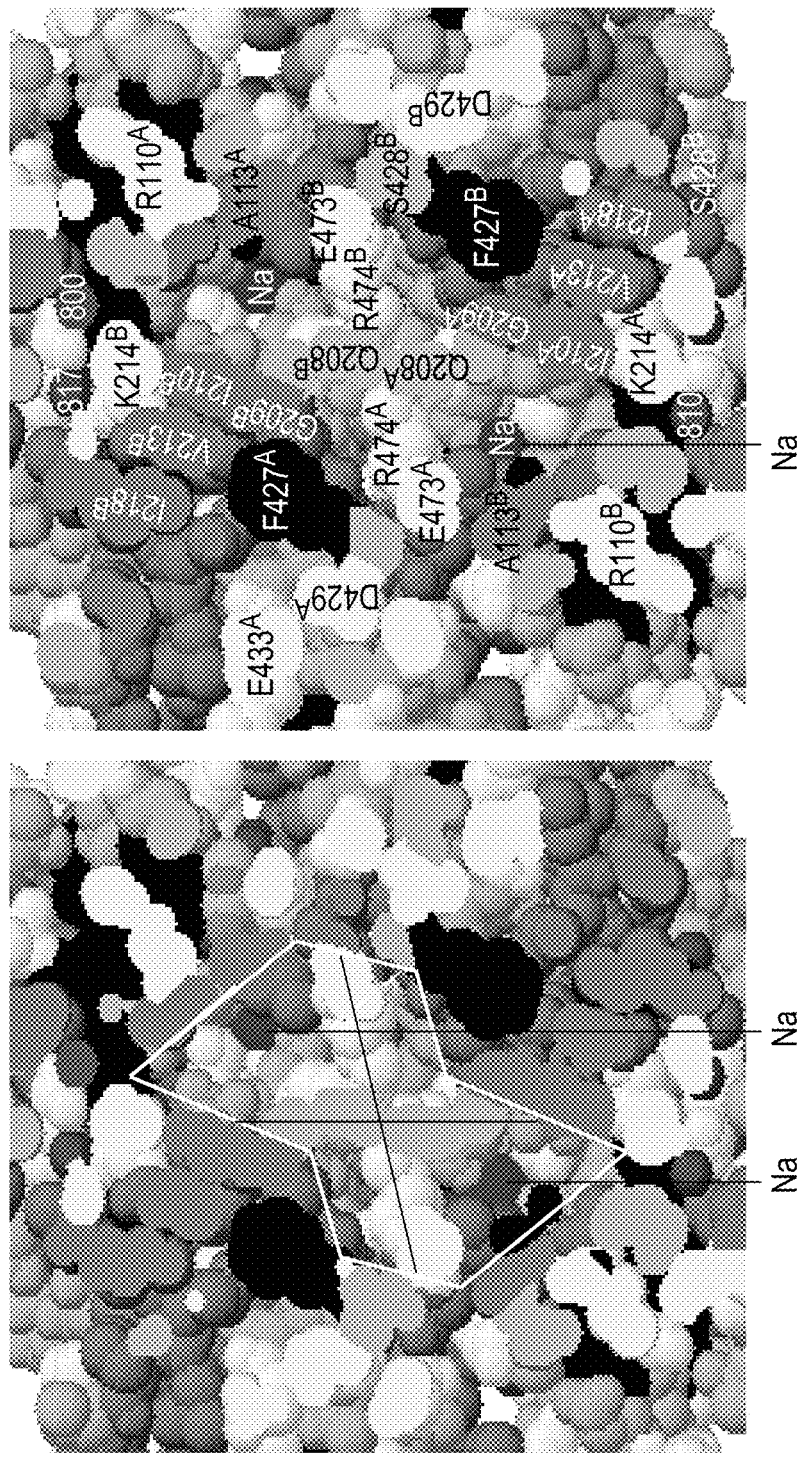
FIG. 16 is a horizontal cross-section of ABC exporter (Sav1866) at level 3 in FIG. 13 of cross-eye stereo view looking to top of internal aqueous chamber from base of nucleotide. Space filling representation as in FIG. 15. On left outline of aqueous chamber at level 3 and noting the X that subdivides the chamber and limits direction of ΔGap from ADP+Pi that opens the hydrophobic closure. Note the locations of the still visible blue Na ions. Protein Data Bank accession code 2ONJ due to Dawson and Locher (Dawson R J P, Locher K P. FEBS Ltrs 2007; 581: 935-8. Protein Data Bank, Accession Code 2ONJ).
Figure 17:
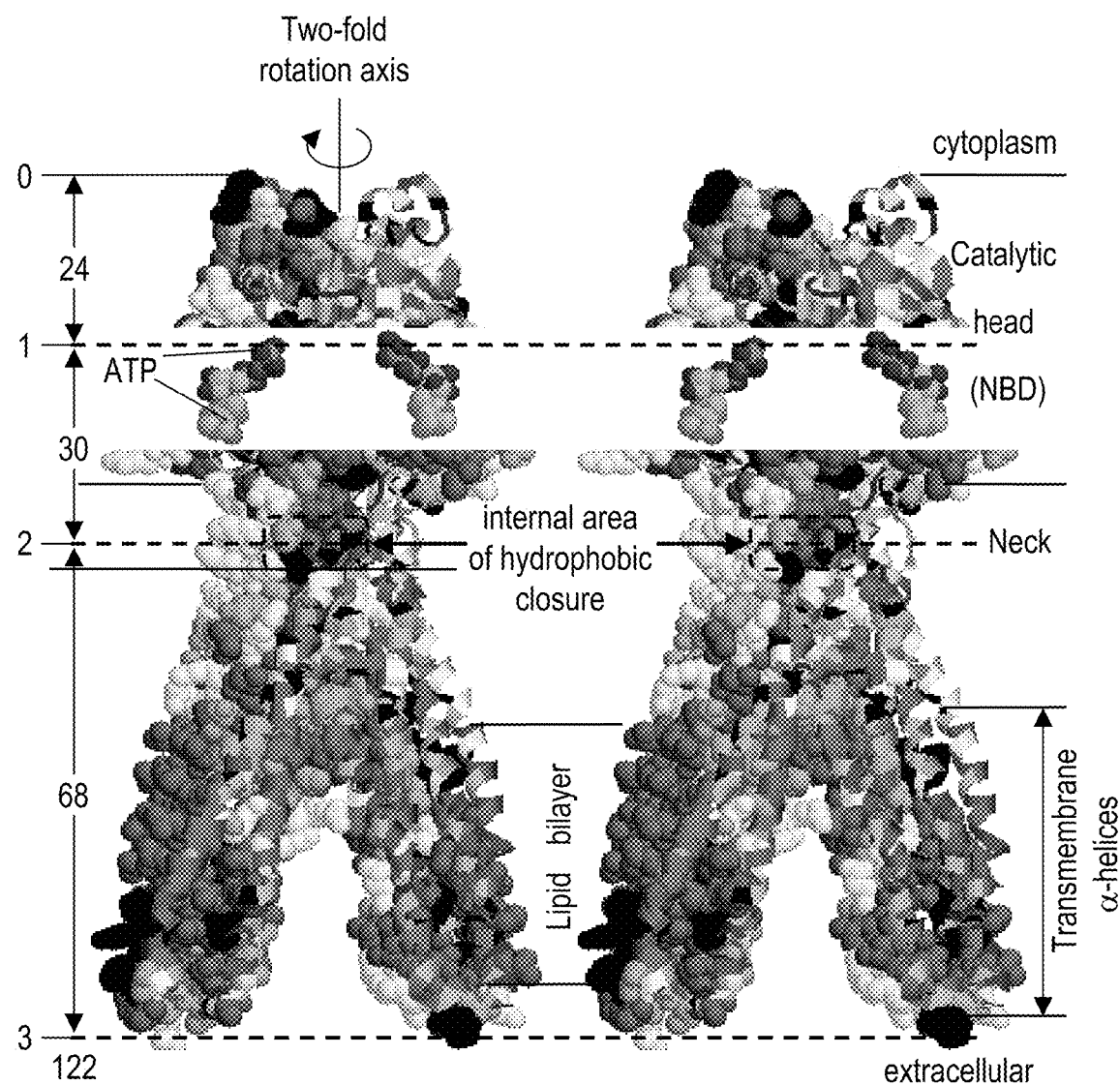
FIG. 17 is a cross-eye stereo view of MsbA (*Salmonella typhimurium* ABC exporter protein) in full frontal exposure with back chain, A, in space filling representation and front chain, B, in ribbon representation, and with a semi-transparent overlay of ligands to locate the ATP molecules within the structure. The length of the structure is 122 Å; the distance from the top to the γ-phosphate of ATP, $P^\gamma$, is 24 Å; the vertical distance from $P^\gamma$ to L125 of the hydrophobic gate is 30 Å (the vertical distance looking down into the polar chamber in FIG. 23A), and the distance looking from the extra-membranous side into the polar residue-lined aqueous channel to the hydrophobic gate is 68 Å (see FIG. 23B). From the crystal structure of Ward et al (Proc. Natl. Acad. Sci. USA vol. 104:19005-19010, 2007), Protein Data Bank accession code 3B60.
Figure 18A:
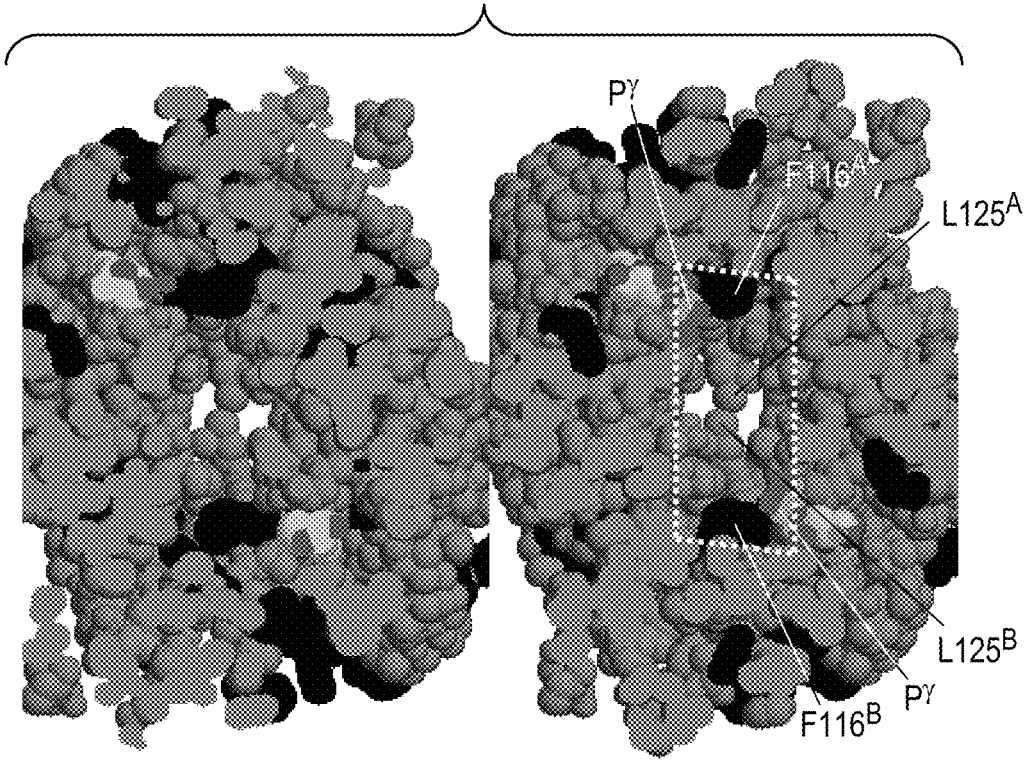
FIG. 18 is a cross-eye stereo view into polar chamber (A) and aqueous channel (B) of the dimeric ABC exporter protein, MsbA (*Salmonella typhimurium*), due to the crystal structure of Ward et al (Proc. Natl. Acad. Sci. USA vol. 104:19005-19010, 2007), Protein Data Bank accession code 3B60. A. Looking into the aqueous-polar chamber showing gray aliphatic and black aromatic residues and with polar residues absent, as in FIG. 21 for Sav1866. This is shown in cross-section looking down from level 2 of FIG. 22, the level of the ATP phosphates, a distance of 30 Å to the hydrophobic gate, residues $L125^{A\&B}$, $L128^{A\&B}$, $T204^{A\&B}$, and $A207^{A\&B}$, that is, at the level of the hydrophobic closure of the channel that we propose opens by apolar-polar repulsion on hydrolysis of 2ATP to 2ADP plus $2P_i$. The labeled $L125^{A\&B}$ δ-carbons form the singular closure for access into the aqueous channel that exits to the extracellular space. Also labeled are the $Y116^{A\&B}$ residues, which are separated by 22 Å and reside 23 Å below their respective γ-phosphates. The diagonal of the chamber measures about 30 Å with the $G381^{A\&B}$ inter-distance being 33 Å. B. Looking into the polar exit channel from level 3 to level 2, the closure is again seen to be achieved by the same $L125^{A\&B}$ δ-carbons as was seen on looking in from the level of the γ-phosphates to the base of the aqueous chamber. The hydrophobic $L125^{A\&B}$-gate is the singular blockage to the formation of a complete polar channel from γ-phosphates to the exit to the extra-cellular space.
Figure 18B:
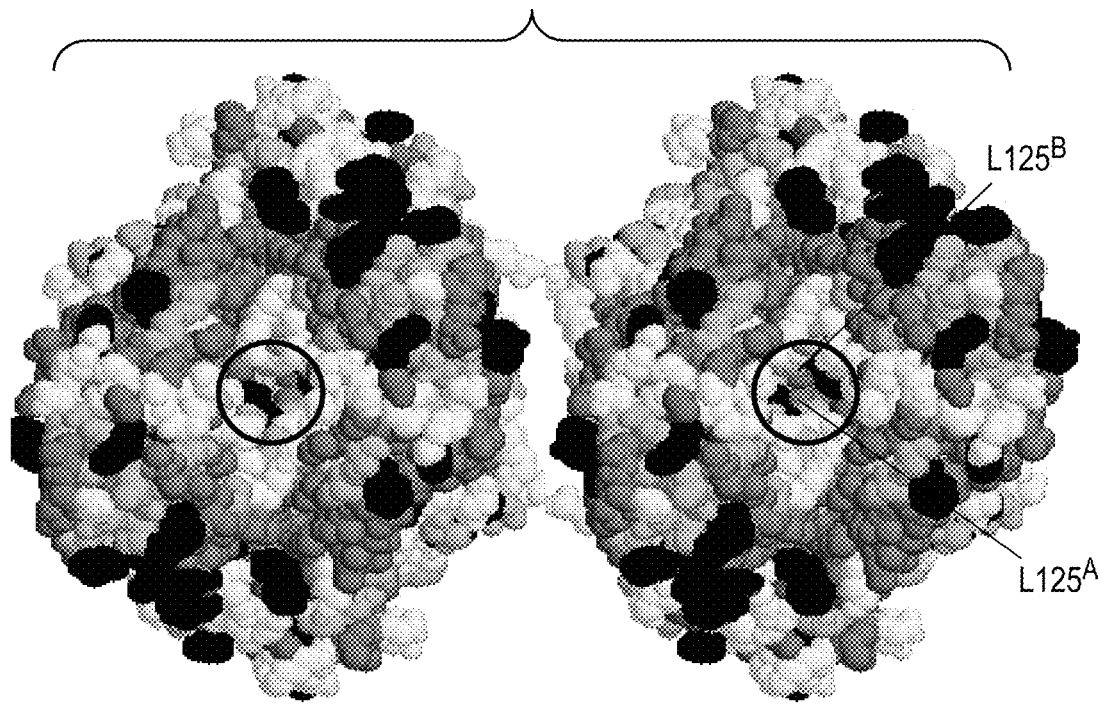
Figure 19:
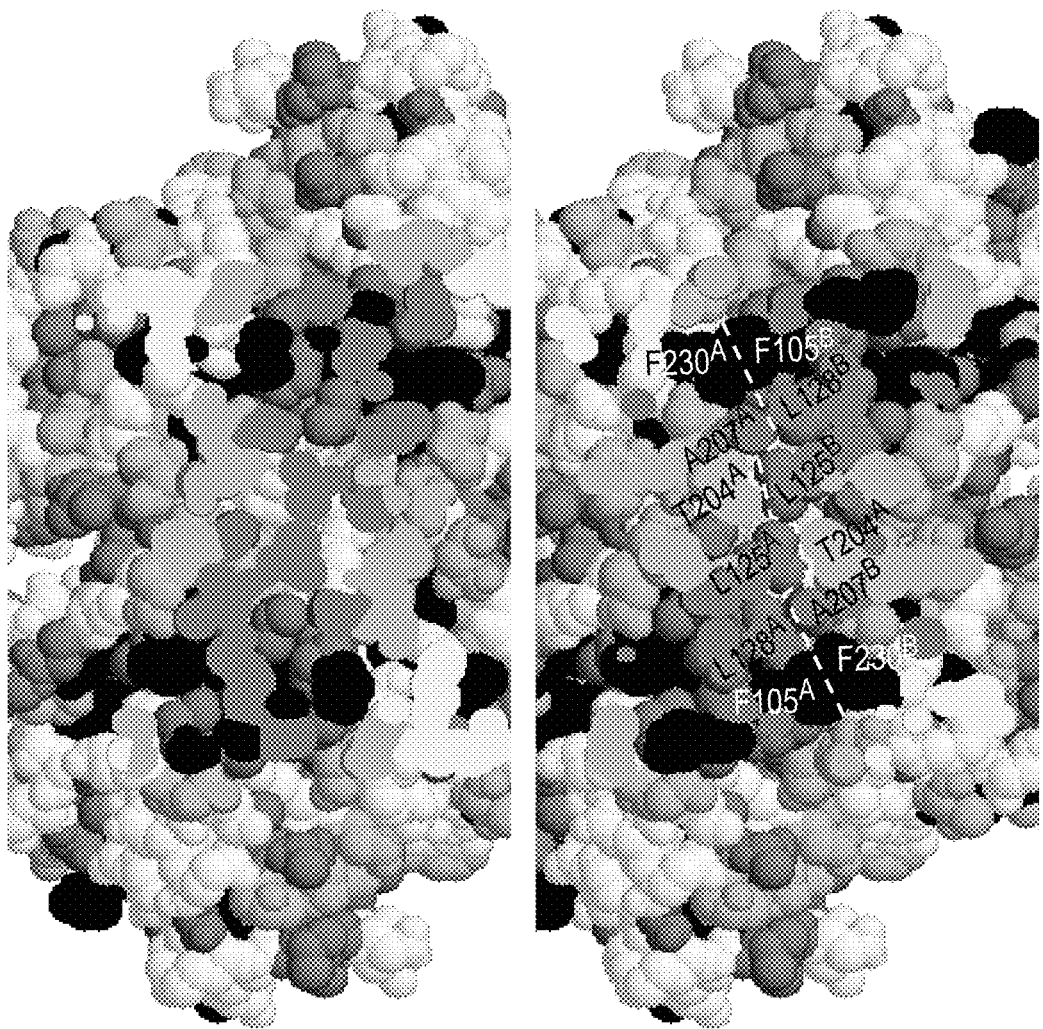
FIG. 19 is a cross-eye stereo view taken in cross-section at line 2 of FIG. 22 of the $L125^{A\&B}$-gate of MsbA (*Salmonella typhimurium* ABCB1 exporter protein). The $L125^{A\&B}$-gate shows a similar hydrophobicity in comparison with the $H204^{A\&B}$-gate of Sav1866 (See FIG. 21). The first tier of dissociable residues of the $L125^{A\&B}$-gate are seen as $L125^{A\&B}$, $L128^{A\&B}$, $T204^{A\&B}$, and $A207^{A\&B}$. It should be noted that the separation of the dimer into two monomers involves a second tier of residues. From the crystal structure of Ward et al (Proc. Natl. Acad. Sci. USA vol. 104:19005-19010, 2007), Protein Data Bank accession code 3B60.
Figure 20A:
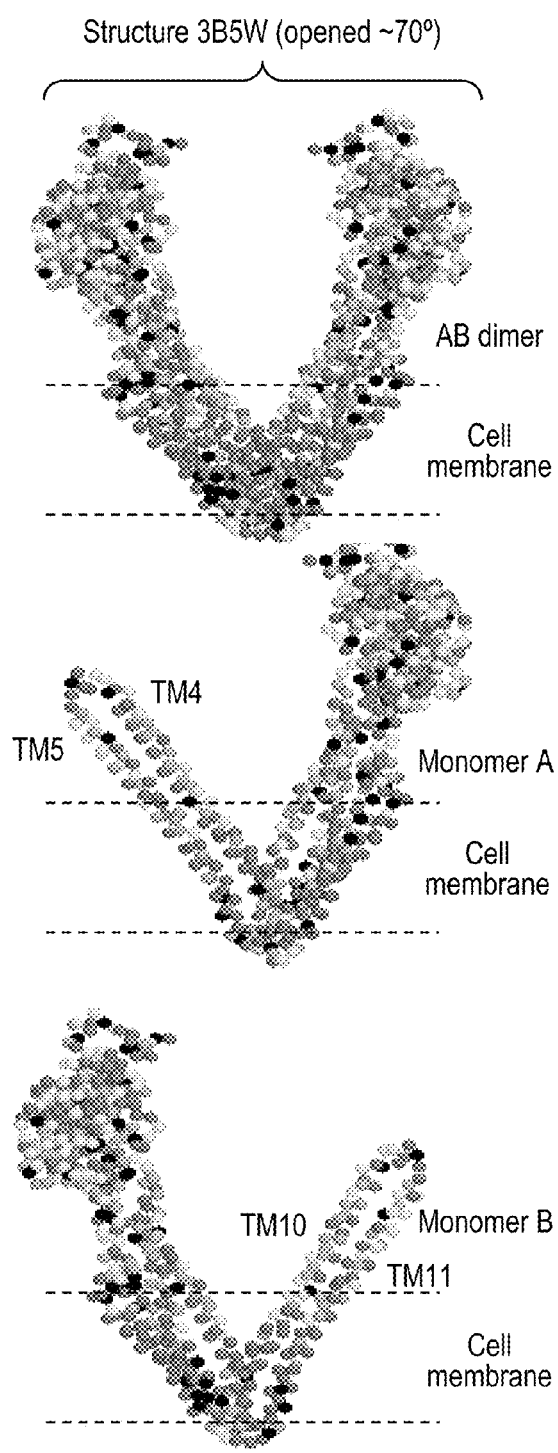
FIG. 20 is a series of inward facing conformations of MsbA structures, due to Ward et al. (Proc. Natl. Acad. Sci. USA vol. 104:19005-19010, 2007) with Protein Data Bank accession codes A. 3B5W from *Eschericia coli* (opened to ~70° and B. 3B5X from *Vibrio cholerae* (opened to ~30°). These inward facing conformations are thought to allow substrate loading from inside the cell or from the inner leaflet of the lipid bilayer of the cell membrane. Each structure is comprised of two chains, A and B and they are displayed in sequence from top to bottom as the AB dimer, monomer A and monomer B.
Figure 20B:
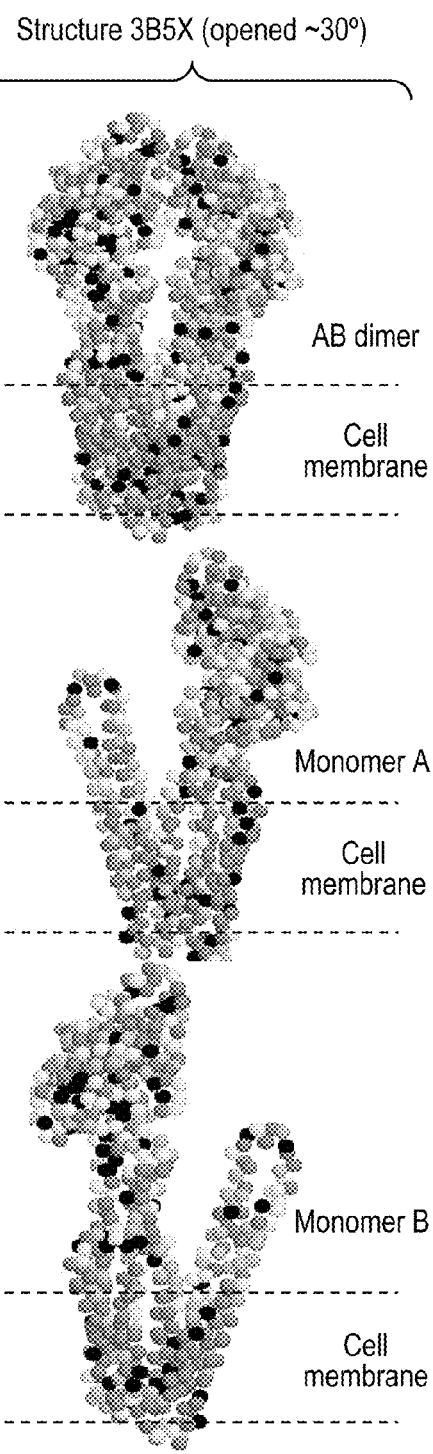
Figure 21A:
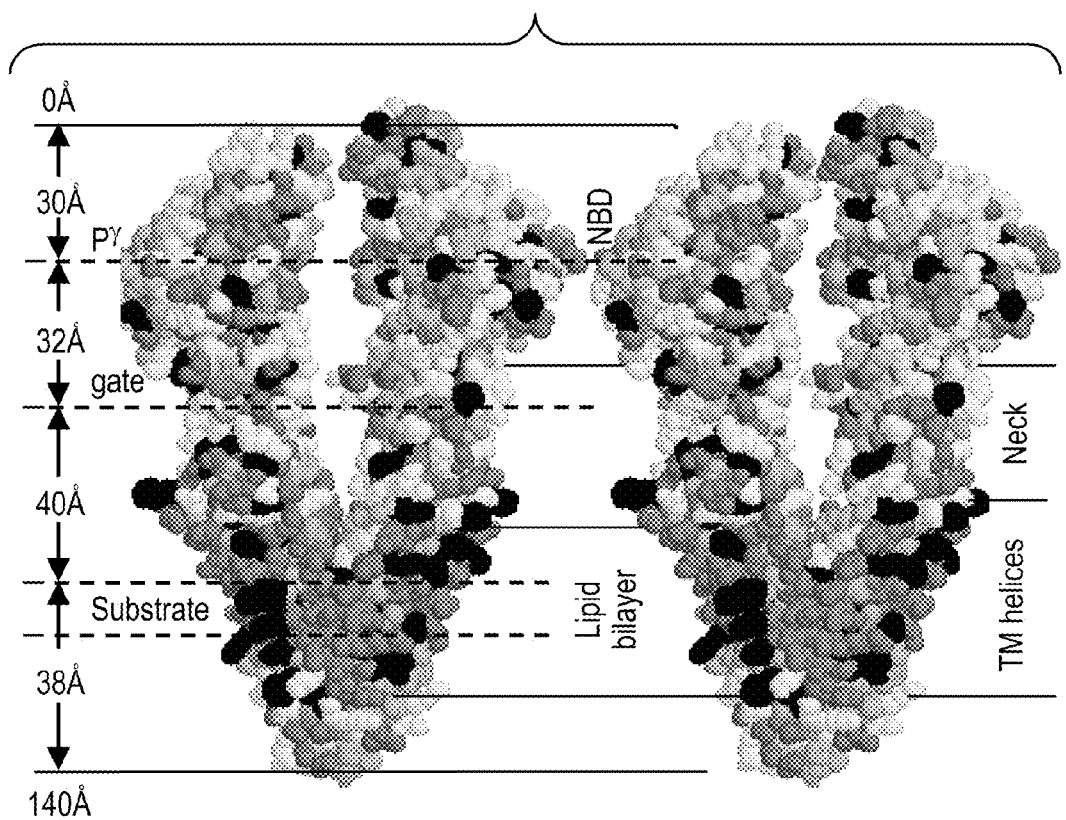
FIG. 21 is a series of crystal structures showing P-glycoprotein of mouse ABCB1 exporter protein full view of A'A" in the inward facing conformation. A. Stereo view in space filling representation with white charged residues, light gray neutral residues, gray hydrophobic (aliphatic) residues, and black aromatic residues, showing dark transmembrane portion and extra-membranous neck and globular nucleotide binding domains. See discussions of the significance of the distances in the text. B. Identical view as in A but in ribbon representation showing the helical transmembrane portion. From Aller et al (Science vol. 323: 1718-1722, 2009) obtained from the Protein Data Bank as accession code 3G5U.
Figure 21B:
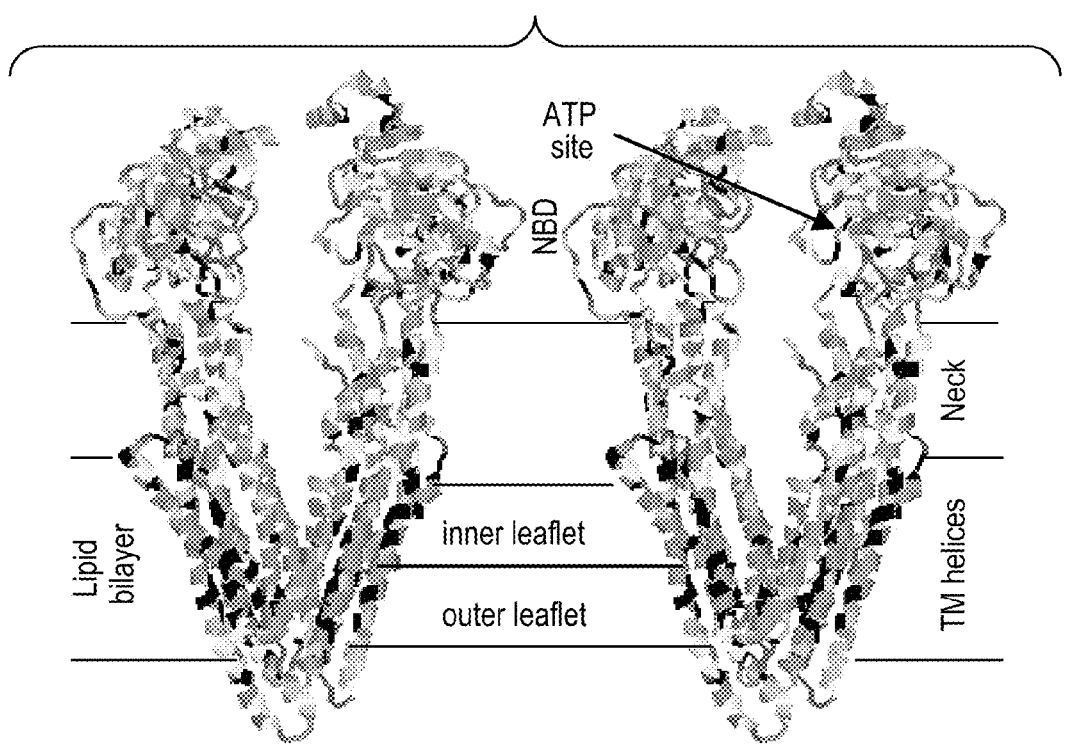
Figure 22A:
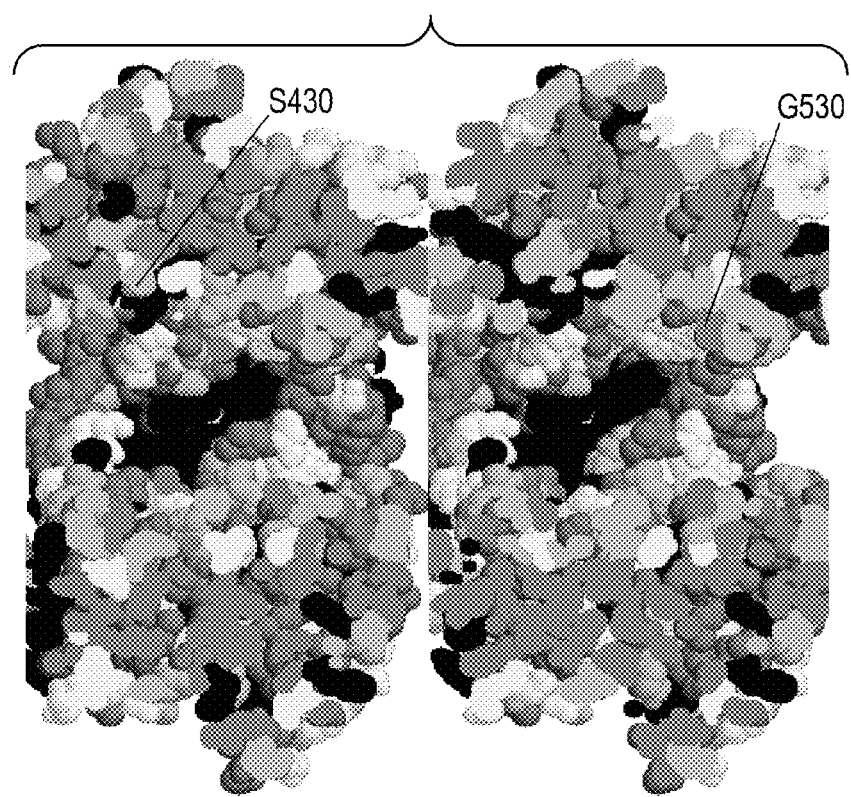
FIG. 22 are cross-eye stereo views of the ABC exporter protein, P-glycoprotein from mouse, taken in cross-section near the level of the putative $P^\gamma$ of ATP as estimated from the location of residue S430 of the primary ATP binding site and G530 of the signature sequence, QLSGG, of the secondary binding site. Structures due to From Aller et al (Science vol. 323: 1718-1722, 2009) obtained from the Protein Data Bank. A. Uses structure 3G5U with neither nucleotide nor substrate binding sites occupied. B. Uses structure 3B60 with inhibitor present to identify the substrate binding site.
Figure 22B:
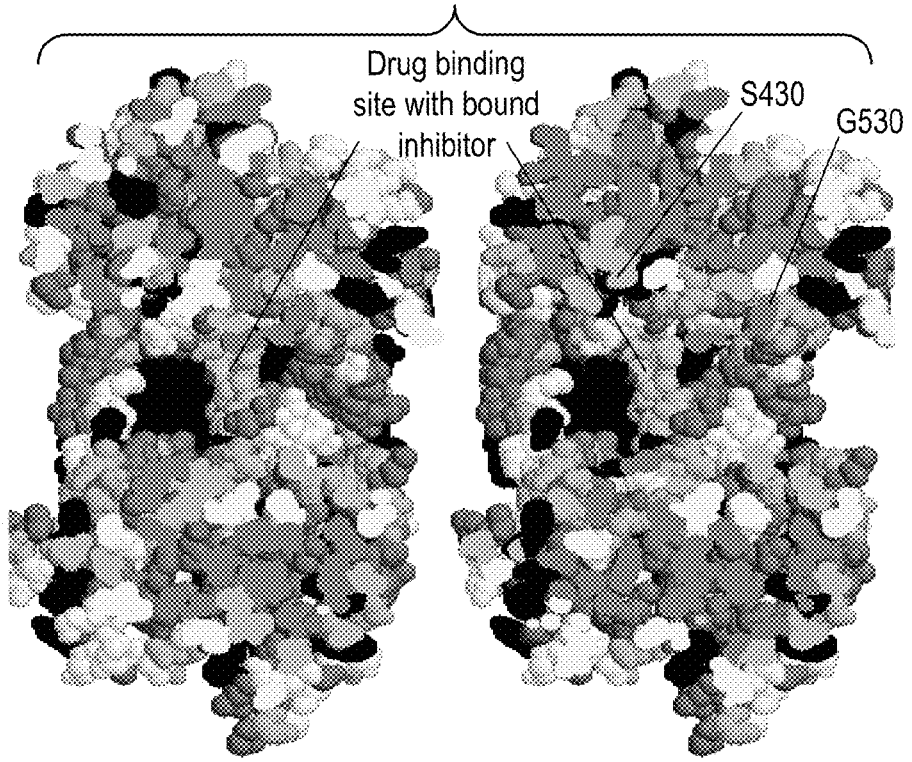
Figure 23A:
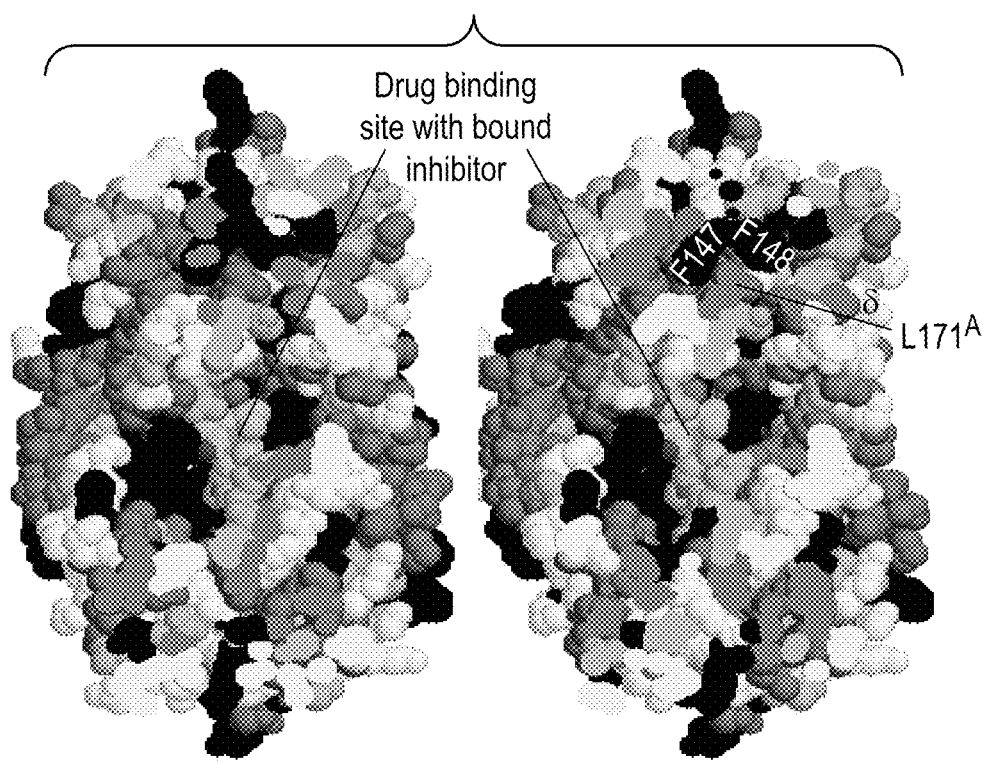
FIG. 23 is a series of cross-eye stereo views of the ABC exporter protein, P-glycoprotein from mouse, a cross-section taken near the level of the putative hydrophobic gate for structure 3G60 with inhibitor present. Structures of Aller et al (Science vol. 323: 1718-1722, 2009) obtained from the Protein Data Bank. A. Structure 3G5U contains neither nucleotide nor substrate binding sites occupied. B Structure 3B60 with hydrophobic inhibitor present.
Figure 23B:
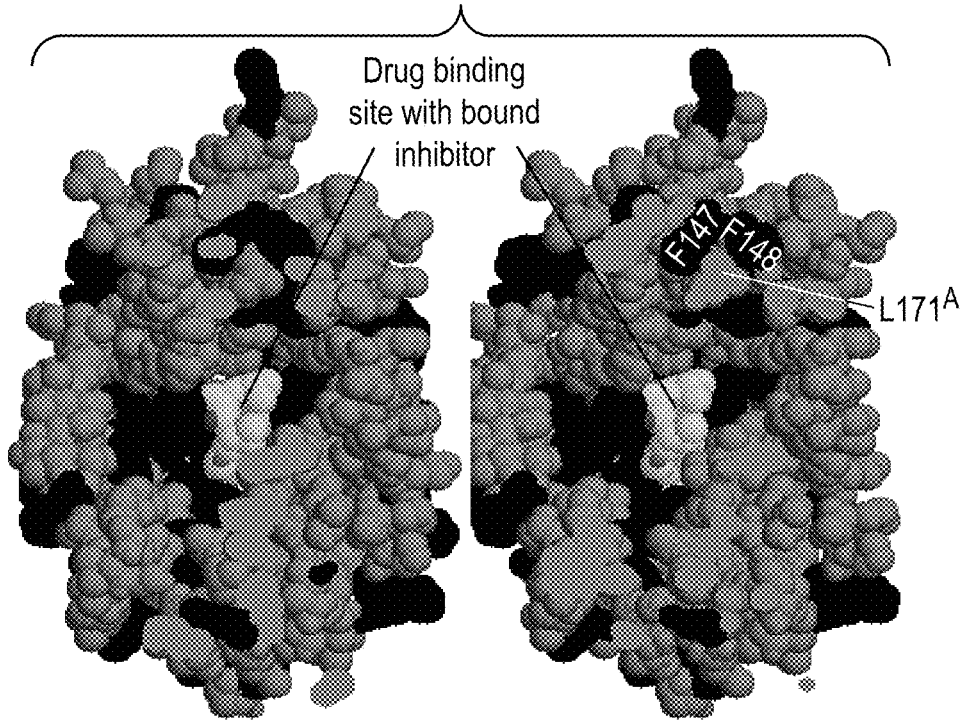
Figure 24:
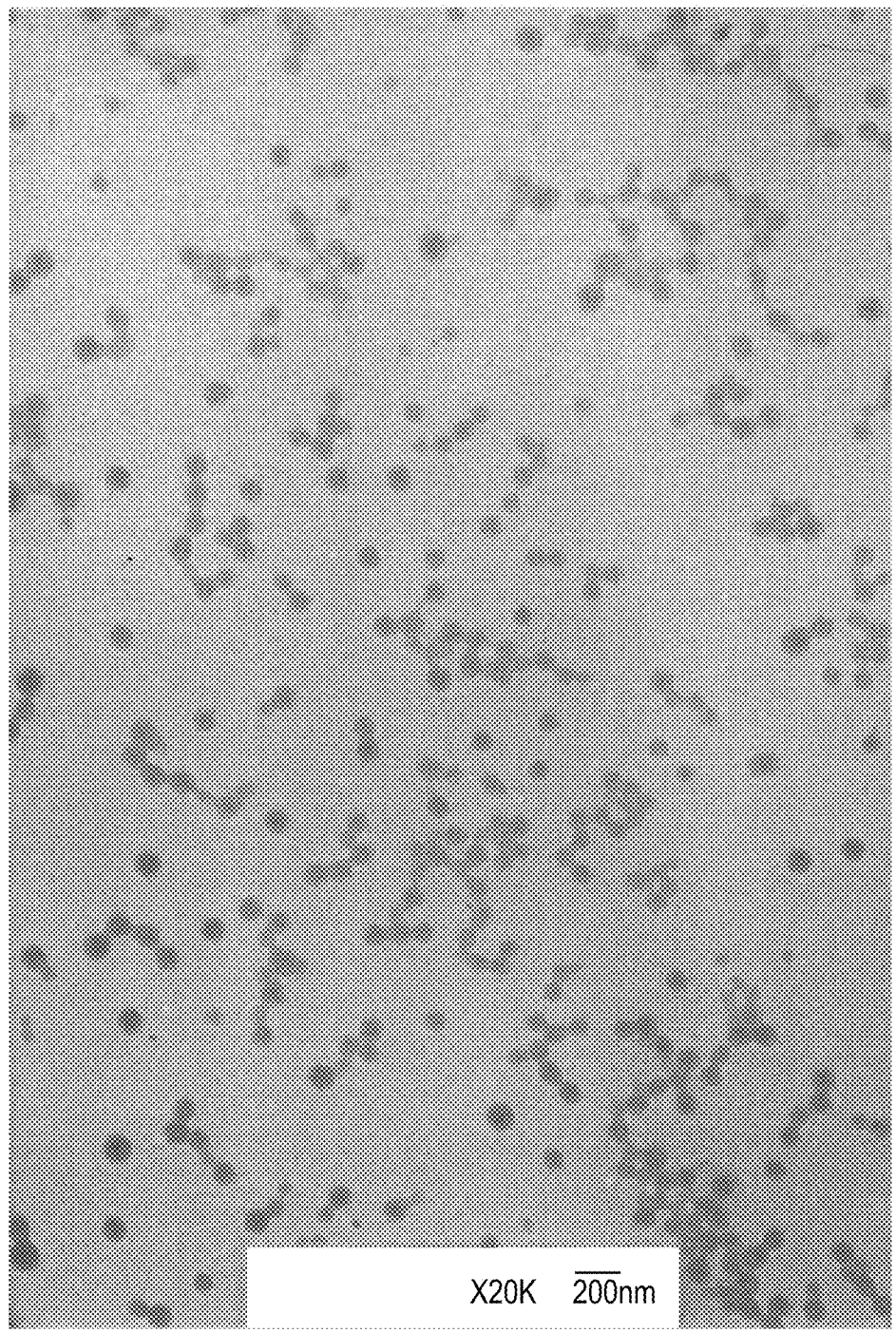
FIG. 24 Electron micrograph of negatively stained nanoparticles comprised of (GVGVP GVGFP GEGFP GVGVP GVGFP GFGFP)$_{42}$ (GVGVP). (SEQ ID NO:7). The ECMP is a polymer of 253 pentamers showing fairly uniform particles with a nominal size of 50 nm. Dan W. Urry, T. Cooper Woods, Larry C. Hayes, Jie Xu, Masamichi Iwama, Masakazu Furuta, Toshio Hayashi, Mitsuhiro Murata, Timothy M. Parker, "Elastic Protein-Based Biomaterials: Elements of Basic Science, Controlled Release and Biocompatibility," In: BIOMATERIALS HANDBOOK—Advanced Applications of Basic Sciences and Bioengineering. D L. Wise Coord. Ed, Marcel Dekker, Inc., New York, pp. 31-54, 2004.
Figure 25A:
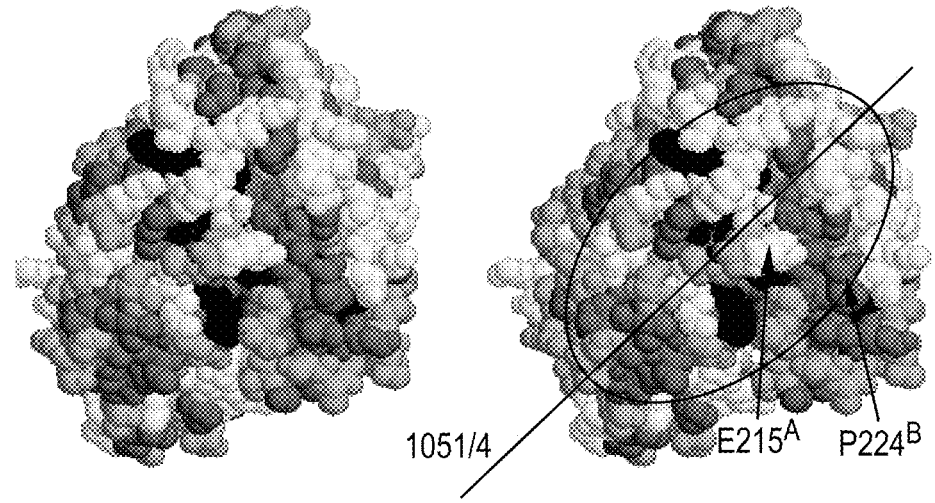
FIG. 25 is Fab1(chainA) and Fab2(chainB) stereo end views in space-filling representation. A. Proximal end attached at nanoparticle surface by means of $E215^A$ and $P224^B$ contiguous with residue 1 of ECMP1. directed out of distal end for binding at antigen-binding site. Developed from the crystal structure of S. Uysal, V. Vásquez, V. Tereshko, K. Esaki, F. A. Fellouse, S. S. Sidhu, S. Koide, E. Peroz and A. Kossiakoff *Proc. Natl. Acad. Sci. USA*, 2009, 106, 6644-6649, obtained from the Protein Data Bank accession code 3EFF.Accession code Protein Data Bank 3EFF due to S. Uysal et al. (*Proc. Natl. Acad. Sci. USA*, 2009, 106, 6644-6649. Protein Data Bank accession code 3EFF). A. Proximal end at nanoparticle surface
Figure 25B:
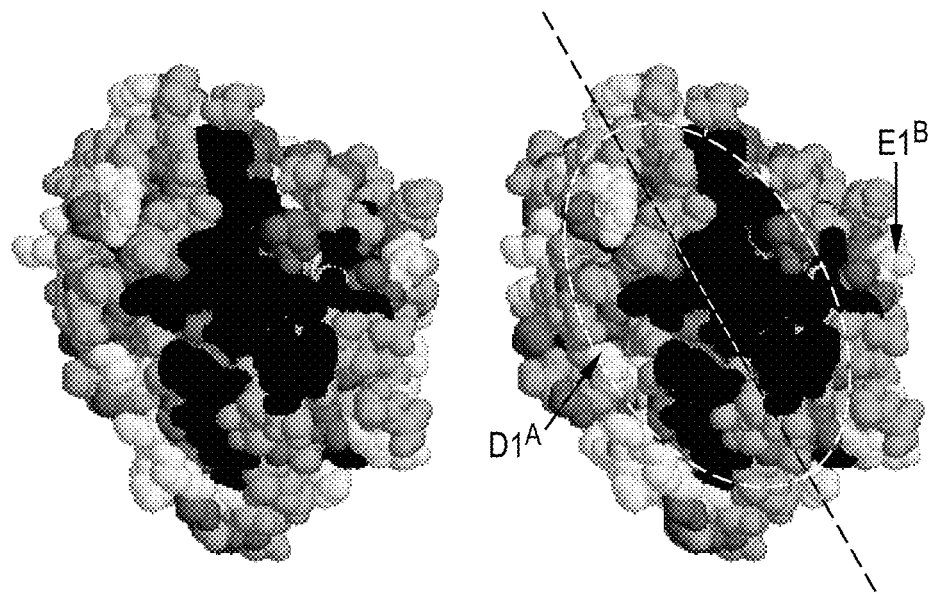
Figure 26A:
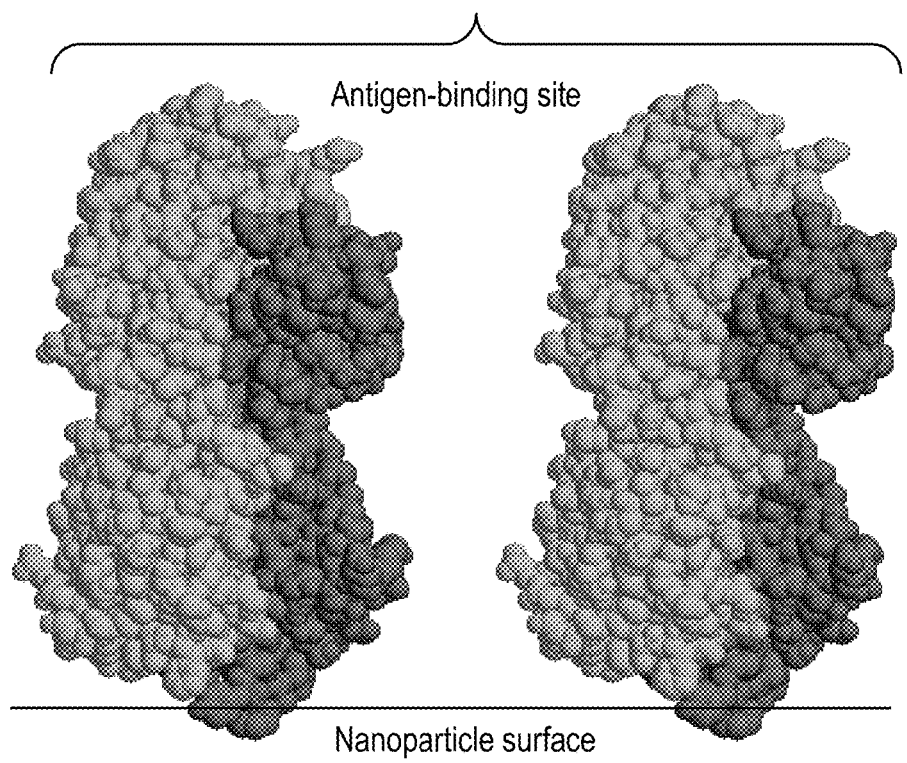
FIG. 26 is Fab1(chainA) and Fab2(chainB)-stereo side-views with proximal end at bottom and distal end at top. Accession code Protein Data Bank 3EFF. A.
Figure 26B:
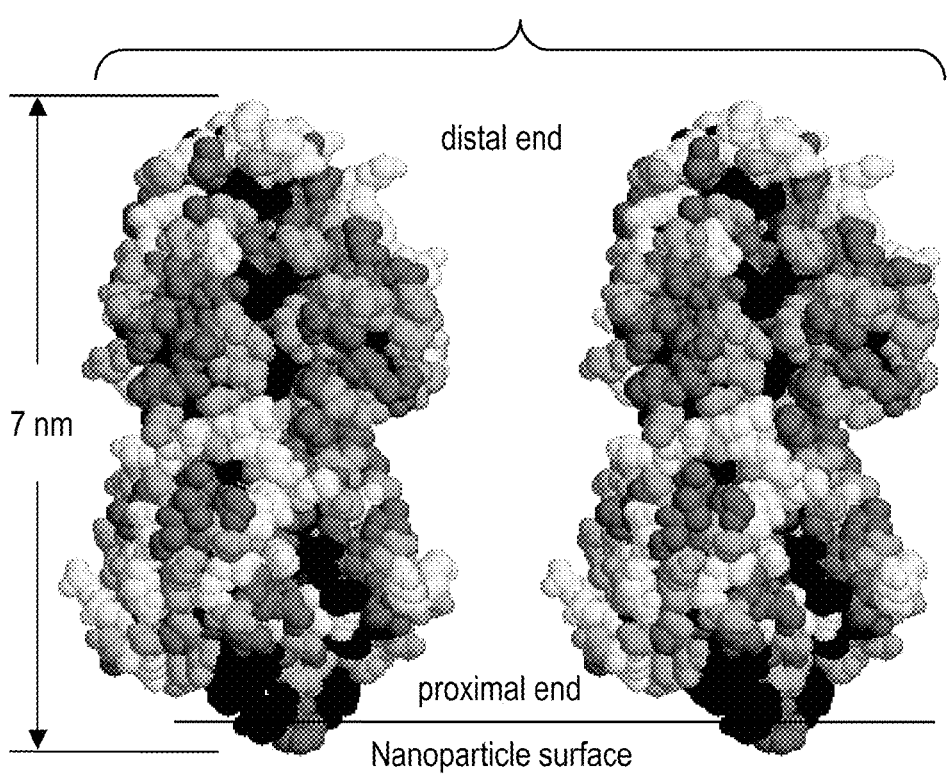

Once the values are determined by difference with $\Delta H_t$ (GVGVP) (SEQ ID NO:4) as represented in FIG. 1E, they are translated so the reference polymer is taken as (GGGVP (SEQ ID NO:11), as this residue is considered to be close to neutral, being neither polar nor apolar. For use of (GGGVP) (SEQ ID NO:11) as the reference, i.e., $\Delta H_t$(GGGVP) (SEQ ID NO:11)=$\Delta H_t$(ref), in Table 3 and FIG. 13, the change in Gibbs free energy for hydrophobic association is indicated as $\Delta G°_{HA}$, i.e., (9)   $\Delta G°_{HA} \equiv \Delta H_t$(ref) - $H_t$(GχGVP)   (SEQ ID NO: 2)

Figure 2:
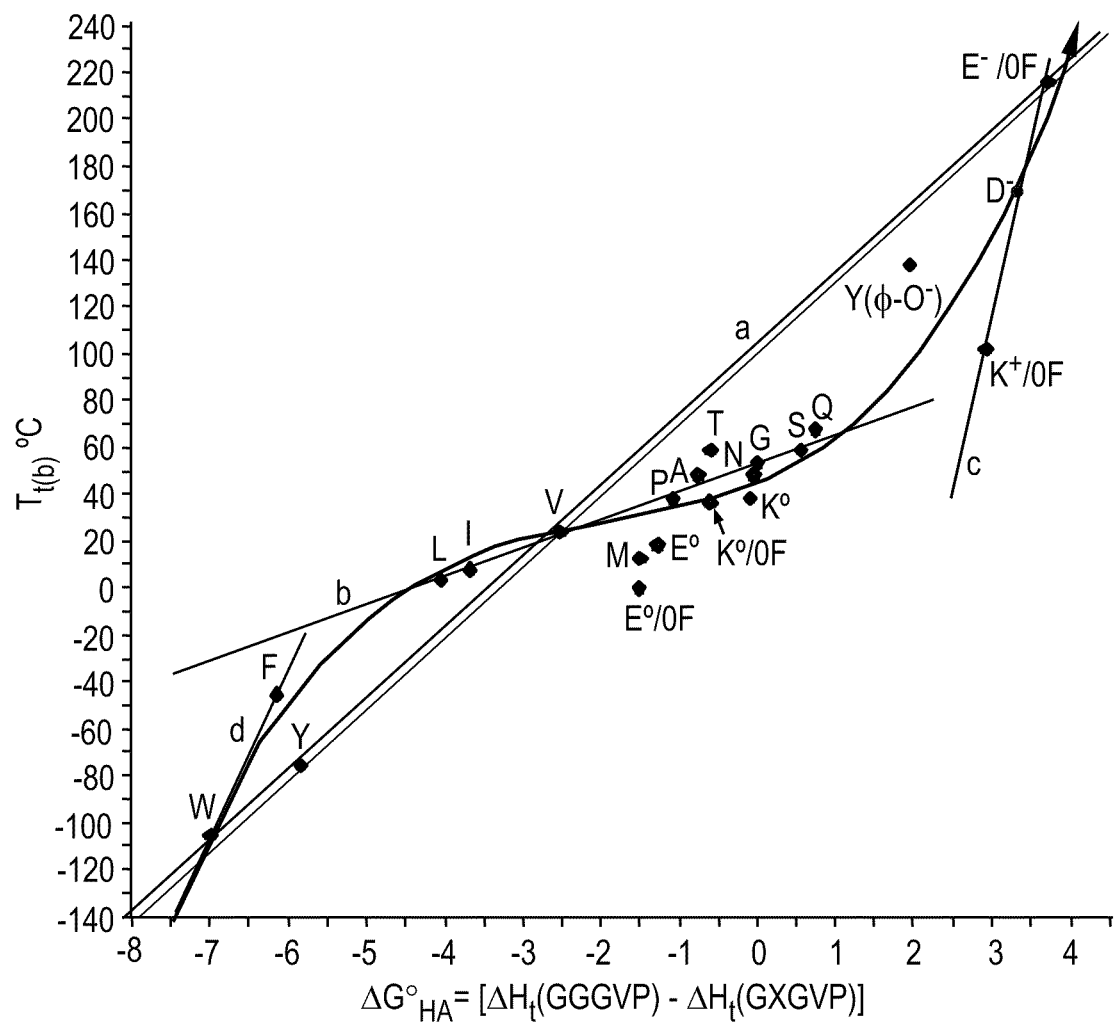
FIG. 2 is a plot of the change in Gibbs free energy of hydrophobic association, $\Delta G_{HA}$, as a function of $T_{b(t)}$, the temperature of the inverse temperature transition whether determined from differential scanning calorimetry (DSC) data, $T_b$, or by the onset temperature for aggregation, $T_t$, as determined by the temperature dependence of turbidity formation for naturally-occurring amino acid residues. $T_t$ and $T_b$ are defined in FIG. 1. The amino acid sequences in FIG. 2 are SEQ ID NO:11 and SEQ ID NO:2 (from left to right).
Figure 4A:
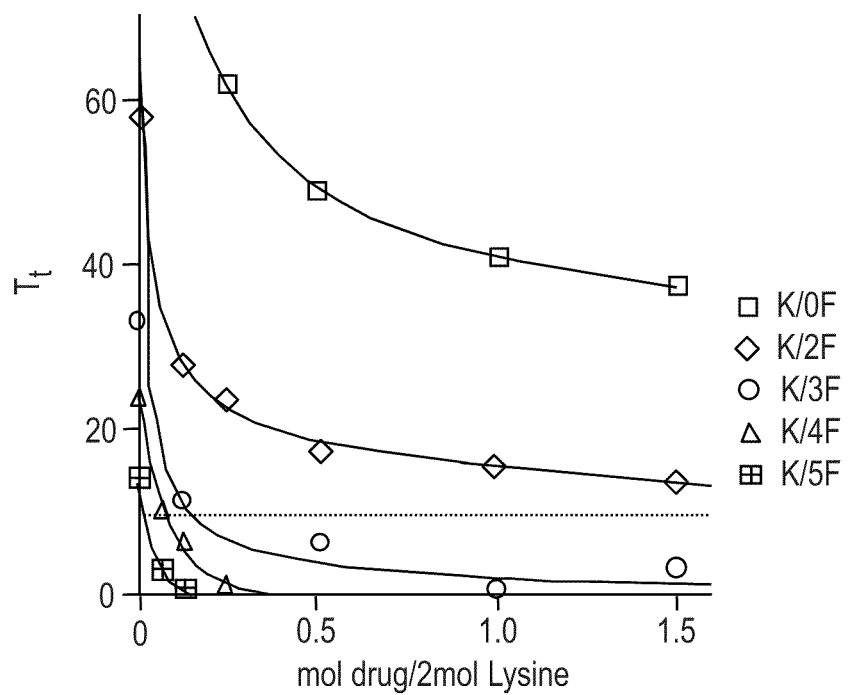
FIG. 4 is a pair of graphs of loading profiles showing increased affinity of model protein for drug as hydrophobicity is increased by n of nF increasing, that is, as increasing numbers of Val (V) residues are replaced by Phe (F) residues using the series of Lys (K)/Phe (F)-containing model proteins of Table 3 with Φ=K. Dashed line locates 37° C. line where it is seen that K/0F is not useful for delivery of either Dexamethasone-phosphate or Betamethasone-phosphate because it does not form a drug laden phase separated state until the ratio of drug/2[K$^+$] is greater than 1.5. A. Dexamethasone-phosphate loading curves and B. Betamethasone-phosphate loading curves.
Figure 4B:
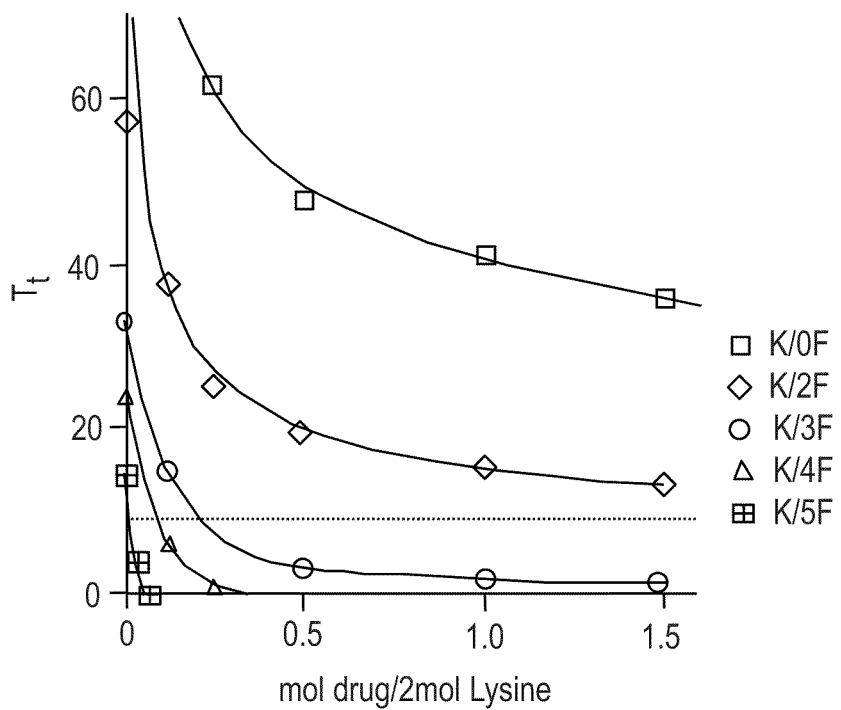
Figure 5A:
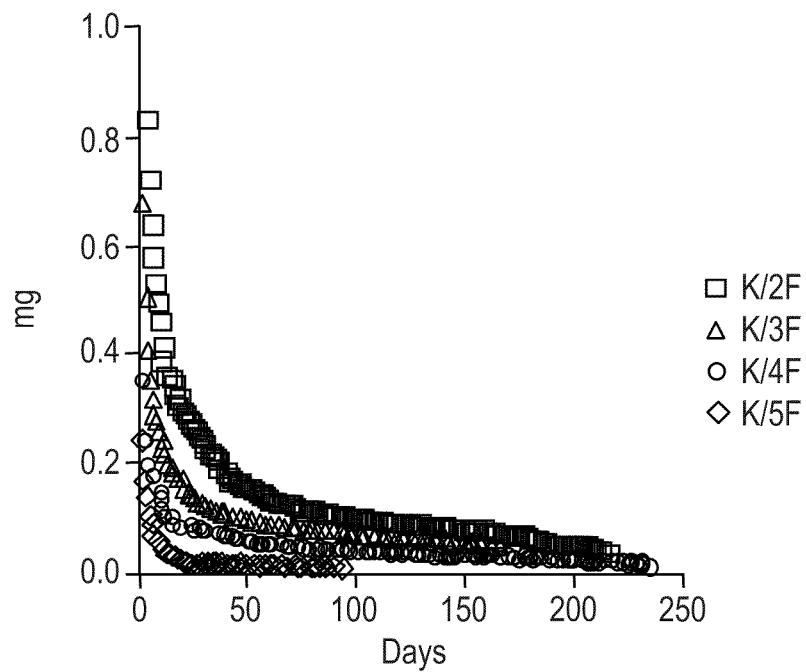
FIG. 5 is a pair of graphs of release profiles showing lower rates of drug release as n of nF increases, that is, as increasing numbers of Val (V) residues are replaced by Phe (F) residues using the series of Lys(K)/Phe(F)-containing model proteins of Table 3 with Φ=K. As the negatively-charged drug is added to the soluble positively-charged model protein phase separation occurs. Drug is added to a 50% excess, which is responsible for the burst release. A. Dexamethasone-phosphate release curves and B. Betamethasone-phosphate release curves.
Figure 5B:
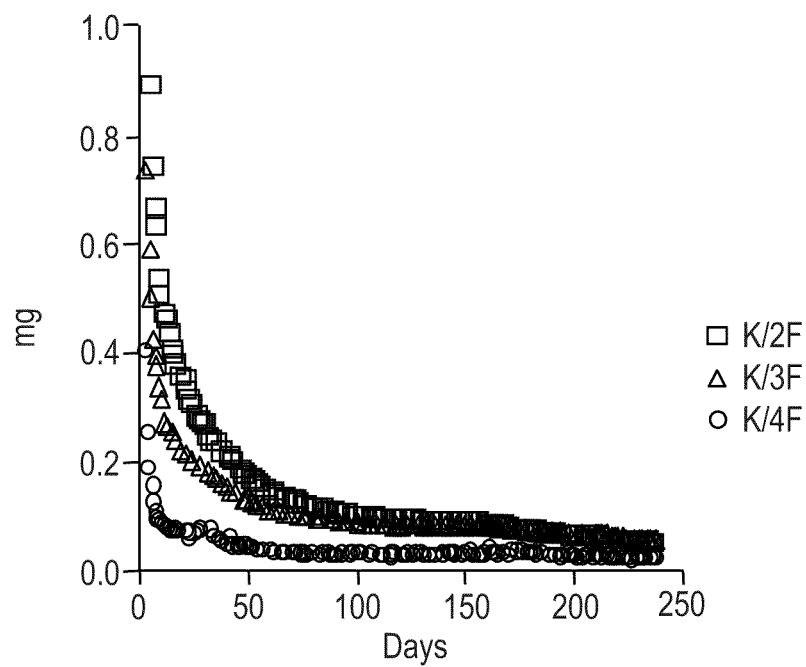
Figure 6A:
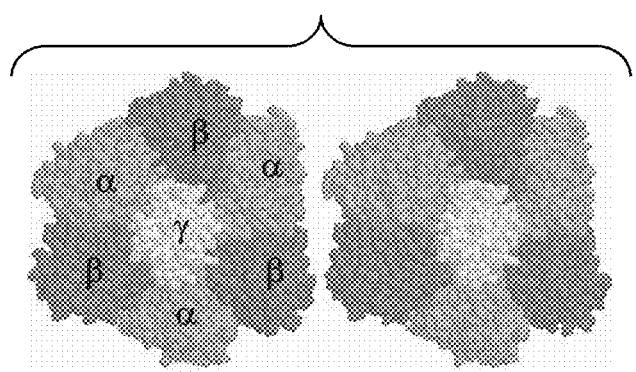
FIG. 6 is a series of cross-eye stereo views in space filling representation of F$_1$-ATPase, the F$_1$-motor of ATP synthase showing the γ-rotor in white, the non-catalytic α-subunit in light gray and the β-catalytic subunit in gray. A. Top view along three-fold symmetry axis showing the central γ-subunit surrounded by three fold symmetric (αβ) subunits. B. Side view showing top of the γ-rotor extending from the top of the (αβ)3 motor housing, and two β-subunits separated by an α-subunit. C. Vertical section showing the γ-rotor pressed against an empty β-catalytic subunit and showing the aqueous cleft at the base of which inorganic phosphate, Pi, is considered to occur and from which an apolar-polar repulsion is directed at the most hydrophobic face of the γ-rotor. Protein Data Bank accession code 1H8E.
Figure 6B:
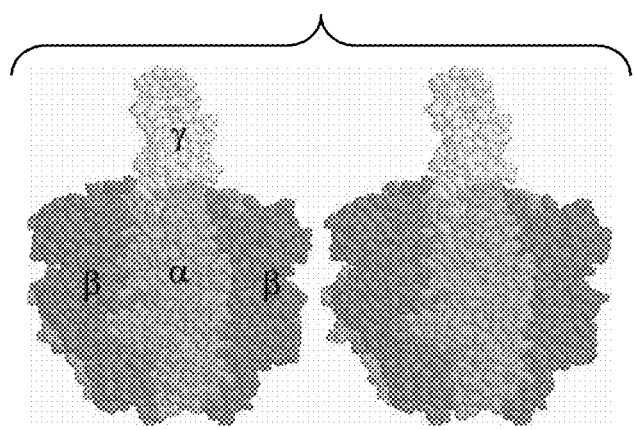
Figure 6C:
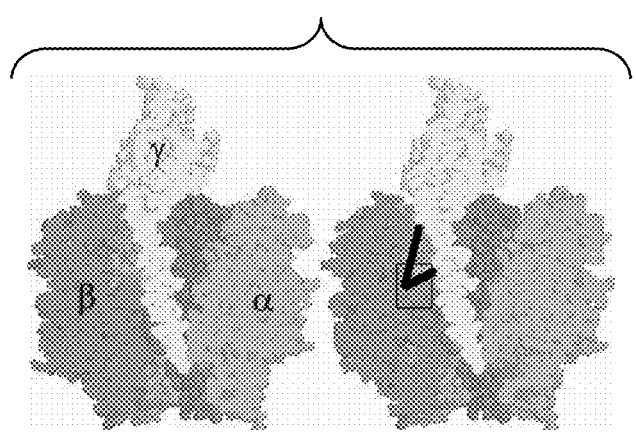
Figure 7:
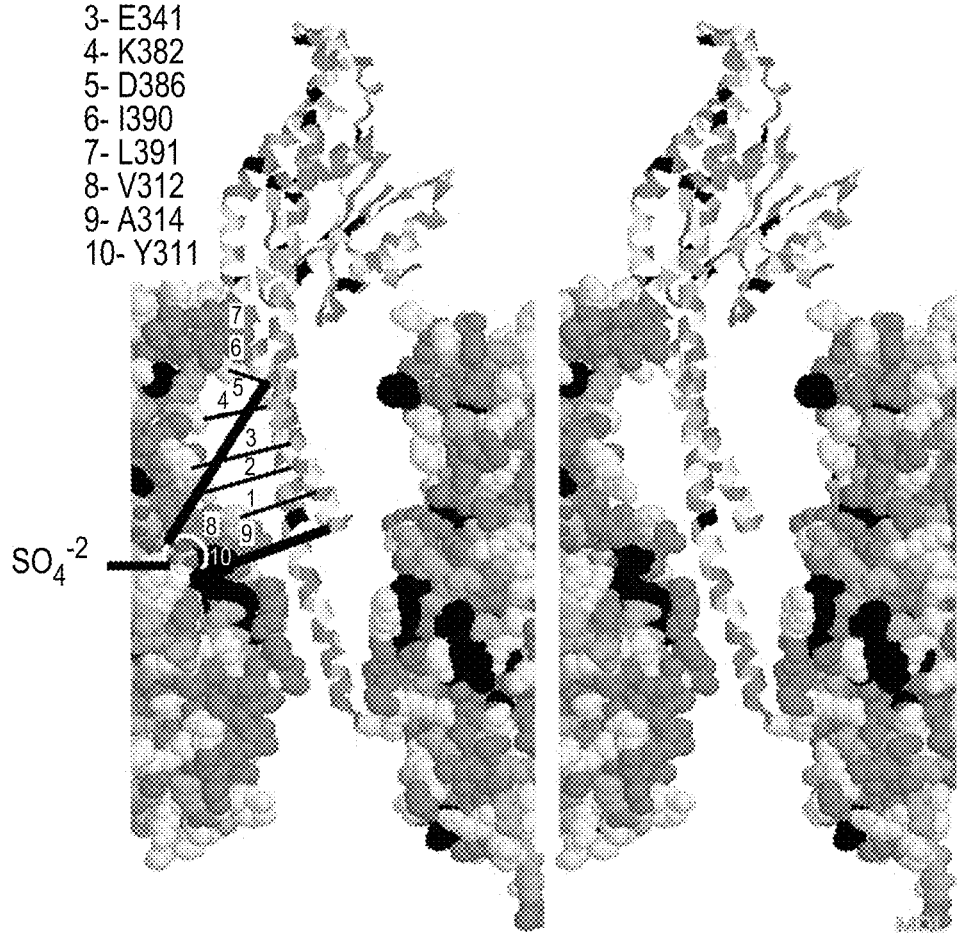
FIG. 7 is a cross-eye stereo view of the F$_1$-motor of ATP synthase with γ-rotor in ribbon and α- and β-subunits in space-filling representations with residues indicated as neutrals light gray, hydrophobics gray, aromatics black and charged white. Lines to indicate a repulsive interaction, ΔGap, between hydrophobic γ-rotor and SO$_4$, in place of hydrolyzed γ-phosphate, and augmented by newly emerged charged groups that occur in the β-subunit. The ΔGap due to SO$_4$ and emerged charged groups apply a torque to the double-stranded sequence of γ-rotor that would give a counter-clockwise rotation when functioning as an ATPase. Protein Data Bank accession code 1H8E. From Menz et al Menz R I, Walker J E, Leslie A G W. Structure of bovine mitochondrial $F_1$-ATPase with nucleotide bound to all three catalytic sites: Implications for mechanism of rotary catalysis. Cell 2001; 106: 331-41. Protein Data Bank, Accession Code 1H8E.
Figure 8:
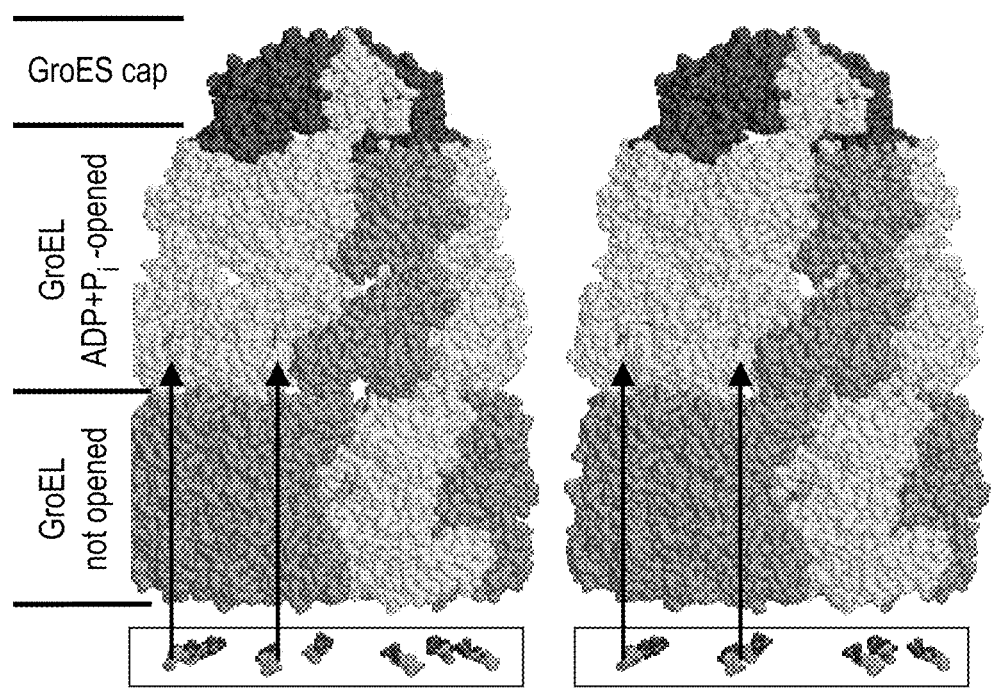
FIG. 8 is a pair of crystal structures of the seven-fold symmetric GroEL-GroES-(ADP)$_7$ chaperonin molecule having asymmetric Gro/EL rings, shown in cross-eye stereo view. The GroES cap is in dark gray with one subunit in white, the (ADP+Pi)-expanded Gro/EL in white with one subunit in light gay, and Gro/EL without nucleotide in light gray with one subunit in white. Below is the stereo view of nucleotides positioned exactly as in the vertically expanded Gro/EL with arrows to give relationship. Protein Data Bank accession code 1OAN (from Xu et al., Nature 1997; 388: 741-50. Protein Data Bank, Accession Code 1OAN).
Figure 9B:
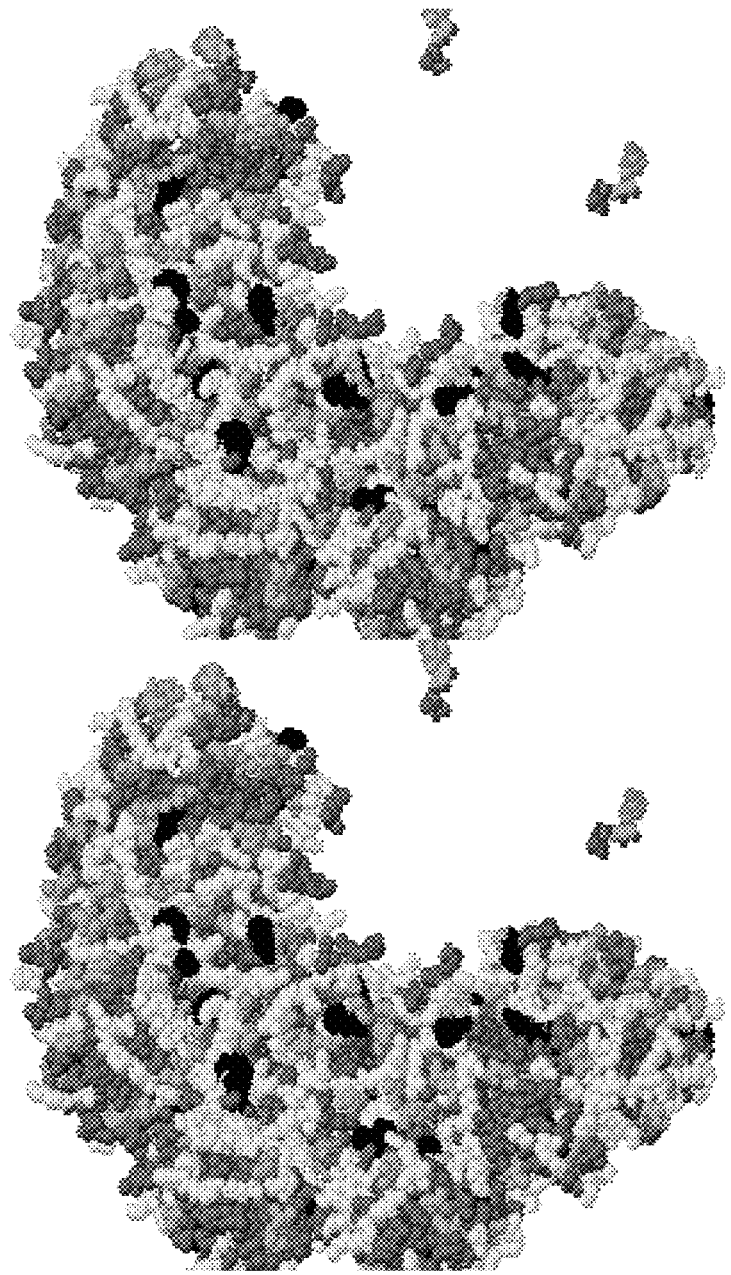
FIG. 9 A. is a slab cut of the crystal structure of the seven-fold symmetric molecular chaperonin, GroEL-GroES-(ADP)$_7$, shown in cross-eye stereo view to expose large internal aqueous chambers. Of the two GroEL rings, the upper ring has been expanded by ATP to form a large internal 175 nm$^3$ aqueous chamber with a semi-transparent overlay positioning seven ADP recessed in its base from which a phosphate can peek out of its peep hole a distance of 7 nm toward the upper part of the chamber that during function would contain a hydrophobically mis-folded protein, schematically represented here as a sphere. As represented by the double-headed arrows labeled, $\Delta G_{ap}$, there can exist an apolar-polar repulsive free energy of hydration between phosphate and hydrophobically-mis-folded protein at a 7 nm distance where it is to be unfolded by 7(ADP+PO$_4^{-3}$) and smoothly hydrophobically refolded as the seven PO$_4^{-3}$ diffuse out of the chamber one at a time. Protein Data Bank accession code 1OAN (from Xu et al Nature 1997; 388: 741-50. Protein Data Bank, Accession Code 1OAN). B. A view looking into the expanded GroEL from above with the GroES cap removed, with three of the seven GroEL protein subunits removed, and with all seven ADP molecules present. This demonstrates that the phosphate of ADP is recessed in a pit an that the sight from the pit is directed upward toward the upper part of the chamber. The crystal structure due to Zu et al. Xu Z. Horwich A L. Sigler P B. The crystal structure of asymmetric GroEL-GroEs-(ADP)$_7$ chaperonin complex. Nature 1997; 388: 741-50. Protein Data Bank, Accession Code 1OAN and the data obtained from the Protein Data Bank as accession code 1OAN.
Figure 10:
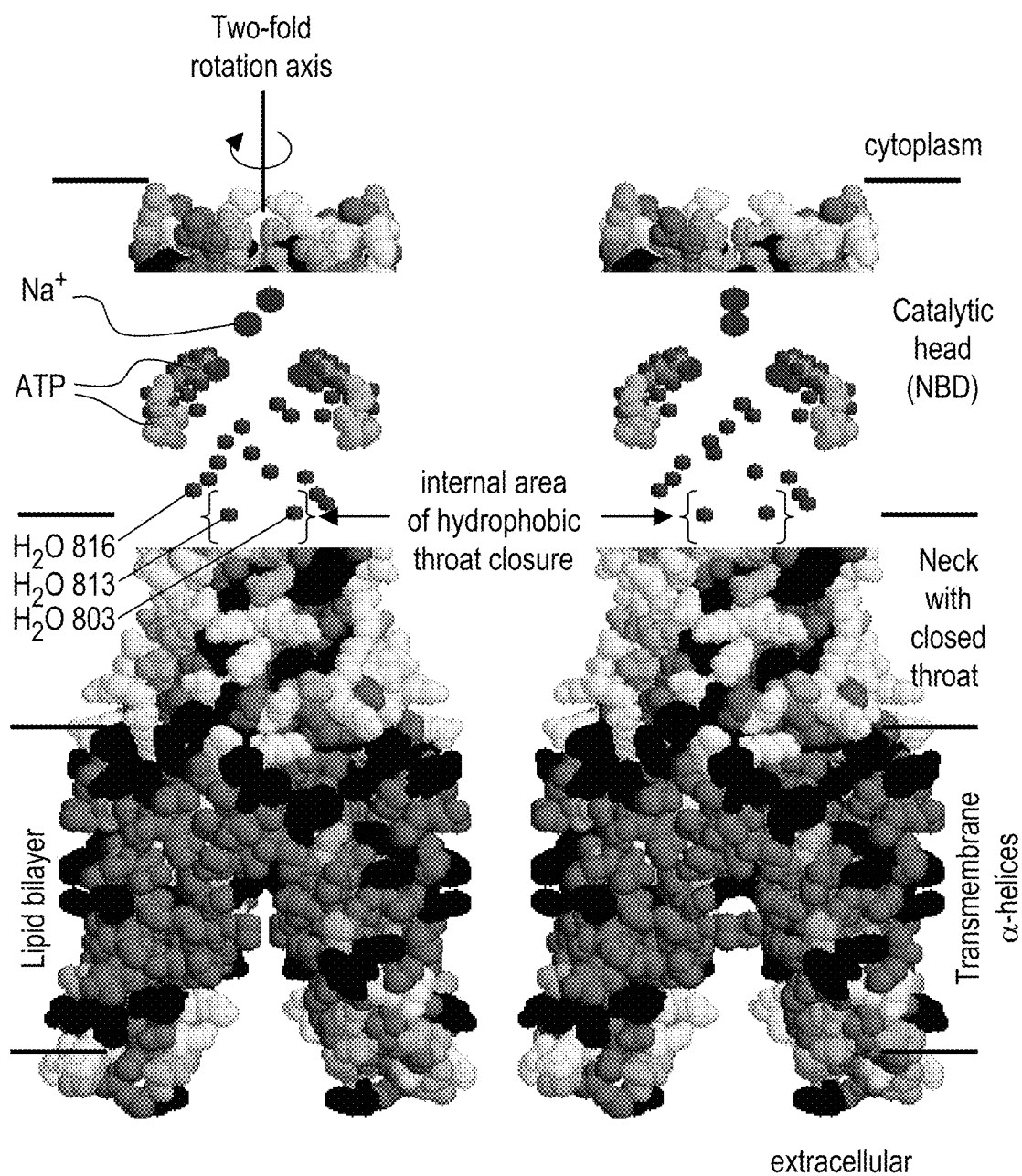
FIG. 10 is a cross-eye stereo view of Sav1866 (*Staphylococcus aureus* ABCB1 exporter protein) in full frontal view with semi-transparent ligand overlay, as it was to have appeared in (Urry et al., (Current Pharmaceutical Design vol. 15:2833-2867, 2009). The structure, a homodimer, is given in space-filling representation with white charged residues, light gray neutral residues, gray hydrophobic residues and black aromatic reaidues. It is viewed perpendicular to the vertical two-fold molecular axis as having three parts—the catalytic head (NBD, nucleotide binding domain with transparent overlay of internal ATP ligands and water seen in stereo), a neck with an internal hydrophobically closed throat, and twelve channel-forming transmembrane α-helices. Crystal structure accessible from the Protein Data Bank as structure file number 2ONJ due to Dawson and Locher (Dawson R J P, Locher K P. FEBS Ltrs 2007; 581: 935-8. Protein Data Bank, Accession Code 2ONJ).
Figure 11A:
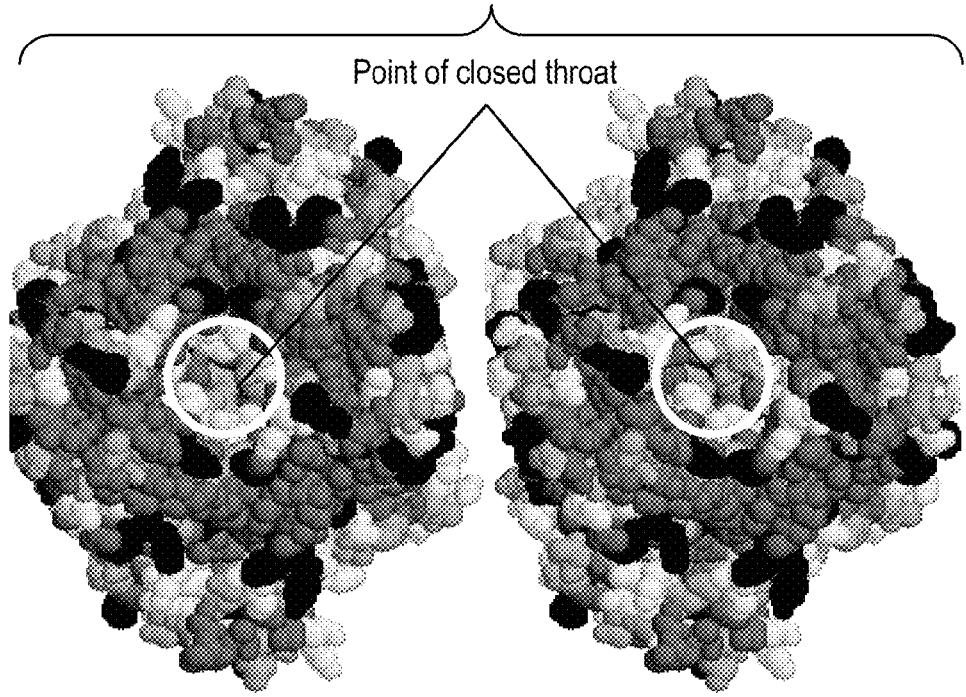
FIG. 11 is a structure (homodimeric) of the multidrug ABC exporter (Sav1866), membrane end view using space filling representation in cross-eye stereo view looking into the channel that is closed by hydrophobic association of residues V117$^{A\&B}$, V207$^{A\&B}$, H204$^{A\&B}$, L121$^{A\&B}$, and Y112$^{A\&B}$ at a band on the other side of which is the base of the aqueous cavern that has a continuous aqueous path to both NaATPs. A. complete channel view. B. Expanded for more detail and labeling of residues at closure. Protein Data Bank accession code 2ONJ due to Dawson and Locher (Dawson R J P, Locher K P. FEBS Ltrs 2007; 581: 935-8. Protein Data Bank, Accession Code 2ONJ).
Figure 11B:
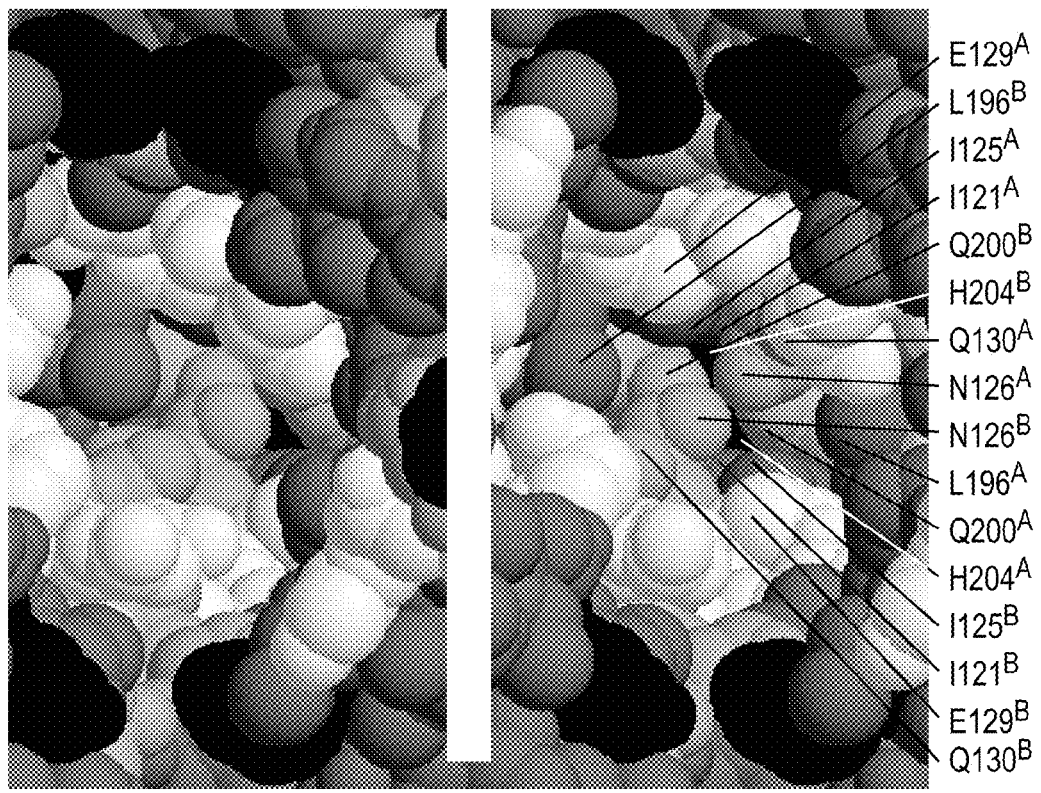
Figure 12:
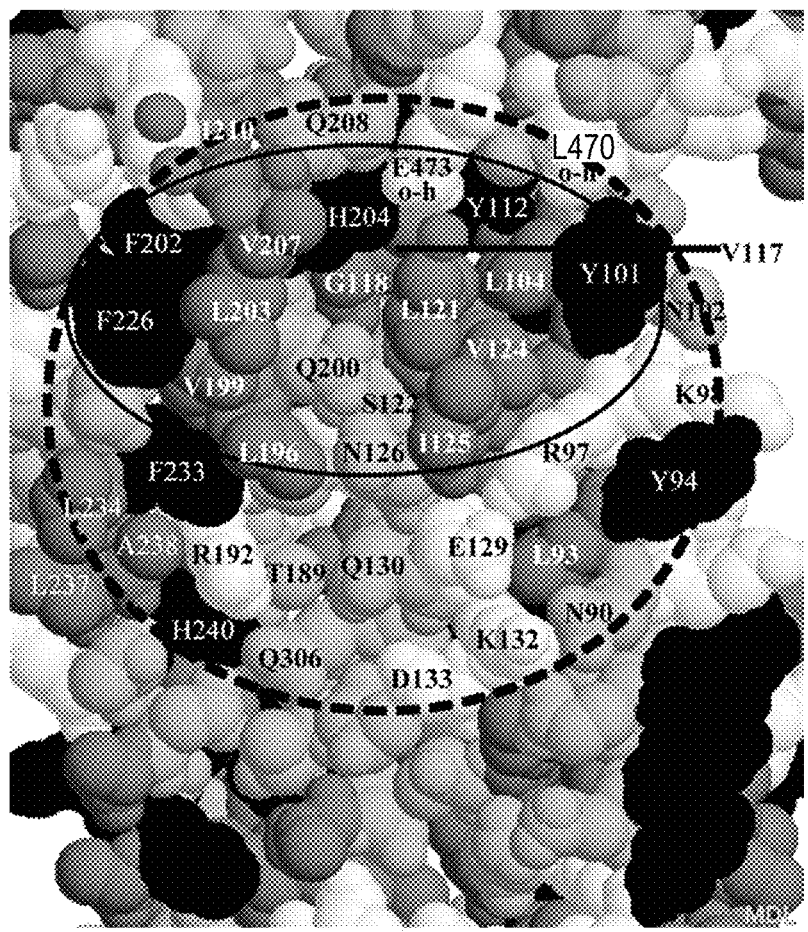
FIG. 12 is a structure of the B chain of the AB homodimer of multi-drug ABC exporter (Sav1866) showing hydrophobic (dark) area of closed throat within the neck, which throat is to be opened for transport by breakdown of 2ATP to 2ADP+2Pi achieving maximal apolar-polar repulsion, $\Delta$Gap. Residues V207$^{A\&B}$, H204A&B, V117$^{A\&B}$, and Y112$^{A\&B}$ are at the base of the aqueous cavern looking down from Pγ in FIG. 14. Residues H204$^{A\&B}$, I121$^{A\&B}$ and Q200$^{A\&B}$ are seen as the channel closes when viewed from outside the cell membrane in FIG. 11. Residues E473(o-h) and E470(o-h) of B chain overhang the hydrophobic surface depicted and are actually on other side of A chain. Protein Data Bank accession code 2ONJ due to Dawson and Locher (Dawson R J P, Locher K P. FEBS Ltrs 2007; 581: 935-8. Protein Data Bank, Accession Code 2ONJ).

The data for the naturally occurring amino acid residues are given in Table 1 and plotted in FIG. 2 in terms of $T_t$ versus $\Delta G°_{HA}$. The result is an interesting sigmoid-shaped curve, which may also serve to estimate $\Delta G_{HA}$ when only $T_t$ is known.

Comparisons for the hydrophobicities of the amino acid residues: From Table 1 we may note that the effect of the addition of a single —$CH_2$— moiety as occurs on replacement of Val by Leu gives a change of −1.55 kcal/mol-$CH_2$, again essentially that of the −1.5 kcal/mol-$CH_2$ found by Butler (Butler JAV Trans Faraday Soc 33:229-238, 1937) for the methanol to n-pentanol series discussed above. One should also note the large effect of ionization by comparing Glu(COOH) and Glu($COO^-$) with a $\Delta G_{HA}$ of 5.2 kcal/mol-pentamer and of Lys($NH_2$) and Lys($NH_3^+$) with a $\Delta G_{HA}$ of 3.5 kcal/mol-pentamer.

Furthermore a set of data for chemical attachment of a number of biologically relevant groups is given in Table 2. In this case most of the $\Delta G°_{HA}$ values have been obtained by taking the experimental $T_t$, suitably extrapolated to $f_\chi=1$ to obtain $T_t$, and reading the value of $\Delta G°_{HA}$ from the sigmoid curve of FIG. 13. Interesting are the changes in the value of $\Delta G_{HA}$ on reduction of an N-methyl nicotinamide (NMeN$^+$+

$H^+ + 2e^- \rightarrow NMeNH$) to give $-9$ kcal/mol, of nicotinamide adenine dinucleotide (i.e., $NADH^+ + H^+ + 2e^- \rightarrow NADH_2$) to give $-7.5$ kcal/mol, and of flavin adenine dinucleotide (i.e., $FAD + 2H^+ + 2e^- \rightarrow FADH_2$) to give $-4.5$ kcal/mol. The relative magnitudes of the foregoing biologically relevant groupings fit well with their biological roles, e.g., with respect to the roles of NAD and FAD in the electron transport chain of the inner mitochondrial membrane.

ECMPs are useful for designing drugs with a preferred drug hydrophobicity. Drugs are designed which to frustrate multi-drug resistance imparted by P-glycoprotein and microbial ABC exporter proteins. The inhibitors of P-glycoprotein are substantially hydrophobic molecules that bind by hydrophobic and aromatic interactions. Efforts to design drugs with a preferred drug hydrophobicity would be aided by an accurate means of quantifying the hydrophobicity of drugs designed to limit the capacity whereby simultaneous hydrolysis of two ATP to two ADP and two $HPO_4^{-2}$ could expel the drugs from the cell.

According to the $\Delta G_{ap}$ mechanism discussed above for the function of ABC exporter proteins—Sav1866 of *Staphylococcus aureus*, MsbA of *Salmonella typhimurium* and P-glycoprotein of mammals, the task of ABC exporter proteins is to disrupt hydrophobic associations in order to open a transit pathway through the cell membrane to the extracellular space. For Sav1866 disruption of hydrophobic association is a challenge that requires the simultaneous hydrolysis of two ATP molecules. A typical design modification for drugs as described herein is to increase the hydrophobicity of the drug to challenge the exporter protein's capacity to disrupt the hydrophobic associations required to open the channel to the outside of the cell and to move the drug through it.

Drug design is accomplished by the determination of $\Delta G_{HA}$(drug) using ECMP. With the derivation of $\Delta G_{HA}$, the change in Gibbs free energy for hydrophobic association and the use of the first ECMP basis set, it becomes possible by means of differential scanning calorimetry (DSC) to develop the $\Delta G_{HA}$-based Hydrophobicity Scales for amino acid residues (both in their charged and uncharged states), see Table 1, and for other chemical functionalities of biology, such as cofactors, coenzymes, prosthetic groups, phosphorylations, sulfations, nitrations, and so on, see Table 2. By the same approach, the hydrophobicities of drugs and hydrophobic modifications of drugs can be determined, and drug hydrophobicity tables can be prepared. Thus, for the first drug, Drug1($h_0$) with a reference hydrophobicity ($h_0$), there would be developed a table of hydrophobicity values with the entries, $\Delta G_{HA}$[Drug1($h_0$)], $\Delta G_{HA}$Drug1($h_1$), $\Delta G_{HA}$Drug1($h_2$), ... $\Delta G_{HA}$Drug1($h_n$). This series of hydrophobically modified drugs would then be examined for efficacy in destroying the pathogen or the human carcinoma cell, and for interfering with effectiveness of the ABCB1 exporter protein to pump the series—[Drug1($h_0$)], [Drug1($h_1$)], [Drug1($h_2$)], ... [Drug1($h_{n-1}$)], [Drug1($h_n$)]—out of the cell. One could then plot, for example, the ratio of (efficacy to destroy pathogen or diseased cell)/(rate of export from cell). The drugs having the larger values of the ratio become preferred candidate drugs. It should be appreciated that the preferred hydrophobicity for a given drug could differ, for example, for Sav1866 of *Staphylococcus aereus*, for MsbA of *Salmonella typhimurium*, and for human P-glycoprotein, as there are differences in the hydrophobicities of the hydrophobic gates and the hydrophobic binding of the drug at the substrate binding site.

The same considerations of a quantified optimization of drug hydrophobicity may be considered relevant to ABC transport proteins in general and even to drugs binding at whatever site. The $\Delta G_{HA}$-based Hydrophobicity Scale described herein is the only hydrophobicity scale that provides the desired change in Gibbs free energy for hydrophobic association.

Methods of Optimizing Drug Hydrophobicity

Methods of producing a therapeutic drug for treating or preventing a disease or condition that is capable of down-regulating exporter protein activity in a cell are described herein. In these methods, the hydrophobicity of a drug or candidate drug is optimized, resulting in a drug that is able to decrease or prevent exporter protein activity in a cell and thus decrease or prevent export of the drug from the cell. A typical method of producing a therapeutic drug for treating or preventing a disease or condition that is capable of down-regulating exporter protein activity in a cell includes the following steps. A drug that is used for treating or preventing the disease or condition or that is a candidate drug for treating or preventing the disease or condition is provided. The drug is modified to increase hydrophobicity of the drug, resulting in at least a first modified drug having a hydrophobicity higher than that of the drug. The drug or the at least first modified drug is modified to increase hydrophobicity of the drug or the at least first modified drug, resulting in at least a second modified drug having a hydrophobicity higher than that of the drug and that of the at least first modified drug. A change in Gibbs free energy for hydrophobic association-based hydrophobicity scale is used to determine the hydrophobicities of the drug, the at least first modified drug, and the at least second modified drug. The drug, the at least first modified drug and at least second modified drug are tested for efficacy of treating or preventing the disease or condition. In some embodiments, a value is assigned for efficacy for each of the drug, at least first modified drug and at least second modified drug. The drug, the at least first modified drug and at least second modified drug are tested for a capacity to decrease a rate of export of the drug, the at least first modified drug and at least second modified drug from a cell. A value can be assigned for the decreased rate of export for each of the drug, at least first modified drug and at least second modified drug. For each of the drug, the at least first modified drug and at least second modified drug, a ratio of the value for efficacy to the value for the decreased rate of export can be determined. In an embodiment wherein such a ratio is determined, the drug (of the drug, the at least one modified drug, and the at least second modified drug) having the highest ratio of value for efficacy to the value for the decreased rate of export is identified as a therapeutic drug for treatment or prevention of the disease or condition. In some embodiments, it is not necessary to determine a ratio as described above. In some embodiments, one can determine which of the drug, the at least one modified drug, and the at least second modified drug is best suited for a particular application based on either the efficacy of each, or the rate at which they are exported from a cell.

In a typical embodiment, the step of determining a ratio of the value for efficacy to the value for the decreased rate of export includes identifying an optimal hydrophobicity for down-regulating exporter protein activity in the cell. In the method, at least a third modified drug is produced and is tested. In some methods, at least a fourth modified drug is produced and is tested. In some embodiments, five or more (e.g., 5, 6, 7, 8, 10, 50, 100, 150, 200, etc.) modified drugs are produced before one is identified as an optimized therapeutic drug for treatment or prevention of a disease or condition. Generally, when administered to a cell, the therapeutic drug increases hydrophobic associations that are to be disrupted before opening of at least one transmembrane channel within at least one exporter protein in the cell, the at least one exporter protein activity conferring drug resistance to the cell. A therapeutic drug modified as described herein having an optimal hydrophobicity can have any hydrophobicity suitable for decreasing a rate of export of the drug, but generally has a hydrophobicity in the range of about −2 kcal/mole to about −20 kcal/mole. Therapeutic agents (drugs) described herein can be optimized for delivery to any type of cell, i.e., for preventing or decreasing activity of exporter proteins that would export the drug from the cell. For example, the cell can be a *Staphylococcus aureus* cell, and the at least one exporter protein can be Sav1866. In another example, the cell is a *Salmonella typhimurium* cell and the at least one exporter protein is MsbA. In a further example, the cell is a mammalian cell and the at least one exporter protein is a P-glycoprotein.

Down-regulating exporter protein activity typically includes reducing or preventing disruption of a hydrophobic association by simultaneous hydrolysis of two ATP molecules required for exporter protein activity in the cell. A disease to be treated or prevented using the compositions and methods described herein can be any disease or condition. For example, the disease or condition is cancer. In another example, the disease or condition is infection by a pathogen. Any suitable method can be used for increasing hydrophobicity of a therapeutic agent (e.g., drug). In a typical embodiment, increasing hydrophobicity of a therapeutic agent (e.g., drug) includes at least one of the following: adding one or more aliphatic groups, adding one or more aromatic groups, adding one or more heteroaromatic groups, and adding one or more of a combination thereof. A nonexhaustive list of additional examples of methods of increasing hydrophobicity of a therapeutic agent (e.g., drug) include: adding one or more methyl groups, adding one or more ethyl groups, adding one or more ethylene groups, adding one or more propyl groups, adding one or more propylene groups, adding one or more isopropyl groups, adding one or more isobutyl groups, adding one or more t-butyl groups, adding one or more cyclobutyl groups, adding one or more cyclopentyl groups, adding one or more cyclohexyl groups, adding one or more phenyl groups, adding one or more purine or pyrimidine group(s), adding one or more nicotinamide, and adding one or more flavinoid groups.

In one example of a method of producing a therapeutic drug for treating or preventing a disease or condition that is capable of down-regulating exporter protein activity in a cell, which exporter protein activity confers drug resistance on the cell, the method includes the following steps. A drug that is used for treating or preventing the disease or condition or that is a candidate drug for treating or preventing the disease or condition is provided. An ECMP with which to determine drug hydrophobicities is designed; the ECMP is based on (GVGVP) (SEQ ID NO:4) and utilizes the First ECMP basis set, which is written, in general, as poly[$f_V$(GVGVP),$f_X$ (GXGVP)] (SEQ ID NO:5), where $f_V$ and $f_X$ indicate the mole fractions of the composite pentamers in the polymer, i.e., $f_V+f_X=1$, and X is the functional residue to which the drug is to be bound, for example, either covalently by amide linkage to a glutamic acid or aspartic acid or to lysine or by disulfide linkage to a cysteine residue or by ion-pairing and hydrophobic association, ion-dipole and hydrophobic association, and dipole-dipole interactions and hydrophobic association, etc. For a=(GVGVP) (SEQ ID NO:4) and b≡(GXGVP) (SEQ ID NO:2), specific compositions might be written as $(aaaaabaaaa)_n$ for $f_X=0.1$, $(aabaaaabaa)_n$ for $f_X=0.2$, and $(aabaabaaba)_n$ for $f_X=0.3$, and so on where n is within the range of 10 to 400 or preferably 100 to 200. The ECMP is based on (GVGVP) (SEQ ID NO:4) and utilizes the Second ECMP basis set, which is written, in general, as given at the top of Table 3 for highly charged drugs such as sulfated or phosphorylated drugs, for example, Betamethazone phosphate, wherein the hydrophobicity of the ECMP itself must be increased by Val replaced by Phe to achieve the phase separation of hydrophobic association below physiological temperature. The hydrophobicities in terms of the change in Gibbs free energy for hydrophobic association, $\Delta G_{HA}$, of hydrophobic modifications to a base drug, e.g., Drug1, are determined. The change in Gibbs free energy is exactly the desired quantity for living organisms, because it is the free energy for conditions of constant temperature (T) and pressure (P) under which living organisms normally function. Determining the change in Gibbs free energy for hydrophobic association, $\Delta G_{HA}$ is achieved by a model protein system that exhibits an inverse temperature transition (ITT) to hydrophobic association on raising the temperature. The model system being used, the ECMP, is based on the repeating pentamer, $(GVGVP)_n$, (SEQ ID NO:4) and carefully designed analogues. The ECMP go from being essentially totally disordered random coils of pentamers, completely hydrated below the temperature of the ITT with the hydrophobic groups having their full complement of hydrophobic hydration, to essentially complete loss of hydrophobic hydration in the process of the phase separation called an inverse temperature transition (ITT). It is called an ITT because the model protein becomes more ordered on hydrophobic association, which would be contrary to the Second Law of Thermodynamics if it were not for the transition being driven by the overall increase in disorder as ordered (pentagonal rings of) hydrophobic hydration becomes disordered bulk water as hydrophobic groups associate.

In one embodiment the original drug with an initial hydrophobicity ($h_0$), designated as $Drug_1(h_0)$, is covalently bound as $Drug_1(h_0)$-ECMP at mole fraction $f_{D1}=0.1$ and dissolved in 0.15 N saline solution at pH 7.4 using 0.01 M phosphate and at low temperature below the onset of the inverse temperature transition. The differential scanning calorimetry (DSC) of the solution is determined to give $\Delta H_t[Drug_1(h_0)]$ at $f_{D1}=0.1$. This is repeated for $f_{D1}=0.2$ and $f_{D1}=0.3$. In general, a plot of $f_{D1}$ versus $\Delta H_t[Drug_1(h_0)]$ gives a straight line that includes the data points for $f_V=1$, and $f_{D1}=0.1$, $f_{D1}=0.2$ and $f_{D1}=0.3$, which allows linear extrapolation to $f_{D1}=1$. The heat of the transition at the intercept of $f_{D1}=1$ is bold-faced $\Delta H_t[Drug_t(h_0)]$ to indicate the change in heat in kcal/mol pentamer (GXGVP) (SEQ ID NO:2). The process is then repeated with $Drug_1(h_1)$ to obtain $\Delta H_t[Drug1_t(h_t)]$. The increase in hydrophobicity, i.e., in the change in Gibbs free energy for hydrophobic association, due to the drug modification becomes, $\Delta G_{HA}\{[Drug_1(h_0)]-[Drug_1(h_1)]\}=\Delta H_t[Drug_t(h_t)]-\Delta H_t[Drug_t(h_0)]$. The same is continued for $[Drug_1(h_2)]$, $[Drug_1(h_3)] \ldots [Drug_1(h_n)]$. To place these values on a scale in which $\Delta H_t$(GGGVP) (SEQ ID NO:11)=0, a quantity of −2.5 kcal/mol is added to all values of $\Delta H_t[Drug_1(h_j)]$. The same procedure is followed for a second drug, $Drug_2(h_0)$, and so on. The drug (e.g., Carboplatin (Systematic (IUPAC) name: azanide; cyclobutane-1,1-dicarboxylic acid; platinum) is modified by adding an appropriate functional group, (e.g., two methyl groups to give azanide; cyclobutane-3,3-dimethyl-1,1-dicarboxylic acid; platinum), resulting in at least a first modified drug having a hydrophobicity higher than that of the drug. This is an example of the kind of stepwise increase in hydrophobicity to be considered. The methods described herein provide the capacity to provide an accurate measure of the change in the Gibbs free energy for hydrophobic association, which provides the best opportunity to frustrate of the ABC exporter protein responsible for multi-drug resistance while allowing the drug to yet function in the destruction of the pathogen or of the mammalian carcinoma cell. This can be extended to all ABC transporter proteins and generalized to the optimization of all drugs at their site of action.

The drug or the at least first modified drug is modified by adding an appropriate functional group (e.g., phenyl group to Carboplatin to give azanide; cyclobutane-3-phenyl-1,1-dicarboxylic acid; platinum), resulting in at least a second modified drug having a hydrophobicity higher than that of the drug and that of the at least first modified drug. Another example of a drug, $Drug_2(h_0)$, is Oxaliplatin (Systematic (IUPAC) name: (R,R)-1,2-diaminocyclohexane(ethanedioate-O,O)platinum). The change in composition of the drug for an increased hydrophobicity can be denoted as $Drug_2(h_1)$. In the example of Oxaliplatin, increases in hydrophobicity could be increased by steps of an added methyl, for example, Systematic (IUPAC) name: (R,R)-1,2-diamino-4-methylcyclohexane(ethanedioate-O,O)platinum, and then a second methyl as in Systematic (IUPAC) name: (R,R)-1,2-diamino-4,5-dimethylcyclohexane(ethanedioate-O,O)platinum. Both Carboplatin and Oxaliplatin are reported to destroy cancerous cells by cross-linking DNA and both are exported from the cell by P-glycoprotein, thereby conferring multi-drug resistance that is to be frustrated.

The drug, the at least first modified drug and at least second modified drug are tested for efficacy of treating or preventing the disease or condition, and a value is assigned for efficacy for each of the drug, at least first modified drug and at least second modified drug. The drug is tested for its capacity to slow (frustrate) the rate export of the drug from the cell with a competent ABC exporter protein that confers drug resistance, the at least first modified drug and at least second modified drug for rate of export from a cell, and a value is assigned for the rate of export for each of the drug, at least first modified drug and at least second modified drug. For each of the drug, the at least first modified drug and at least second modified drug, a ratio of the value for efficacy of drug action to the value for the rate of drug export is determined, wherein one of the drug, the at least one modified drug, and the at least second modified drug having the highest ratio of value for efficacy to the value for the rate of export from the cell is identified as a therapeutic drug for treatment or prevention of the disease or condition.

Compositions Including Therapeutic Agents With Optimized Hydrophobicities

Described herein are compositions including therapeutic agents (e.g., drugs) having optimized hydrophobicities for decreasing or preventing exporter protein activity in a cell. A typical composition includes a therapeutic drug produced by the following steps. The hydrophobicity of a drug or candidate drug is optimized, resulting in a drug that is able to decrease or prevent exporter protein activity in a cell and thus decrease or prevent export of the drug from the cell. A typical method of producing a therapeutic drug for treating or preventing a disease or condition that is capable of down-regulating exporter protein activity in a cell includes the following steps. A drug that is used for treating or preventing the disease or condition or that is a candidate drug for treating or preventing the disease or condition is provided. The drug is modified to increase hydrophobicity of the drug, resulting in at least a first modified drug having a hydrophobicity higher than that of the drug. The drug or the at least first modified drug is modified to increase hydrophobicity of the drug or the at least first modified drug, resulting in at least a second modified drug having a hydrophobicity higher than that of the drug and that of the at least first modified drug. A change in Gibbs free energy for hydrophobic association-based hydrophobicity scale is used to determine the hydrophobicities of the drug, the at least first modified drug, and the at least second modified drug. The drug, the at least first modified drug and at least second modified drug are tested for efficacy of treating or preventing the disease or condition. In some embodiments, a value is assigned for efficacy for each of the drug, at least first modified drug and at least second modified drug. The drug, the at least first modified drug and at least second modified drug are tested for a capacity to decrease a rate of export of the drug, the at least first modified drug and at least second modified drug from a cell. A value can be assigned for the decreased rate of export for each of the drug, at least first modified drug and at least second modified drug. For each of the drug, the at least first modified drug and at least second modified drug, a ratio of the value for efficacy to the value for the decreased rate of export can be determined. In an embodiment wherein such a ratio is determined, the drug (of the drug, the at least one modified drug, and the at least second modified drug) having the highest ratio of value for efficacy to the value for the decreased rate of export is identified as a therapeutic drug for treatment or prevention of the disease or condition.

A therapeutic drug produced by this method typically has a hydrophobicity of about −2 kcal/mole to about −20 kcal/mole, and is capable of reducing or preventing export of the drug from a cell by exporter proteins. In a composition, the therapeutic drug is present at a concentration sufficient for decreasing or preventing disruption of hydrophobic associations required for opening of at least one transmembrane channel within at least one exporter protein in the cell. Therapeutic agents (drugs) described herein can be optimized for delivery to any type of cell, i.e., for preventing or decreasing activity of exporter proteins that would export the drug from the cell. For example, the cell can be a *Staphylococcus aureus* cell, and the at least one exporter protein can be Sav1866. In another example, the cell is a *Salmonella typhimurium* cell and the at least one exporter protein is MsbA. In a further example, the cell is a mammalian cell and the at least one exporter protein is a P-glycoprotein. In a typical embodiment, the therapeutic drug treats or prevents cancer or infection by a pathogen.

Synthesis of Nanoparticles Conjugated to Peptides or Polypeptides

Nanoparticles for delivering a cargo to a specific cell type and for promoting an immune response against a particular pathogen, antigen or cancer are described herein. A typical method of synthesizing nanoparticles conjugated to an antigen peptide or protein is as follows. As shown in FIG. 1 part 1, $(GVGVP)_{251}$ (SEQ ID NO:3) represents the base elastic-contractile model protein in this case of 251 repeats of the base pentamer, that is, a model protein of uniform chain length of 1255 amino acid residues and a molecular weight of 102,659 Daltons. This was made by means of recombinant DNA technology using standard techniques as described in the following paragraphs.

No new specialized techniques were required for the use of recombinant DNA technology in the production of protein-based polymers. A basic monomer gene or a gene segment is chosen such that the total length would be no more than about 150 bases, encoding for a sequence of 50 amino acid residues. In general, when designing a gene to be expressed in *E. coli*, the codon preferences for *E. coli* are used, whereas if the desire is to produce the polymer in tobacco, the codon preferences for tobacco are used. Thus one designs a DNA sequence for a basic monomer gene, including the sequences of the restriction sites as required for the protein to be expressed and the plasmid to be used. The next step is to prepare the full-length double-stranded 150 base pair monomer gene with additional bases for defined restriction sites as required for insertion into a given plasmid or vector. This begins with chemical synthesis of two base sequences of 80 to 90 bases, one from the 3' end and the other from the 5' end. The chemically synthesized sequences pair with each other using the overlap in their central region. Then the remarkable polymerase chain reaction (PCR, of forensic and other frame) completes the double strand. An appropriate strain of bacteria (e.g., *E. coli*) is for the transformation and growing up of the transformed *E. coli* containing many plasmids, each plasmid with one copy each of the monomer gene. The plasmids are harvested, the monomer genes excised by the appropriate restriction enzyme(s), and the sequence of the monomer gene verified.

Using appropriate oligonucleotide adaptors and ligase enzyme, the monomer genes are polymerized. This is called concatenation or concatemerization. The result can be a series of genes containing repeats of the monomer gene. Each band in lane 2 is a gene differing in size by one monomer gene (See FIG. 13 of D. W. Urry, A. Nicol, D. T. McPherson, C. M. Harris, T. M. Parker, J. Xu, D. C. Gowda and P. R. Shewry "Properties, Preparations and Applications of Bioelastic Materials." In *Encyclopedic Handbook of Biomaterials and Bioengineering—Part A—Materials*, Vol. 2, D. L. Wise, D. J. Trantolo, D. E. Altobelli, M. J. Yazemski, J. D. Gresser and E. R. Schwartz, Eds. Marcel Dekker, Inc., New York, pp. 1619-1673, 1995). Also, in the particular concatenation for polymerizing of $(GVGVP)_{10}$ (SEQ ID NO:21), the carboxyl end restriction site is used that adds another GVGVP, such that the final gene encodes for $(GVGVP)_{n \times 10+1}$ (SEQ ID NO:4) or $[(GVGVP)_{10}]n$ (GVGVP) (SEQ ID NO:22).

Having constructed the gene, it is now excised and inserted into an expression vector. The expression vector then is used to transform a strain of *E. coli* that is specialized for expression of the designed protein-based polymer. A portion of transformed *E. coli*, stored in a glycerol stock, is used to grow an inoculum for addition to a large fermentor. The choice of media depends on the strain of microbe and chosen expression vector. It generally includes a chemical inducer to turn on the expression, a carbon source (e.g., glucose or glycerol), a nitrogen source (often as a source of amino acids), salts, other cofactors as may be provided, for example, by a yeast extract, and an antibiotic to which the transformed *E. coli* are selectively resistant. The fermentor conditions are optimized with respect to O2 flow, stirring rate, pH, and so forth as required for the expression system. Fermentors ranging in size from a few liters to thousands of liters are commercially available. The product is $(GVGVP)_{251}$. For production by *E. coli* there is an important issue of the removal of *E. coli* toxic proteins. Because poly(GVGVP) (SEQ ID NO:4) has been chemically synthesized and adequately purified, it was established that these elastic protein-based polymers exhibited extraordinary biocompatibility (Dan W. Urry, Asima Pattanaik, Mary Ann Accavitti, Chi-Xiang Luan, David T. McPherson, Jie Xu, D. Channe Gowda, Timothy M. Parker, Cynthia M. Harris, and Naijie Jing, "Transductional Elastic and Plastic Protein-based Polymers as Potential Medical Devices," in *Handbook of Biodegradable Polymers*, ed. by Domb, Kost, and Wiseman, Harwood Academic Publishers, Chur, Switzerland, pp. 367-386, 1997).

Now the First ECMP Basis Set can be indicated, in general, in terms of pentamer compositions as poly[$f_V$(GVGVP),$f_X$(GXGVP)] (SEQ ID NO:5) where $f_V + f_X = 1$, that is, a formula $f_V = 0.9$ and $f_X = 0.1$ means a polymer with 9 (GVGVP) (SEQ ID NO:4) pentamers for every one (GXGVP) (SEQ ID NO:2) pentamer. By means of membrane dialysis, the chemically synthesized polymers have mean molecular weights of the order of 82,000 Daltons. When preparation is by biosynthesis, the ECMP are of one fixed length and the repeating sequence may be most commonly of six pentamers, but often ten pentamers, and sometimes nine or even twelve pentamers. A particular family of six repeating pentamers, i.e., a poly (30 mer), constitutes the Second ECMP Basis Set as listed below:

```
Model protein i:
                                        (SEQ ID NO: 16)
[GVGVP GVGVP GΦGVP GVGVP GVGVP GVGVP]n; Φ/0F Model protein ii:
                                        (SEQ ID NO: 17)
[GVGVP GVGFP GΦGFP GVGVP GVGVP GVGVP]n; Φ/2F Model protein iii:
                                        (SEQ ID NO: 18)
[GVGVP GVGVP GΦGVP GVGVP GVGFP GFGFP]n; Φ/3F Model protein iv:
                                        (SEQ ID NO: 19)
[GVGVP GVGFP GΦGFP GVGVP GVGFP GVGFP]n; Φ/4F Model protein v:
                                        (SEQ ID NO: 20)
[GVGVP GVGFP GΦGFP GVGVP GVGFP GFGFP]n; Φ/5F
```

The pKa and positive cooperativity values for the Φ functional groups of glutamic acid (Glu, E) and lysine (Lys, K) for this family of ECMP are given in Table 3 where the hydrophobic-induced reduction potential and positive cooperativity shifts are listed. The F represents the phenylalanine (Phe) residue having in the design replaced a V (valine, Val) residue. These polymers were biosynthesized using recombinant DNA technology and expressed by *E. coli* fermentation.

Decoration of the surface of drug-laden ECMP nanoparticles as described herein is useful for the purpose of targeting the drug delivery vehicle to the desired cell for localized drug release. One example of an entity with which to target would be synthetic antigen-binding Fab1-Fab2 fragments that target cancerous cells with up-regulated estrogen receptors. HIGH AFFINITY MONOCLONAL ANTIBODY FOR RECOGNIZING THE ESTROGEN RECEPTOR (ER) AND METHOD FOR CREATING THE ANTIBODY is taught in U.S. Pat. No. 7,148,332, and in U.S. Pat. No. 7,745,230 "ESTROGEN RECEPTORS AND METHODS OF USE CONTINUING APPLICATION DATA" which application claims the benefit of U.S. Provisional Application Ser. No. 60/552,067, filed 10 Mar. 2004, and 60/643,469, filed 13 Jan. 2005, and is under study, e.g., Use of a Monoclonal Anti-Estrogen Receptor Antibody in the Immunohistochemical Evaluation of Human Tumorsl, Cancer Research (Suppl.) 46, 4244s-4248s, August 1986, Kenneth S. McCarty, Jr., Eva Szabo, Julie L. Flowers, Edwin B. Cox, George S. Leight, Larry Miller, John Konrath, John T. Soper, Debra A. Budwit, William T. Creasman, lilluni F. Seigier, and Kenneth S. McCarty, Sr.; and Immunocytochemical Analysis of Estrogen Receptors as a Predictor of Prognosis in Breast Cancer Patients: Comparison with Quantitative Biochemical Methods1 Cancer Research 49, 1052-1056, Feb. 15, 1989, Laura B. Kinsel, Eva Szabo, Geoffrey L. Greene, John Konrath, George S. Leight, and Kenneth S. McCarty, Jr. Also, sequences of Fab1 and Fab2 fragments for binding to the estrogen receptor may be obtained by such as The Kabat Database of Sequences of Proteins of Immunological Interest. The Fab 1 and Fab2 sequences would be added to the DNA sequence, each for a designed ECMP, such that the amino end of ECMP sequences would be contiguous with the carboxyl end of the Fab. These Fab-ECMP would be incorporated into the drug-delivery nanoparticle at the desired percentage of surface coverage.

To give a sense of the length of the ECMP in comparison with the nanoparticle diameter, if laid out in the dynamic β-spiral conformation, the ECMP would be longer than the diameter of a 50 nm diameter nanoparticle. Now the 1.8 nm diameter β-spiral conformation can fold back on itself and it is believed that three β-spirals supercoil to form a twisted filament of 5 nm diameter that can be seen in electron micrographs of negatively stained filaments (See FIGS. 5, 6, and 7 of Dan W. Urry, "Free Energy Transduction in Polypeptides and Proteins Based on Inverse Temperature Transitions," *Prog. Biophys. Molec. Biol.* 57, 23-57, 1992). Furthermore, as seen in FIGS. 25 and 26, the dimensions of the synthetic antigen-binding Fab1-Fab2 fragment, based on crystallographic data, would be 7 nm in length and grossly characterized as an elliptical cylinder with a 5.2 nm major axis and 3.3 nm minor axis that would jut out of the spherical nanoparticle along the axis of a diameter.

50 nm diameter cationic drug delivery nanoparticles (ECMPdd) were constructed (See FIG. 24). These nanoparticles were of the ECMP, $(GVGVP\ GVGFP\ GEGFP\ GVGVP\ GVGFP\ GFGFP)_{42}$ (GVGVP) (SEQ ID NO:7), which is 253 pentamers. The ECMP $(GVGVP\ GVGFP\ GKGFP\ GVGVP\ GVGFP\ GFGFP)_{45}$ (GVGVP) (SEQ ID NO:23) was also constructed. By way of example, one gene will be constructed by utilizing the appropriate restriction site to attach the gene for Fab1 to the DNA sequence encoding for a protein-based polymer to give Fab1-$(GVGVP\ GVGFP\ GEGFP\ GVGVP\ GVGFP\ GFGFP)_{42}$ (GVGVP) (SEQ ID NO:7) labeled (ECMPdd/Fab 1). A second gene will be prepared to produce Fab2-$(GVGVP\ GVGFP\ GKGFP\ GVGVP\ GVGFP\ GFGFP)_{45}$ (GVGVP) (SEQ ID NO:23), identified as (Fab2ECMPdd). Then the gene products, $ECMP^{-}$dd/Fab1 and $ECM^{P+}$dd/Fab2, are to be combined in a 1:1 ratio in dilute solution to form the associated $ECMP^{-}$dd/Fab1-Fab2$ECM^{P+}$ dd, yielding synthetic antigen binding fragments oriented appropriately to bind the antigenic site of an upregulated receptor of a cancerous cell.

The $ECMP^{-}$dd/Fab 1-Fab2$ECMP^{+}$dd are added to the particular ECMPdd at a ratio to give the desired extent of decoration on the surface of the nanoparticle and the properties of the ECMP are such that they exclude the more polar Fab1-Fab2 protein by an apolar-polar repulsive free energy of hydration, ΔGap, from the interior to the charged surface of the nanoparticle. The surface area of a 50 nm diameter is 7,854 $nm^2$, and the area occupied by the Fab1-Fab2 is about 53 $nm^2$ such that 10% coverage of the surface would involve 15 Fab1-Fab2 constructs and 20% coverage of the surface would require 30 Fab1-Fab2 constructs. Each surface construct, a synthetic antigen-binding fragment, could be grossly described as a cylinder 7 nm in length aligned on a radial extension pointing directly out of the spherical nanoparticle surface (See FIG. 26). The cylinder may be approximated with an elliptical cross-section of a 5.2 nm major axis and a 3.3 nm minor axis with the major axis twisted by about 100° (See FIG. 25). The distal end of the cylinder would contain the antigen-binding site, which is seen in gray scale as a largely black end of the cylinder, that is an extremely hydrophobic end inserts into the antigenic site of the receptor (See FIG. 25).

Construction of ECMP-nanoparticles (ECMPddnp) for Controlled Drug Release

By way of example a most hydrophobic composition with all V replaced by F will be used which would give the lowest, most-prolonged release profile. This is the example of the bottom curve in FIG. 3 of $(GFGFP\ GEGFP\ GFGFP\ GFGFP\ GEGFP\ GFGFP)_n$ (SEQ ID NO:24). Then subsequent less hydrophobic ECMP can be considered by simply decreasing the number of V replaced by F. The n for $(GFGFP\ GEGFP\ GFGFP\ GFGFP\ GEGFP\ GFGFP)_n$ (SEQ ID NO:24), labeled $ECMP_{2E/10F}$, could vary from 0.5 to 100, but for the nanoparticle purposes considered here 30 to 60 would be preferred. The nanoparticle size is dependent on the temperature and concentration at which quenching is carried out (F. Sciortino, M. U. Palma, D. W. Urry and K. U. Prasad, "Nucleation and Accretion of Bioelastomeric Fibers at Biological Temperatures and Low Concentrations," *Biochem. Biophys. Res. Commun.* 157, 1061-1066, 1988.), and, due to the E residue, on the pH (Dan W. Urry, ShaoQing Peng, Jie Xu, and David T. McPherson, "Characterization of Waters of Hydrophobic Hydration by Microwave Dielectric Relaxation," J. Amer. Chem. Soc. 119, 1161-1162, 1997.).

Cross-linking by cobalt 60 of a relatively lower dose than the common 20 Mrads used for $(GVGVP)_{\sim 200}$ (SEQ ID NO:25), say 2 to 8 Mrads, which with a lessened call for elastic modulus, fewer cross-links would allow for greater swelling for uptake of the FabECMP, discussed below. By adding a K (lysine, Lys) residue at a suitable interval, for example, $(GFGFP\ GEGFP\ GFGFP\ GFGFP\ GEGFP\ GFGFP\ GFGFP\ GKGFP\ GFGFP\ GFGFP\ GEGFP\ GFGFP)_n$ (SEQ ID NO:26), labeled $ECMP_{1K3E/20F}$, cross-linking can be achieved by a water soluble carbodiimide as used in Dan W. Urry, Jie Xu, Weijun Wang, Larry Hayes, Frederic Prochazka, and Timothy M. Parker, "Development of Elastic Protein-based Polymers as Materials for Acoustic Absorption." *Mat. Res. Soc. Symp. Proc.*: Materials Inspired by Biology, 774, 81-92, 2003 (See section Mechanical Properties of Cross-linked Fibers). The ratio, $ECMP_{2E/10F}$:$ECMP_{1K3E/20F}$ can be varied to control extent of chemical cross-linking. The pH of the reaction mixture is also relevant. It should be noted that the pK of the carboxylate of $ECMP_{2E/10F}$ would be of the order of 6.2 (See FIG. 4) and that of the K residue will also be shifted toward physiological pH. These polymers can each be ionized, which leads to ion-pairing making ease of cross-linking to form an amide cross-link. A cross-linked 1:1 ratio would result in a nanoparticle for carrying cationic drugs. The D (aspartic acid, Asp) residue could, of course, also be used for the negative. Formation of an ECMPddnp for an anionic drug carrier would utilize K and/or R (argenine, Arg) and/or H (histidine, His) and would utilize fewer F residues, because of the lower solubility provided by the positive charges of K and/or R and/or H.

The loading of the nanoparticles with drug is assisted by determining loading profiles on non-cross-linked ECMP as demonstrated in FIG. 4 for a series of compositions of increasing hydrophobicity. The ECMP is dissolved in normal saline at pH 7.4. A small amount of drug is then added and the onset temperature of phase separation is determined as shown in FIG. 1B. This is continued stepwise for a given composition, e.g., K/0F, and then is repeated for a more hydrophobic polymer until a loading profile as in FIG. 4 is obtained. This determines which compositions can be used for the particular drug. This, with the pK of the functional group of the ECMP, provides information on the relative release rates that will occur, and with the release rate of one composition and the pK of each composition the release rate for each composition can be approximated. The chosen ECMP or the several of the most interesting ECMPs are then made into nanoparticles and the conditions for loading have been determined.

Construction of Nanoparticles (ECMPddnp/p1p2) for Drug Delivery to Cells

Described herein are nanoparticles that are effective vehicles for delivering a therapeutic agent (e.g., a drug) to cells with a preferred release rate. While there are numberless means for achieving cell targeting and for constructing the ECMP nanoparticle, the method discussed below is one well-suited for the special properties of (GVGVP) (SEQ ID NO:4)-based ECMP. The ECMP are constructed by means of recombinant DNA technology, as described above. This allows simultaneous integration of the synthetic antigen-binding fragments, Fab 1 and Fab2, with the ECMPddnp. Following the Fab fragment labeling of Uysal et al (S. Uysal, V. Vasquez, V. Tereshko, K. Esaki, F. A. Fellouse, S. S. Sidhu, S. Koide, E. Peroz and A. Kossiakoff( ) *Proc. Natl. Acad. Sci. USA,* 2009, 106, 6644-6649. Protein Data Bank accession code 3EFF. In our example the compositions discussed above will be used, i.e., Fab1-(GFGFP GEGFP GFGFP GFGFP GEGFP GFGFP GFGFP GKGFP GFGFP GFGFP GEGFP GFGFP (SEQ ID NO:26), labeled Fab1-ECMP$_{1K3E/20F}$, and Fab2-(GFGFP GEGFP GFGFP GFGFP GEGFP GFGFP)$_{2n}$ (SEQ ID NO:27), labeled ECMP$_{2(2E/10F)}$, and the ECMP will be added to solution at a 1:1 ratio.

Using Quasi-elastic light scattering (QELS) and quenching, the correct conditions for achieving the desired particle size are determined (F. Sciortino, M. U. Palma, D. W. Urry and K. U. Prasad, "Nucleation and Accretion of Bioelastomeric Fibers at Biological Temperatures and Low Concentrations," *Biochem. Biophys. Res. Commun.* 157, 1061-1066, 1988). And conditions will be used that result in Fab1-Fab2 assembly to result in each Fab being attached to each other and to their respective chains.

The pseudo dimers composed of Fab1-(GFGFP GEGFP GFGFP GFGFP GEGFP GFGFP GFGFP GKGFP GFGFP GFGFP GEGFP GFGFP)$_n$ (SEQ ID NO:26), Fab2-(GFGFP GEGFP GFGFP GFGFP GEGFP GFGFP)$_{2n}$(SEQ ID NO:27), coupled via the Fab1-Fab2 will be added to the weakly cross-linked nanoparticles described immediately above and incorporated into the weakly cross-linked nanoparticle by swelling and contracting.

Other Embodiments

Any improvement may be made in part or all of the compositions and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A process for optimizing a therapeutic drug to reduce or prevent export of the therapeutic drug from a cell by an exporter protein, the method comprising the steps of:
   a) measuring hydrophobicity of the therapeutic drug by measuring $\Delta G_{HA(drug)}$;
   b) generating a modified therapeutic drug by modifying the therapeutic drug to increase the hydrophobicity of the therapeutic drug;
   c) measuring hydrophobicity of the modified therapeutic drug by measuring $\Delta G_{HA(modified\ drug)}$, and determining a change in hydrophobicity $\delta\Delta G_{HA}$ calculated as $\Delta G_{HA(modified\ drug)} - \Delta G_{HA(drug)}$; and
   d) determining a change in rate of export from the cell of the modified therapeutic drug compared to the therapeutic drug;
wherein the modified therapeutic drug becomes an optimized therapeutic drug when the modified therapeutic drug upon administration to the cell decreases or prevents disruption of hydrophobic associations required for opening of a transit pathway within the exporter protein in the cell.

2. The process of claim 1, wherein the hydrophobicity $\Delta G_{HA}$ of the optimized therapeutic drug is in a range of about −2 kcal/mol to about −20 kcal/mol.

3. The process of claim 1, wherein the exporter protein is an ATP-binding cassette protein.

4. The process of claim 1, wherein the cell is a *Staphylococcus aureus* cell and the exporter protein is Sav1866.

5. The process of claim 1, wherein the cell is a *Salmonella typhimurium* cell and the exporter protein is MsbA.

6. The process of claim 1, wherein the cell is a mammalian cell and the exporter protein is a P-glycoprotein.

7. The process of claim 1, wherein the decreasing or preventing disruption of hydrophobic associations comprises a simultaneous hydrolysis of two ATP molecules required for activity of the exporter protein in the cell.

8. An optimized therapeutic drug capable of reducing or preventing export of the therapeutic drug from a cell by an exporter protein, the optimized therapeutic drug prepared according to the process of claim 1.

9. The optimized therapeutic drug of claim 1, wherein the optimized therapeutic drug treats or prevents a cancer or an infection by a pathogen.

10. A process for optimizing a therapeutic drug to reduce or prevent export of the therapeutic drug from a cell by an exporter protein, the method comprising the steps of:
    a) measuring hydrophobicity of the therapeutic drug by measuring a $\Delta_{HA(drug)}$; and
    b) modifying the therapeutic drug to generate a modified therapeutic drug with a hydrophobicity measured as $\Delta G_{HA(modified\ drug)}$ such that a change in hydrophobicity of $\delta\Delta G_{HA}$ calculated as $\Delta G_{HA(modified\ drug)} - \Delta G_{HA(drug)}$ falls between the range of about −2 kcal/mol to about −20 kcal/mol;
wherein the modified therapeutic drug becomes an optimized therapeutic drug when the modified therapeutic drug upon administration to the cell decreases or prevents disruption of hydrophobic associations required for opening of a transit pathway within the exporter protein in the cell.

11. The process of claim 10, wherein the cell is a *Staphylococcus aureus* cell and the exporter protein is Sav1866, or a *Salmonella typhimurium* cell and the exporter protein is MsbA.

12. The process of claim 10, wherein the cell is a mammalian cell and the exporter protein is a P-glycoprotein.

13. The process of claim 10, wherein the decreasing or preventing disruption of hydrophobic associations comprises a simultaneous hydrolysis of two ATP molecules required for activity of the exporter protein in the cell.

* * * * *

SEQUENCE LISTING

```
<160> NUMBER OF SEQ ID NOS: 27

<210> SEQ ID NO 1
<211> LENGTH: 30
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (12)..(12)
<223> OTHER INFORMATION: Xaa can be any naturally occurring amino acid

<400> SEQUENCE: 1

Gly Val Gly Val Pro Gly Val Gly Val Pro Gly Xaa Gly Val Pro Gly
1               5                   10                  15

Val Gly Val Pro Gly Val Gly Val Pro Gly Val Gly Val Pro
            20                  25                  30

<210> SEQ ID NO 2
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (2)..(2)
<223> OTHER INFORMATION: Xaa can be any naturally occurring amino acid

<400> SEQUENCE: 2
```

```
Gly Xaa Gly Val Pro
1               5

<210> SEQ ID NO 3
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(5)
<223> OTHER INFORMATION: pentamer repeated 251 times

<400> SEQUENCE: 3

Gly Val Gly Val Pro
1               5

<210> SEQ ID NO 4
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Gly Val Gly Val Pro
1               5

<210> SEQ ID NO 5
<211> LENGTH: 10
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Gly Val Gly Val Pro Gly Xaa Gly Val Pro
1               5                   10

<210> SEQ ID NO 6
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 6

Tyr Gly Gly Phe Leu
1               5

<210> SEQ ID NO 7
<211> LENGTH: 35
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(30)
<223> OTHER INFORMATION: the first 30 residues are repeated 42 times

<400> SEQUENCE: 7

Gly Val Gly Val Pro Gly Val Gly Phe Pro Gly Glu Gly Phe Pro Gly
1               5                   10                  15
```

```
Val Gly Val Pro Gly Val Gly Phe Pro Gly Phe Gly Phe Pro Gly Val
            20                  25                  30

Gly Val Pro
        35

<210> SEQ ID NO 8
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 8

Gly Val Gly Ile Pro
1               5

<210> SEQ ID NO 9
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (2)..(2)
<223> OTHER INFORMATION: Xaa can be any naturally occurring amino acid

<400> SEQUENCE: 9

Gly Xaa Gly Val Pro
1               5

<210> SEQ ID NO 10
<211> LENGTH: 10
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (2)..(2)
<223> OTHER INFORMATION: Xaa can be any naturally occurring amino acid

<400> SEQUENCE: 10

Gly Xaa Gly Val Pro Gly Val Gly Val Pro
1               5                   10

<210> SEQ ID NO 11
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 11

Gly Gly Gly Val Pro
1               5

<210> SEQ ID NO 12
<211> LENGTH: 15
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 12

Gly Val Gly Phe Pro Gly Glu Gly Phe Pro Gly Val Gly Val Pro
1               5                   10                  15
```

```
<210> SEQ ID NO 13
<211> LENGTH: 30
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 13

Gly Glu Gly Val Pro Gly Val Gly Val Pro Gly Val Gly Phe Pro Gly
1               5                   10                  15

Phe Gly Phe Pro Gly Val Gly Val Pro Gly Val Gly Val Pro
            20                  25                  30

<210> SEQ ID NO 14
<211> LENGTH: 15
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 14

Gly Phe Gly Phe Pro Gly Glu Gly Phe Pro Gly Phe Gly Phe Pro
1               5                   10                  15

<210> SEQ ID NO 15
<211> LENGTH: 10
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (9)..(9)
<223> OTHER INFORMATION: Xaa can be any naturally occurring amino acid

<400> SEQUENCE: 15

Val Pro Gly Val Gly Val Pro Gly Xaa Gly
1               5                   10

<210> SEQ ID NO 16
<211> LENGTH: 34
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 16

Gly Val Gly Val Pro Gly Val Gly Val Pro Gly Gly Val Pro Gly Val
1               5                   10                  15

Gly Val Pro Gly Val Gly Val Pro Gly Val Gly Val Pro Gly Val Gly
            20                  25                  30

Val Pro

<210> SEQ ID NO 17
<211> LENGTH: 34
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 17

Gly Val Gly Val Pro Gly Val Gly Phe Pro Gly Gly Phe Pro Gly Val
1               5                   10                  15

Gly Val Pro Gly Val Gly Val Pro Gly Val Gly Val Pro Gly Val Gly
            20                  25                  30
```

Val Pro

<210> SEQ ID NO 18
<211> LENGTH: 34
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 18

Gly Val Gly Val Pro Gly Val Gly Val Pro Gly Gly Val Pro Gly Val
1               5                   10                  15

Gly Val Pro Gly Val Gly Phe Pro Gly Phe Gly Phe Pro Gly Val Gly
            20                  25                  30

Val Pro

<210> SEQ ID NO 19
<211> LENGTH: 34
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 19

Gly Val Gly Val Pro Gly Val Gly Phe Pro Gly Gly Phe Pro Gly Val
1               5                   10                  15

Gly Val Pro Gly Val Gly Phe Pro Gly Val Gly Phe Pro Gly Val Gly
            20                  25                  30

Val Pro

<210> SEQ ID NO 20
<211> LENGTH: 34
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 20

Gly Val Gly Val Pro Gly Val Gly Phe Pro Gly Gly Phe Pro Gly Val
1               5                   10                  15

Gly Val Pro Gly Val Gly Phe Pro Gly Phe Gly Phe Pro Gly Val Gly
            20                  25                  30

Val Pro

<210> SEQ ID NO 21
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(5)
<223> OTHER INFORMATION: pentamer is repeated 10 times

<400> SEQUENCE: 21

Gly Val Gly Val Pro
1               5

<210> SEQ ID NO 22
<211> LENGTH: 10
<212> TYPE: PRT
<213> ORGANISM: ARTIFICIAL SEQUENCE
<220> FEATURE:
<223> OTHER INFORMATION: SYNTHETIC CONSTRUCT

-continued

```
<220> FEATURE:
<221> NAME/KEY: repeat
<222> LOCATION: (1)..(5)
<223> OTHER INFORMATION: first 5 residues are repeated 10 times

<400> SEQUENCE: 22

Gly Val Gly Val Pro Gly Val Gly Val Pro
1               5                   10

<210> SEQ ID NO 23
<211> LENGTH: 35
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(30)
<223> OTHER INFORMATION: first 30 residues are repeated 45 times

<400> SEQUENCE: 23

Gly Val Gly Val Pro Gly Val Gly Phe Pro Gly Lys Gly Phe Pro Gly
1               5                   10                  15

Val Gly Val Pro Gly Val Gly Phe Pro Gly Phe Gly Phe Pro Gly Val
            20                  25                  30

Gly Val Pro
        35

<210> SEQ ID NO 24
<211> LENGTH: 30
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 24

Gly Phe Gly Phe Pro Gly Glu Gly Phe Pro Gly Phe Gly Phe Pro Gly
1               5                   10                  15

Phe Gly Phe Pro Gly Glu Gly Phe Pro Gly Phe Gly Phe Pro
            20                  25                  30

<210> SEQ ID NO 25
<211> LENGTH: 5
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(5)
<223> OTHER INFORMATION: pentamer is repeated 200 times

<400> SEQUENCE: 25

Gly Val Gly Val Pro
1               5

<210> SEQ ID NO 26
<211> LENGTH: 60
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 26

Gly Phe Gly Phe Pro Gly Glu Gly Phe Pro Gly Phe Gly Phe Pro Gly
1               5                   10                  15

Phe Gly Phe Pro Gly Glu Gly Phe Pro Gly Phe Gly Phe Pro Gly Phe
```

-continued

```
                20                  25                  30
Gly Phe Pro Gly Lys Gly Phe Pro Gly Phe Gly Phe Gly Phe Gly
            35                  40                  45
Phe Pro Gly Glu Gly Phe Pro Gly Phe Gly Phe Pro
            50                  55                  60

<210> SEQ ID NO 27
<211> LENGTH: 30
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: repeat
<222> LOCATION: (1)..(30)
<223> OTHER INFORMATION: sequence repeated 2n

<400> SEQUENCE: 27

Gly Phe Gly Phe Pro Gly Glu Gly Phe Pro Gly Phe Gly Phe Pro Gly
1               5                   10                  15
Phe Gly Phe Pro Gly Glu Gly Phe Pro Gly Phe Gly Phe Pro
            20                  25                  30
```